United States Patent [19]
Kamiya et al.

[11] Patent Number: 6,063,806
[45] Date of Patent: May 16, 2000

[54] INDOLYL OR INDOLINYL DERIVATIVES AND MEDICINAL USE THEREOF AS ACAT OR LIPID PEROXIDATION INHIBITORS

[75] Inventors: Shoji Kamiya, Kyoto; Hiroaki Shirahase, Nagaokakyo; Hiroshi Matsui, Nara; Shohei Nakamura, Kyoto; Katsuo Wada, Takatsuki, all of Japan

[73] Assignee: Kyoto Pharmaceutical Industries, Ltd., Japan

[21] Appl. No.: 09/051,202

[22] PCT Filed: Sep. 30, 1996

[86] PCT No.: PCT/JP96/02852

§ 371 Date: Apr. 3, 1998

§ 102(e) Date: Apr. 3, 1998

[87] PCT Pub. No.: WO97/12860

PCT Pub. Date: Apr. 10, 1997

[30] Foreign Application Priority Data

| Oct. 5, 1995 | [JP] | Japan | 7-259082 |
| Mar. 14, 1996 | [JP] | Japan | 8-058018 |
| Jul. 24, 1996 | [JP] | Japan | 8-194331 |

[51] Int. Cl.[7] ............ C07D 209/08; C07D 209/12; C07D 209/14; C07D 209/18; A61K 31/40

[52] U.S. Cl. ............ 514/418; 514/419; 548/490; 548/491; 548/483; 548/484; 548/510

[58] Field of Search ............ 548/483, 484, 548/490, 491, 510; 514/418, 419

[56] References Cited

U.S. PATENT DOCUMENTS

| 4,803,218 | 2/1989 | Stanley et al. | 514/414 |
| 5,153,226 | 10/1992 | Chucholowski et al. | 514/617 |
| 5,219,859 | 6/1993 | Festal et al. | 514/269 |

FOREIGN PATENT DOCUMENTS

| 0 622 356 A1 | 11/1994 | European Pat. Off. |
| 622356 | 11/1994 | European Pat. Off. |
| 0 708 091 A1 | 4/1996 | European Pat. Off. |
| 0 793 140 A1 | 9/1997 | European Pat. Off. |
| 2-117651 | 5/1990 | Japan |
| 3-7259 | 1/1991 | Japan |
| 3-148247 | 6/1991 | Japan |
| 4-66568 | 3/1992 | Japan |
| 4-234839 | 8/1992 | Japan |
| 4-327564 | 11/1992 | Japan |
| 5-32666 | 2/1993 | Japan |
| 5-97802 | 4/1993 | Japan |
| 5-140102 | 6/1993 | Japan |
| 8-92210 | 4/1996 | Japan |
| 8-208602 | 8/1996 | Japan |
| 96/09287 | 3/1996 | WIPO |

OTHER PUBLICATIONS

"Potential Antiatheroscelerotic Agents. 5.[1] An acyl–CoA:Cholesterol O–Acyltransferase Inhibitor with Hypocholesterolemic Activity", J. Med. Chem. vol. 29, pp. 1131–1133. 1986.

K. Yee et al., "Novel Series of Selective Leukotriene Antagonists: Exploration and Timization of the Acidic Region in 1,6–Disubstituted Indoles and Indazoles", Journal of Medicinal Chemistry, vol. 33, No. 9, pp. 2437–2451, 1990.

V. Matassa et al., "Evolution of a Series of Peptidoleukotriene Antagonists: Synthesis and Structure/Activity Relationships of 1,3, 5–substituted Indoles and Indazoles", Journal of Medicinal Chemistry, vol. 33, No. 6, pp. 1781–1790, 1990.

F. Brown et al., "Evolution of a Series of Peptidoleukotriene Antagonists: Synthesis and Structure–Activity Relationships of 1,6–Disubstituted Indoles and Indazoles", Journal of Medicinal Chemistry, vol. 33, No. 6, pp. 1771–1781, 1990.

Primary Examiner—Mukund J. Shah
Assistant Examiner—Deepak R. Rao
Attorney, Agent, or Firm—Wenderoth, Lind & Ponack, L.L.P.

[57] ABSTRACT

A heterocyclic derivative of the formula (I)

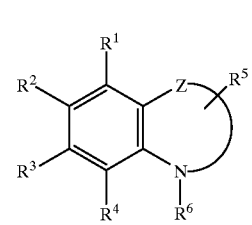

wherein each symbol is as defined in the specification, and pharmaceutically acceptable salts thereof. The compound (I) of the present invention and pharmaceutically acceptable salts thereof exhibit superior ACAT inhibitory activity and lipoperoxidation inhibitory activity in mammals, and are useful as ACAT inhibitors and lipoperoxidation inhibitors. Specifically, they are useful for the prophylaxis and treatment of arteriosclerosis, hyperlipemia, arteriosclerosis in diabetes, and cerebrovascular and cardiovascular ischemic diseases.

19 Claims, No Drawings ion of cholesterol accumulated as cholesterol ester in arterial walls. In addition, it is known that hyperoxidation of lipids in a living body is deeply concerned with the onset of arteriosclerosis and cerebrovascular and cardiovascular ischemic diseases.

INDOLYL OR INDOLINYL DERIVATIVES AND MEDICINAL USE THEREOF AS ACAT OR LIPID PEROXIDATION INHIBITORS

This is a national stage of international application no. PCT/JP96/02852 filed Sep. 30, 1996.

TECHNICAL FIELD

The present invention relates to novel heterocyclic derivatives and pharmaceutical use thereof. More particularly, the present invention relates to novel heterocyclic derivatives having an indoline ring, indole ring or tetrahydroquinoline ring, which derivatives having an inhibitory activity on acyl CoA: cholesterol acyltransferase (hereinafter ACAT) and lipoperoxidation inhibitory activity, and to pharmaceutical use thereof.

BACKGROUND ART

It is a well-known fact that arteriosclerosis is an extremely important factor causing various circulatory diseases, and active studies have been undertaken in an attempt to achieve suppression of the evolution of arterial sclerosis or regression thereof. In particular, although the usefulness of a pharmaceutical agent which reduces cholesterol in blood or arterial walls has been acknowledged, an ideal pharmaceutical agent exhibiting positive clinical effects while causing less side-effects has not been realized. A pharmaceutical agent which directly inhibits deposition of cholesterol in arterial walls has been desired as a pharmaceutical agent which effectively prevents or treats arterial sclerosis, and studies in this field are thriving. Yet, an ideal pharmaceutical agent has not been developed.

In recent years, it has been clarified that cholesterol in blood is accumulated in arterial walls in the ester form thereof, and that it significantly evolves arteriosclerosis. A decrease in cholesterol level in blood leads to the reduction of accumulation of cholesterol ester in arterial walls, and is effective for the suppression of evolution of arteriosclerosis and regression thereof.

Cholesterol in food is esterified in mucous membrane of small intestine, and taken into blood as chylomicron. ACAT is known to play an important role in the generation of cholesterol ester in mucous membrane of small intestine. Thus, if esterification of cholesterol can be suppressed by inhibiting ACAT in mucous membrane of small intestine, absorption of cholesterol by mucous membrane and into blood can be presumably prevented to ultimately result in lower cholesterol level in blood.

In arterial walls, ACAT esterifies cholesterol and causes accumulation of cholesterol ester. Inhibition of ACAT in arterial walls is expected to effectively suppress accumulation of cholesterol ester.

From the foregoing, it is concluded that an ACAT inhibitor will make an effective pharmaceutical agent for hyperlipemia and arteriosclerosis, as a result of suppression of absorption of cholesterol in small intestine and accumulation of cholesterol in arterial walls.

Conventionally, there have been reported, for example, as such ACAT inhibitors, amide and urea derivatives [J. Med. Chem., 29: 1131 (1986), Japanese Patent Unexamined Publication Nos. 117651/1990, 7259/1990, 234839/1992, 327564/1992 and 32666/1993]. However, creation and pharmacological studies of these compounds have been far from sufficient.

Meanwhile, hyperoxidation of low density lipoprotein (LDL) is also highly responsible for intracellular incorporation of cholesterol accumulated as cholesterol ester in arterial walls. In addition, it is known that hyperoxidation of lipids in a living body is deeply concerned with the onset of arteriosclerosis and cerebrovascular and cardiovascular ischemic diseases.

Accordingly, a compound having both an ACAT inhibitory activity and lipoperoxidation inhibitory activity is highly useful as a pharmaceutical product, since it effectively reduces accumulation of cholesterol ester in arterial walls and inhibits lipoperoxidation in living organisms, thereby preventing and treating various vascular diseases caused thereby.

It is therefore an object of the present invention to provide a compound having ACAT inhibitory activity and lipoperoxidation inhibitory activity, as well as pharmaceutical use thereof, particularly ACAT inhibitor and lipoperoxidation inhibitor.

DISCLOSURE OF THE INVENTION

The present inventors have conducted intensive studies to achieve the above-mentioned objects and found that a certain heterocyclic derivative having an indoline ring, indole ring or tetrahydroquinoline ring is superior in water solubility as compared to conventional ACAT inhibitors, and has lipoperoxidation inhibitory activity in addition to strong ACAT inhibitory activity, and that said compound permits superior oral absorption, strong anti-hyperlipemia effect and anti-arteriosclerosis effect, which resulted in the completion of the present invention.

Thus, the present invention relates to heterocyclic derivatives of the formula (I)

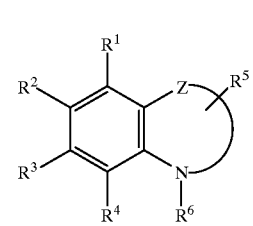

(I)

wherein
one of $R^1$, $R^2$ and $R^5$ is hydroxy, carboxy, alkoxycarbonyl, a group of the formula —$NR^9R^{10}$ wherein $R^9$ and $R^{10}$ are each independently hydrogen atom or lower alkyl, or alkyl or alkenyl substituted by hydroxy, acidic group, alkoxycarbonyl or a group of the formula —$NR^9R^{10}$ wherein $R^9$ and $R^{10}$ are each independently hydrogen atom or lower alkyl, and the other two are each independently hydrogen atom, lower alkyl or lower alkoxy;
either $R^3$ or $R^4$ is a group of the formula —$NHCOR^7$ wherein $R^7$ is alkyl, alkoxyalkyl, alkylthioalkyl, cycloalkyl, cycloalkylalkyl, aryl, arylalkyl or a group of the formula —$NHR^8$ wherein $R^8$ is alkyl, cycloalkyl, cycloalkylalkyl, aryl or arylalkyl, and the other is hydrogen atom, lower alkyl or lower alkoxy;
$R^6$ is alkyl, alkenyl, alkoxyalkyl, alkylthioalkyl, cycloalkyl, cycloalkylalkyl or arylalkyl; and
Z is a binding group forming a 5- or 6-membered ring together with nitrogen atom substituted by $R^6$, carbon atom of benzene ring to which said nitrogen atom binds and carbon atom adjacent to said carbon atom,
and pharmaceutically acceptable salts thereof.

The present invention also relates to pharmaceutical compositions, ACAT inhibitors and lipoperoxidation inhibitors containing the above-mentioned heterocyclic derivative or a pharmaceutically acceptable salt thereof.

In the present specification, each symbol denotes the following.

Lower alkyl at $R^1$, $R^{1a}$, $R^{1b}$, $R^{1c}$, $R^2$, $R^{2c}$, $R^3$, $R^{3a}$, $R^{3b}$, $R^{3c}$, $R^4$, $R^{4c}$, $R^5$, $R^{5c}$, $R^9$, $R^{9c}$, $R^{10}$ and $R^{10c}$ may be linear or branched and has 1 to 6 carbon atoms. Examples thereof include methyl, ethyl, propyl, isopropyl, butyl, isobutyl, sec-butyl, tert-butyl, pentyl, isopentyl, neopentylhexyl and the like.

Lower alkoxy at $R^1$, $R^{1b}$, $R^{1c}$, $R^2$, $R^{2c}$, $R^3$, $R^{3b}$, $R^{3c}$, $R^4$, $R^{4c}$, $R^5$ and $R^{5c}$ may be linear or branched and has 1 to 6 carbon atoms. Examples thereof include methoxy, ethoxy, propoxy, isopropoxy, butoxy, isobutoxy, sec-butoxy, tert-butoxy, pentyloxy, isopentyloxy, neopentyloxy, hexyloxy and the like.

Alkyl at $R^6$, $R^{6a}$, $R^{6b}$, $R^{6c}$, $R^7$, $R^{7a}$, $R^{7b}$, $R^{7c}$, $R^8$, $R^{8b}$ and $R^{8c}$ may be linear or branched and preferably has 1 to 20 carbon atoms. Examples thereof include methyl, ethyl, propyl, isopropyl, butyl, isobutyl, sec-butyl, tert-butyl, pentyl, isopentyl, neopentyl, hexyl, heptyl, octyl, nonyl, decyl, undecyl, dodecyl, tridecyl, tetradecyl, pentadecyl, hexadecyl, heptadecyl, nonadecyl, icosyl, 1,1-dimethylpropyl, 1,1-dimethylbutyl, 1,1-dimethylhexyl, 1,1-dimethylheptyl, 3,3-dimethylbutyl, 4,4-dimethylbutyl and the like.

In alkoxyalkyl at $R^6$, $R^{6b}$, $R^{6c}$, $R^7$, $R^{7b}$ and $R^{7c}$, the alkoxy moiety thereof preferably has 1 to 6 carbon atoms and alkyl moiety thereof preferably has 1 to 6 carbon atoms. Examples of alkoxyalkyl include ethoxybutyl, ethoxyhexyl, butoxybutyl, butoxyhexyl, hexyloxybutyl, hexyloxyhexyl and the like.

In alkylthioalkyl at $R^6$, $R^{6b}$, $R^{6c}$, $R^7$, $R^{7b}$ and $R^{7c}$, both alkyl moieties preferably have 1 to 6 carbon atoms. Examples of alkylthioalkyl include ethylthioethyl, ethylthiohexyl, butylthiobutyl, butylthiohexyl, hexylthiobutyl, hexylthiohexyl and the like.

Cycloalkyl at $R^6$, $R^{6a}$, $R^{6b}$, $R^{6c}$, $R^7$, $R^{7a}$, $R^{7b}$, $R^{7c}$, $R^8$, $R^{8b}$ and $R^{8c}$ preferably has 3 to 8 carbon atoms. Examples thereof include cyclopropyl, cyclobutyl, cyclopentyl, cyclohexyl, cycloheptyl, cyclooctyl and the like.

In cycloalkylalkyl at $R^6$, $R^{6a}$, $R^{6b}$, $R^{6c}$, $R^7$, $R^{7a}$, $R^{7b}$, $R^{7c}$, $R^8$, $R^{8b}$ and $R^{8c}$, its cycloalkyl moiety preferably has 3 to 8 carbon atoms and alkyl moiety preferably has 1 to 3 carbon atoms. Examples of cycloalkylalkyl include cyclopropylmethyl, cyclobutylmethyl, cyclopentylmethyl, cyclohexylmethyl, cyclopropylethyl, cyclopropylpropyl, cycloheptylmethyl, cyclooctylmethyl and the like.

Examples of aryl at $R^7$, $R^{7b}$, $R^{7c}$, $R^8$, $R^8$b and $R^{8c}$ include phenyl, naphthyl and the like.

Arylalkyl at $R^6$, $R^{6b}$, $R^{6c}$, $R^7$, $R^{7b}$, $R^{7c}$, $R^8$, $R^{8b}$ and $R^{8c}$ has the aforementioned aryl moiety and its alkyl moiety preferably has 1 to 4 carbon atoms. Examples of arylalkyl include benzyl, 1-phenylethyl, 2-phenylethyl, 1-phenylpropyl, 2-phenylpropyl, 3-phenylpropyl and the like.

Alkenyl at $R^6$, $R^{6b}$ and $R^{6c}$ may be linear or branched and preferably has 3 to 12 carbon atoms. Examples thereof include propenyl, isopropenyl, butenyl, pentenyl, hexenyl, heptenyl, octenyl, 3,3-dimethyl-2-propenyl and the like.

Acidic group at $R^1$, $R^2$ and $R^5$ is exemplified by carboxy, sulfonic acid group, phosphonic acid group and the like. Examples of alkoxycarbonyl at $R^1$, $R^{1c}$, $R^2$, $R^{2b}$, $R^{2c}$, $R^5$ and $R^{5c}$ include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl and the like.

Alkyl to be substituted at $R^1$, $R^2$, $R^{2a}$, $R^{2b}$ and $R^5$ may be linear or branched and preferably has 1 to 8 carbon atoms. Examples thereof include methyl, ethyl, propyl, butyl, pentyl, hexyl, 1,1-dimethylethyl, 2,2-dimethylpropyl and the like. Examples of substituted alkyl include hydroxymethyl, hydroxyethyl, carboxymethyl, carboxyethyl, carboxypropyl, ethoxycarbonylmethyl, dimethylaminomethyl, dimethylaminoethyl, sulfomethyl, phosphonomethyl and the like.

Alkenyl to be substituted at $R^1$, $R^2$ and $R^5$ may be linear or branched and preferably has 2 to 8 carbon atoms. Examples thereof include vinyl, propenyl, isopropenyl, butenyl, pentenyl, hexenyl, heptenyl, octenyl, 3,3-dimethyl-2-propenyl and the like. Examples of substituted alkenyl include carboxyvinyl, carboxypropenyl, hydroxypropenyl and the like.

Z is preferably

In the compounds of the present invention, ① when one of $R^1$, $R^2$ and $R^5$ is alkyl or alkenyl substituted by hydroxy, acidic group, alkoxycarbonyl or a group of the formula —$NR^9R^{10}$ wherein $R^9$ and $R^{10}$ are each independently hydrogen atom or lower alkyl, and the other two are independently hydrogen atom, lower alkyl or lower alkoxy, the compound may be (a) indoline or indole derivative, or (b) tetrahydroquinoline derivative.

(a) When the compound of the present invention is indoline or indole derivative, preferable compound is that of the above-mentioned formula (I) wherein one of $R^1$, $R^2$ and $R^5$ is alkyl substituted by hydroxy, carboxy, alkoxycarbonyl or a group of the formula —$NR^9R^{10}$ wherein $R^9$ and $R^{10}$ are each independently lower alkyl, and the other two are independently hydrogen atom, lower alkyl or lower alkoxy; either $R^3$ or $R^4$ is a group of the formula —$NHCOR^7$ wherein $R^7$ is alkyl, alkoxyalkyl, alkylthioalkyl, cycloalkyl, cycloalkylalkyl, aryl, arylalkyl or a group of the formula —$NHR^8$ wherein $R^8$ is alkyl, and the other is hydrogen atom, lower alkyl or lower alkoxy; and $R^6$ is as defined above.

A more preferable compound is that of the above-mentioned formula (I) wherein $R^1$ and $R^3$ are each independently hydrogen atom, lower alkyl or lower alkoxy; either $R^2$ or $R^5$ is alkyl substituted by hydroxy, carboxy, alkoxycarbonyl or a group of the formula —$NR^9R^{10}$ wherein $R^9$ and $R^{10}$ are each independently lower alkyl, and the other is hydrogen atom, lower alkyl or lower alkoxy; $R^4$ is a group of the formula —$NHCOR^7$ wherein $R^7$ is alkyl, alkoxyalkyl, alkylthioalkyl, cycloalkyl, cycloalkylalkyl, aryl, arylalkyl or a group of the formula —$NHR^8$ wherein $R^8$ is alkyl; and $R^6$ is as defined above.

A still more preferable compound is that of the above-mentioned formula (I) wherein $R^1$ and $R^3$ are each independently hydrogen atom, lower alkyl or lower alkoxy; either $R^2$ or $R^5$ is alkyl substituted by hydroxy, carboxy, alkoxycarbonyl or a group of the formula —$NR^9R^{10}$ wherein $R^9$ and $R^{10}$ are each independently lower alkyl, and the other is hydrogen atom; $R^4$ is a group of the formula —$NHCOR^7$ wherein $R^7$ is alkyl, alkoxyalkyl, alkylthioalkyl, cycloalkyl, cycloalkylalkyl, aryl, arylalkyl or a group of the formula —$NHR^8$ wherein $R^8$ is alkyl; and $R^6$ is as defined above.

A still more preferable compound is that of the above-mentioned formula (I) wherein $R^1$ and $R^3$ are each independently hydrogen atom or lower alkyl; either $R^2$ or $R^5$ is alkyl substituted by hydroxy, carboxy, alkoxycarbonyl or a group of the formula —$NR^9R^{10}$ wherein $R^9$ and $R^{10}$ are each independently lower alkyl, and the other is hydrogen atom; $R^4$ is a group of the formula —$NHCOR^7$ wherein $R^7$ is alkyl, cycloalkyl or cycloalkylalkyl; and $R^6$ is alkyl, cycloalkyl or cycloalkylalkyl.

A still more preferable compound is that of the above-mentioned formula (I) wherein $R^1$ and $R^3$ are each independently hydrogen atom or lower alkyl; $R^2$ is alkyl substituted by hydroxy, carboxy, alkoxycarbonyl or a group of the formula —$NR^9R^{10}$ wherein $R^9$ and $R^{10}$ are each independently lower alkyl, and $R^5$ is hydrogen atom; $R^4$ is a group of the formula —$NHCOR^7$ wherein $R^7$ is alkyl, cycloalkyl or cycloalkylalkyl; and $R^6$ is alkyl, cycloalkyl or cycloalkylalkyl.

A still more preferable compound is that of the following formula (IIa):

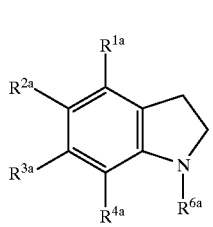

(IIa)

wherein $R^{1a}$ is hydrogen atom or lower alkyl; $R^{3a}$ is lower alkyl; $R^{2a}$ is alkyl substituted by hydroxy or carboxy; $R^{4a}$ is a group of the formula —$NHCOR^{7a}$ wherein $R^{7a}$ is alkyl, cycloalkyl or cycloalkylalkyl; and $R^{6a}$ is alkyl, cycloalkyl or cycloalkylalkyl.

A still more preferable compound is that of the above formula (IIa) wherein $R^{1a}$ is hydrogen atom or lower alkyl; $R^{3a}$ is lower alkyl; $R^{2a}$ is alkyl substituted by hydroxy or carboxy; $R^{4a}$ is a group of the formula —NHCORla wherein $R^{7a}$ is alkyl; and $R^{6a}$ is alkyl.

Examples of the most preferable compound include N-(1-hexyl-5-carboxymethyl-4,6-dimethylindolin-7-yl)-2,2-dimethylpropanamide, N-(1-heptyl-5-carboxymethyl -4,6-dimethylindolin-7-yl)-2,2-dimethylpropanamide, N-(1-octyl-5-carboxymethyl-4,6-dimethylindolin-7-yl)-2,2-dimethylpropanamide, N-(1-nonyl-5-carboxymethyl-4,6-dimethylindolin-7-yl)-2,2-dimethylpropanamide, N-(1-decyl-5-carboxymethyl-4,6-dimethylindolin-7-yl)-2,2-dimethylpropanamide, N-(1-undecyl-5-carboxymethyl-4,6-dimethylindolin-7-yl)-2,2-dimethylpropanamide, N-(1-dodecyl-5-carboxymethyl-4,6-dimethylindolin-7-yl)-2,2-dimethylpropanamide, N-(1-hexyl-5-hydroxymethyl-6-methylindolin-7-yl)-2,2-dimethylpropanamide, N-(1-hexyl-5-hydroxymethyl-4,6-dimethylindolin-7-yl)-2,2-dimethylpropanamide, N-(1-heptyl-5-hydroxymethyl-6-methylindolin-7-yl)-2,2-dimethylpropanamide, N-(1-heptyl-5-hydroxymethyl-4,6-dimethylindolin-7-yl)-2,2-dimethylpropanamide, N-(1-octyl-5-hydroxymethyl-6-methylindolin-7-yl)-2,2-dimethylpropanamide, N-(1 -octyl-5-hydroxymethyl-4,6-dimethylindolin-7-yl)-2,2-dimethylpropanamide and the like, and pharmaceutically acceptable salts thereof.

(b) When the compound of the present invention is a tetrahydroquinoline derivative, a compound of the following (IIb) is preferable.

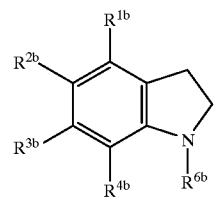

(IIb)

wherein $R^{1b}$ and $R^{3b}$ are each independently hydrogen atom, lower alkyl or lower alkoxy; $R^{2b}$ is alkyl substituted by hydroxy, carboxy or alkoxycarbonyl; $R^{4b}$ is a group of the formula —$NHCOR^{7b}$ wherein $R^{7b}$ is alkyl, alkoxyalkyl, alkylthioalkyl, cycloalkyl, cycloalkylalkyl, aryl, arylalkyl or a group of the formula —$NHR^{8b}$ wherein $R^{8b}$ is alkyl, cycloalkyl, cycloalkylalkyl, aryl or arylalkyl; and $R^{6b}$ is alkyl, alkenyl, alkoxyalkyl, alkylthioalkyl, cycloalkyl, cycloalkylalkyl or arylalkyl.

A still more preferable compound is that of the formula (IIb) wherein $R^{1b}$ and $R^{3b}$ are each independently lower alkyl or lower alkoxy; $R^{2b}$ is alkyl substituted by hydroxy, carboxy or alkoxycarbonyl; $R^{4b}$ is a group of the formula —$NHCOR^{7b}$ wherein $R^{7b}$ is alkyl, cycloalkylalkyl, arylalkyl or a group of the formula —$NHR^{8b}$ wherein $R^{8b}$ is alkyl; and $R^{6b}$ is alkyl, alkoxyalkyl, alkylthioalkyl or cycloalkylalkyl.

A still more preferable compound is that of the formula (IIb) wherein $R^{1b}$ and $R^{3b}$ are each independently lower alkyl; $R^{2b}$ is alkyl substituted by hydroxy or carboxy; $R^{4b}$ is a group of the formula —$NHCOR^{7b}$ wherein $R^{7b}$ is alkyl; and $R^{6b}$ is alkyl.

Examples of the most preferable compound include N-(1-hexyl-6-carboxymethyl-5,7-dimethyl-1,2,3,4-tetrahydroquinolin-8-yl)-2,2-dimethylpropanamide, N-(1-heptyl-6-carboxymethyl-5,7-dimethyl-1,2,3,4-tetrahydroquinolin-8-yl)-2,2-dimethylpropanamide, N-(1-octyl-6-carboxymethyl-5,7-dimethyl-1,2,3,4-tetrahydroquinolin-8-yl)-2,2-dimethylpropanamide, N-(1-nonyl-6-carboxymethyl-5,7-dimethyl-1,2,3,4-tetrahydroquinolin-8-yl)-2,2-dimethylpropanamide, N-(1-decyl-6-carboxymethyl- 5,7-dimethyl-1,2,3,4-tetrahydroquinolin-8-yl)-2,2-dimethylpropanamide, N-(1-hexyl-6-hydroxymethyl-5,7-dimethyl-1,2,3,4-tetrahydroquinolin-8-yl)-2,2-dimethylpropanamide, N-(1-heptyl-6-hydroxymethyl-5,7-dimethyl-1,2,3,4-tetrahydroquinolin-8-yl)-2,2-dimethylpropanamide, N-(1-octyl-6-hydroxymethyl-5,7-dimethyl-1,2,3,4-tetrahydroquinolin-8-yl)-2,2-dimethylpropanamide, N-(1-nonyl-6-hydroxymethyl-5,7-dimethyl-1,2,3,4-tetrahydroquinolin-8-yl)-2,2-dimethylpropanamide, N-(1-decyl-6-hydroxymethyl-5,7-dimethyl-1,2,3,4-tetrahydroquinolin-8-yl)-2,2-dimethylpropanamide and the like, and pharmaceutically acceptable salts thereof.

② When the compound of the present invention is that wherein one of $R^1$, $R^2$ and $R^5$ is hydroxy, carboxy, alkoxycarbonyl or a group of the formula —$NR^9R^{10}$ wherein $R^9$ and $R^{10}$ are each independently hydrogen atom or lower alkyl, and the other two are independently hydrogen atom, lower alkyl or lower alkoxy, the compound of the following formula (IIc) is preferable.

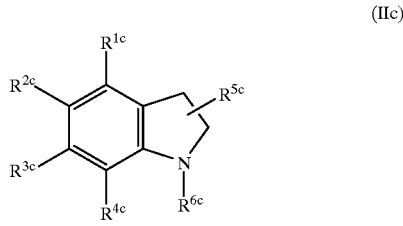

(IIc)

wherein one of $R^{1c}$, $R^{2c}$ and $R^{5c}$ is hydroxy, carboxy, alkoxycarbonyl or a group of the formula —$NR^{9c}R^{10c}$ wherein $R^{9c}$ and $R^{10c}$ are each independently hydrogen atom or lower alkyl, and the other two are each independently hydrogen atom, lower alkyl or lower alkoxy; either $R^{3c}$ or $R^{4c}$ is a group of the formula —$NHCOR^{7c}$ wherein $R^{7c}$ is alkyl, alkoxyalkyl, alkylthioalkyl, cycloalkyl, cycloalkylalkyl, aryl, arylalkyl or a group of the formula —$NHR^{8c}$ wherein $R^{8c}$ is alkyl, cycloalkyl, cycloalkylalkyl, aryl or arylalkyl, and the other is hydrogen atom, lower alkyl or lower alkoxy; and $R^c$ is alkyl, alkenyl, alkoxyalkyl, alkylthioalkyl, cycloalkyl, cycloalkylalkyl or arylalkyl.

More preferable compound is a compound of the above formula (IIc) wherein $R^{1c}$ and $R^{3c}$ are each independently hydrogen atom, lower alkyl or lower alkoxy; $R^{2c}$ is carboxy; $R^{4c}$ is a group of the formula —$NHCOR^{7c}$ wherein $R^{7c}$ is alkyl, cycloalkyl or cycloalkylalkyl; $R^{5c}$ is hydrogen atom; and $R^{6c}$ is alkyl, cycloalkyl or cycloalkylalkyl.

A still more preferable compound is a compound of the above formula (IIc) wherein $R^{1c}$ is hydrogen atom or lower alkyl; $R^{3c}$ is lower alkyl; $R^{2c}$ is carboxy; $R^{4c}$ is a group of the formula —$NHCOR^{7c}$ wherein $R^{7c}$ is alkyl; $R^{5c}$ is hydrogen atom; and $R^{6c}$ is alkyl.

Examples of the most preferable compound include N-(1-hexyl-5-carboxy-6-methylindolin-7-yl)-2,2-dimethylpropanamide, N-(1-octyl-5-carboxy-6-methylindolin-7-yl)-2,2-dimethylpropanamide, N-(1-decyl-5-carboxy-6-methylindolin-7-yl)-2,2-dimethylpropanamide, N-(1-hexyl-5-carboxy-4,6-dimethylindolin-7-yl)-2,2-dimethylpropanamide, N-(1-octyl-5-carboxy-4,6-dimethylindolin-7-yl)-2,2-dimethylpropanamide, N-(1-decyl-5-carboxy-4,6-dimethylindolin-7-yl)-2,2-dimethylpropanamide and the like, and pharmaceutically acceptable salts thereof.

The compound (I) may form pharmaceutically acceptable salts. When compound (I) has a basic group, it can form acid addition salts. The acid to form such acid addition salts is subject to no particular limitation as long as it can form a salt with a basic moiety and is a pharmaceutically acceptable acid. Examples of such acid include inorganic acids such as hydrochloric acid, sulfuric acid, phosphoric acid, nitric acid and the like, and organic acids such as oxalic acid, fumaric acid, maleic acid, citric acid, tartaric acid, methanesulfonic acid, toluenesulfonic acid and the like.

When compound (I) has an acidic group such as carboxy, it can form, for example, alkali metal salts such as sodium salt, potassium salt and the like; alkaline earth metal salts such as calcium salt, magnesium salt and the like; and organic base salts such as triethylamine salt, dicyclohexylamine salt, pyridine salt and the like.

The compound (I) of the present invention and pharmaceutically acceptable salts thereof can be produced by any one of the following methods 1 to 7.

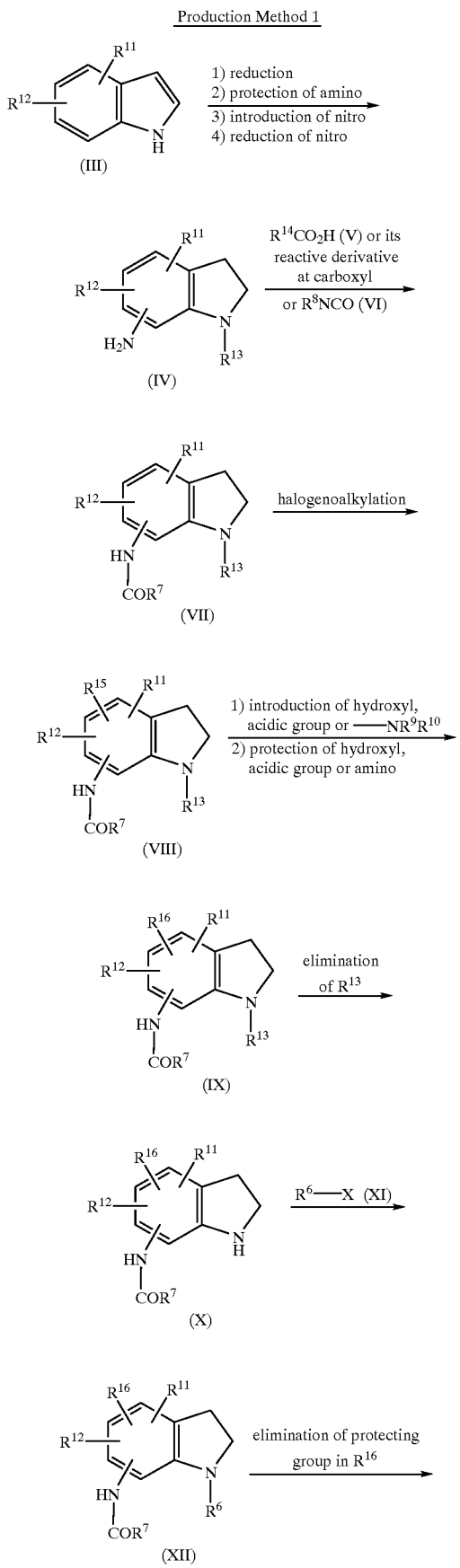

Production Method 1

-continued
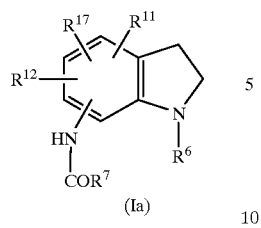
(Ia)
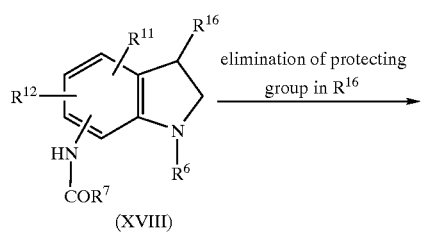
(XVIII)
Production Method 2
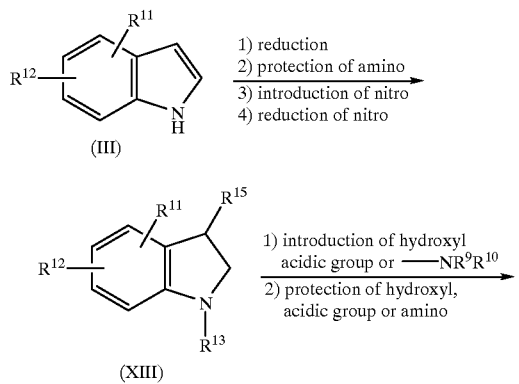
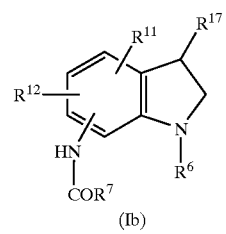
(Ib)
Production Method 3
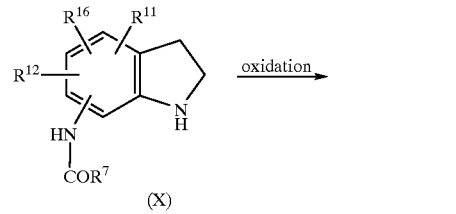
(X)
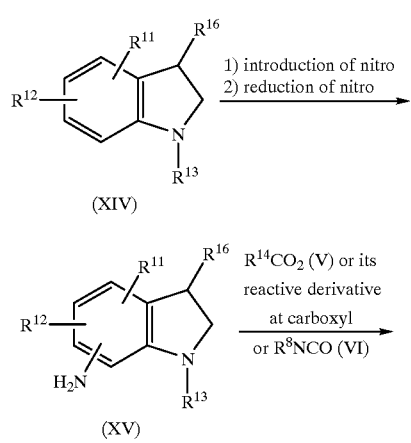
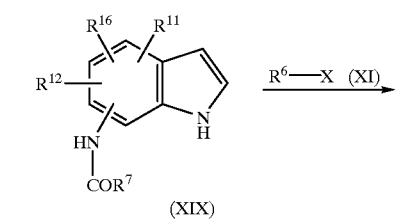
(XIX)
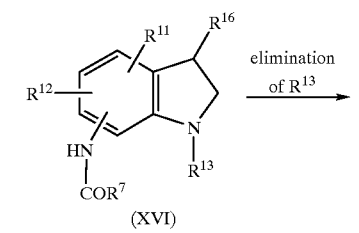
(XVI)
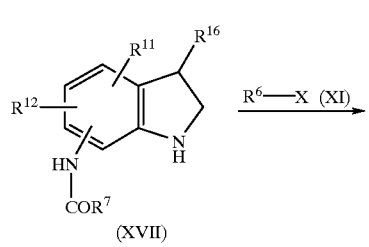
(XVII)
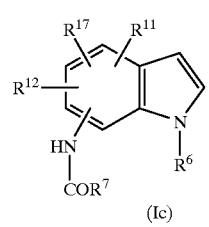
(Ic)

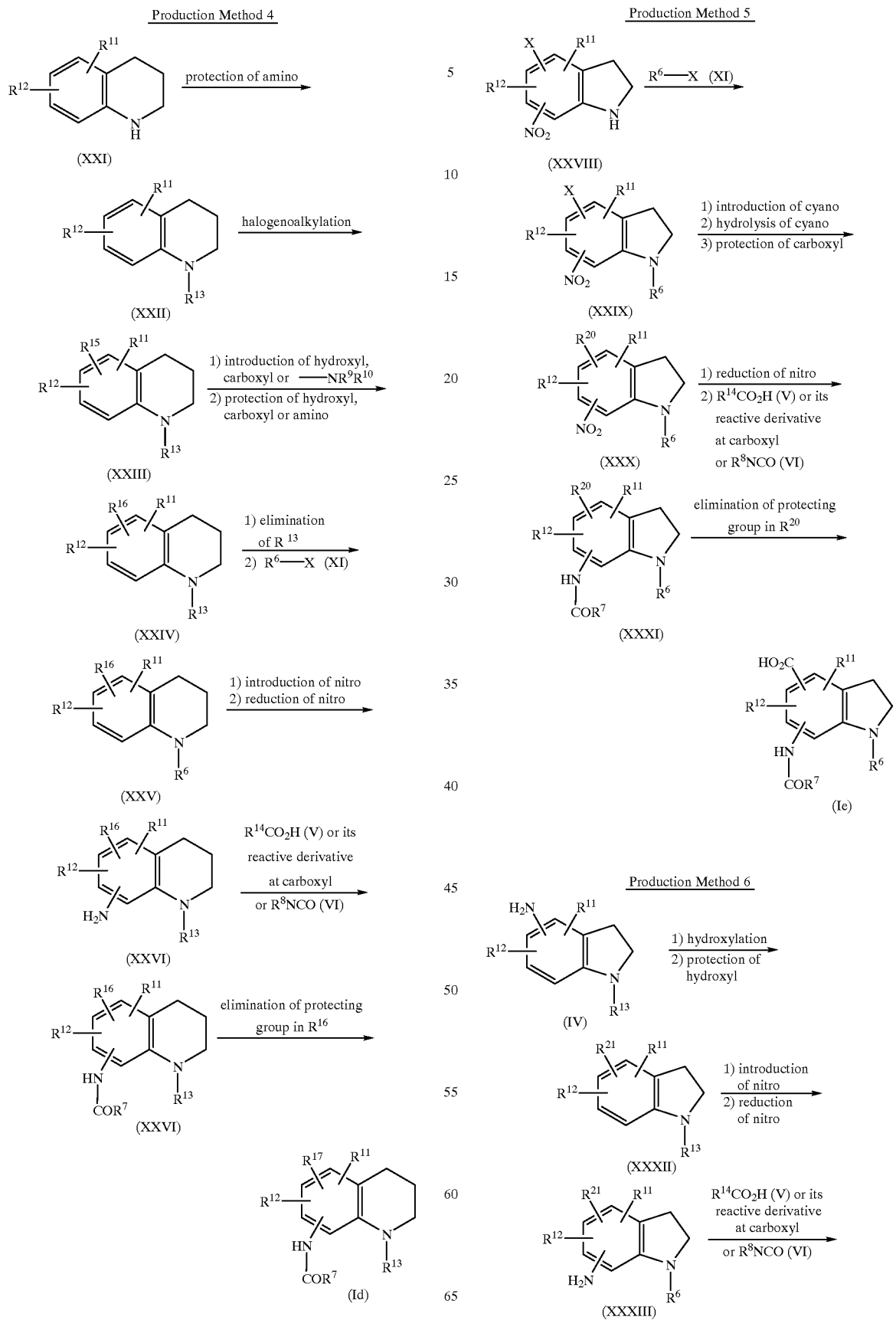

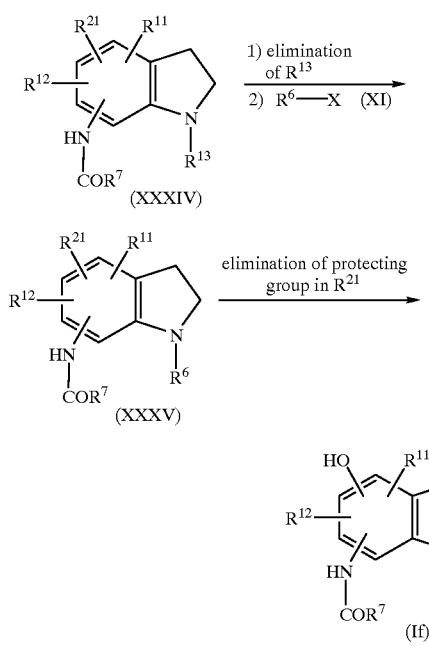

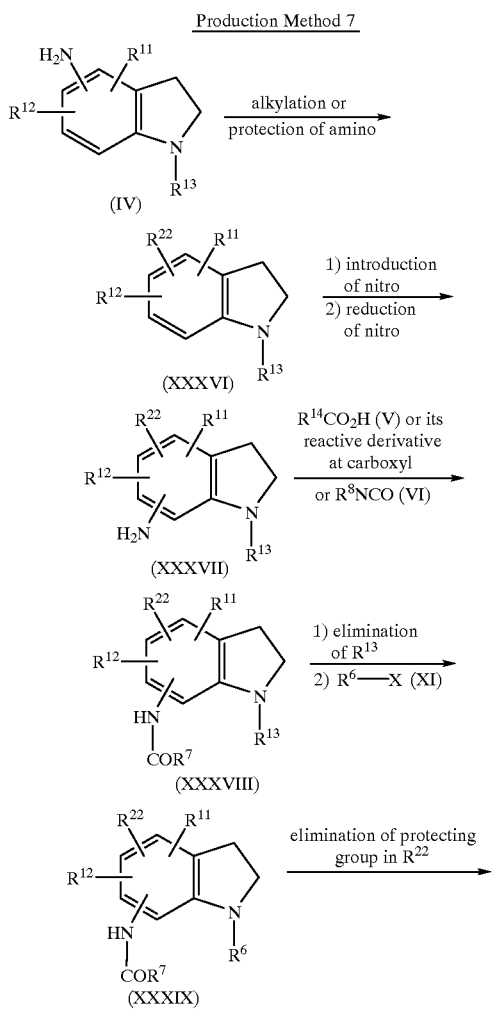

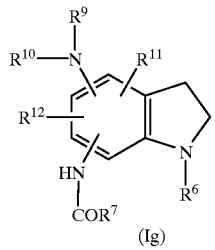

In each of the above formulas, $R^6$, $R^7$, $R^8$, $R^9$ and $R^{10}$ are each as defined above; $R^{11}$ and $R^{12}$ are each independently hydrogen atom, lower alkyl or lower alkoxy; $R^{13}$ is amino protecting group; $R^{14}$ is alkyl, alkoxyalkyl, alkylthioalkyl, cycloalkyl, cycloalkylalkyl, aryl or arylalkyl; $R^{15}$ is alkyl or alkenyl substituted by halogen atom; $R^{16}$ is alkyl or alkenyl substituted by hydroxy, protected hydroxy, acidic group, protected acidic group, alkoxycarbonyl or $-NR^{18}R^{19}$ wherein $R^{18}$ and $R^{19}$ are each independently hydrogen atom, lower alkyl or amino protecting group; $R^{17}$ is alkyl or alkenyl substituted by hydroxy, acidic group, alkoxycarbonyl or $-NR^9R^{10}$; $R^{20}$ is protected carboxy; $R^{21}$ is protected hydroxy; and $R^{22}$ is $-NR^{18}R^{19}$ wherein $R^{18}$ and $R^{19}$ are as defined above.

Amino protecting group at $R^{13}$, $R^{18}$ and $R^{19}$ is, for example, formyl, monochloroacetyl, dichloroacetyl, trifluoroacetyl, methoxycarbonyl, ethoxycarbonyl, benzyloxycarbonyl, p-nitrobenzyloxycarbonyl, diphenylmethyloxycarbonyl, methoxymethyloxycarbonyl, 2,2,2-trichloroethoxycarbonyl, trimethylsilyl, 2-methylsulfonylethyloxycarbonyl, tert-butoxycarbonyl or trityl.

Hydroxy protecting group at $R^{16}$ and $R^{21}$ is, for example, formyl, acetyl, monochloroacetyl, dichloroacetyl, trifluoroacetyl, methoxycarbonyl, ethoxycarbonyl, benzyloxycarbonyl, 2,2,2-trichloroethoxycarbonyl, benzoyl, trityl, tetrahydropyranyl, trimethylsilyl or the like.

Acidic group protecting group at $R^{16}$ and $R^{20}$ is, when carboxy protecting group, for example, methyl, ethyl, n-propyl, isopropyl, n-butyl, sec-butyl, tert-butyl, tert-amyl, benzyl, p-nitrobenzyl, p-methoxybenzyl, benzhydryl, p-nitrophenyl, methoxymethyl, ethoxymethyl, benzyloxymethyl, methylthiomethyl, trityl, 2,2,2-trichloroethyl, trimethylsilyl, diphenylmethoxybenzenesulfonylmethyl, dimethylaminoethyl and the like.

The above-mentioned protecting groups can be removed by a method known per se, and the method for removing them may be determined according to the kind of the protecting group. Exemplified are a decomposition by an acid (e.g., that by an acid such as hydrochloric acid, trifluoroacetic acid and the like for formyl, tert-butoxycarbonyl, trityl, tetrahydropyranyl and the like); a decomposition by a base (e.g., that by a base such as sodium hydroxide, potassium hydroxide, sodium carbonate, sodium bicarbonate and the like for acetyl, dichloroacetyl, trifluoroacetyl and the like); and catalytic reduction (e.g., decomposition by palladium-carbon and the like for benzyl, benzyloxycarbonyl and the like). The production methods of the objective compounds of the present invention and starting material compound are described in detail in the following.

Production Method 1

The compound (IV) can be produced by reducing compound (III) [J. Eric Nordlander, et al., J. Org. Chem., 46, 778–782 (1981), Robin D. Clark, et al., Heterocycle, 22, 195–221 (1984), Vernon H. Brown, et al., J. Heterocycle. Chem., 6(4), 539–543 (1969)] to introduce an indoline skeleton, protecting amino, introducing nitro on benzene ring by a method known per se, and reducing nitro using a catalyst such as palladium-carbon.

The compound (VII) can be produced by reacting compound (IV) with compound (V) or reactive derivative thereof at carboxy group, or compound (VI).

Said reaction is generally carried out in an inert solvent. Examples of the inert solvent include acetone, dioxane, acetonitrile, chloroform, benzene, methylene chloride, ethylene chloride, tetrahydrofuran, ethyl acetate, N,N-dimethylformamide, pyridine, water and mixed solvents thereof.

In addition, a base such as triethylamine, pyridine, 4-dimethylaminopyridine, potassium carbonate and the like can be used.

The reaction temperature is generally −10–160° C., preferably 0–60° C., and reaction time is generally from 30 min to 10 hr.

The compound (V) can be subjected to the instant reaction as a free carboxylic acid or a reactive derivative thereof, and the both modes are encompassed in the present invention. That is, it is used in this reaction as a free acid or a salt such as sodium, potassium, calcium, triethylamine, pyridine and the like, or as a reactive derivative such as its acid halide (e.g., acid chloride, acid bromide and the like), acid anhydride, mixed acid anhydride [e.g., substituted phosphoric acid (dialkyl phosphate and the like), alkyl carbonate (monoethylcarbonate and the like) and the like], active amide (amide with imidazole and the like), ester (cyanomethyl ester, 4-nitrophenyl ester etc.), and the like.

When compound (V) is used as a free acid or a salt in this reaction, a condensing agent is preferably used. Examples of the condensing agent include dehydrating agents such as N,N'-disubstituted carbodiimides (e.g., N,N'-dicyclohexylcarbodiimide); carbodiimide compounds (e.g., 1-ethyl-3-(3'-dimethylaminopropyl)carbodiimide, N-cyclohexyl-N'-morpholinoethyl carbodiimide and N-cyclohexyl-N'-(4-diethylaminocyclohexyl)carbodiimide); azolide compounds (e.g., N,N'-carbonyldiimidazole and N,N'-thionyldiimidazole); and the like. When these condensing agents are used, the reaction is considered to proceed via a reactive derivative of carboxylic acid. The compound (VIII) can be produced by halogenoalkylation of compound (VII) [R.C. Fuson et al., Org. React., 1, 63 (1969), G. A. Olah et al., "Friedel Crafts and Related Reactions" Vol. 2. 659 (1964)].

The compound (IX) can be produced by converting halogenoalkyl of compound (VIII) to hydroxy, an acidic group such as carboxy or a group of the formula —$NR^9R^{10}$ by a substituent conversion reaction known per se, and if necessary, introducing a corresponding protecting group.

The compound (XII) can be produced by eliminating the amino protecting group at $R^{13}$ of compound (IX) by a method known per se to give compound (X) and by N-alkylation using compound (XI).

Said N-alkylation can be generally carried out in an inert solvent. Examples of the inert solvent include acetone, dioxane, acetonitrile, chloroform, benzene, methylene chloride, ethylene chloride, tetrahydrofuran, ethyl acetate, N,N-dimethylfornamide, pyridine, water and mixed solvents thereof.

In addition, a base such as triethylamine, pyridine, 4-dimethylaminopyridine, potassium carbonate and the like can be used.

The reaction temperature is generally −10–100° C., preferably 0–60° C., and reaction time is generally from 30 min to 10 hr.

The compound (Ia) can be produced by eliminating the protecting group at $R^{16}$ of compound (XII) by a method known per se.

Production Method 2

The compound (XIII) can be produced by hydroxyalkylation of compound (III) [Adof H. Phlipp., et al., J. Med. Chem., 19(3), 391–395 (1976)], reducing, introducing an indoline skeleton, protecting amino, and halogenating hydroxy.

The compound (XIV) can be produced from compound (XIII) according to the method for obtaining compound (IX) from compound (VIII) as described in Production Method 1.

The compound (XV) can be produced from compound (XIV) by introducing nitro and reducing nitro by a method known per se.

The compound (XVI) can be produced from compound (XV) according to the method for obtaining compound (VII) from compound (IV) as described in Production Method 1.

The compound (Ib) can be produced from compound (XVI) via compound (XVII) and compound (XIII) according to the method for obtaining compound (Ia) from compound (IX) as described in Production Method 1.

Production Method 3

The compound (XIX) can be produced by oxidation of compound (X) by a method known per se (e.g., oxidation using chloranil, palladium-carbon and the like).

The compound (Ic) can be produced from compound (XIX) via compound (XX) according to the method for obtaining compound (Ia) from compound (X) as described in Production Method 1.

Production Method 4

The compound (XXI) can be produced by reducing 2,3-dihydroquinolin-4-one derivative [J. R Merchant, et al., J. Chem. Soc. Perkin I, 932–935 (1972)] using a reducing agent such as lithium aluminum hydride-aluminum chloride and the like.

The compound (XXIII) can be produced from compound (XXII) by protecting amino of compound (XXI) by a method known per se to give compound (XXII) and according to the method for obtaining compound (VIII) from compound (VII) as described in Production Method 1.

The compound (XXV) can be produced from compound (XXIII) via compound (XXIV) according to the method for obtaining compound (XII) from compound (VIII) via compound compound(IX) and compound (X) as described in Production Method 1.

The compound (XXVI) can be produced from compound (XXV) by introducing nitro and reducing nitro by a method known per se.

The compound (XXVII) can be produced from compound (XXVI) according to the method for obtaining compound (VII) from compound (IV) as described in Production Method 1.

The compound (Id) can be produced from compound (XXVII) according to the method for obtaining compound (Ia) from compound (XII) as described in Production Method 1.

Production Method 5

The compound (XXIX) can be produced from compound (XXVIII) (W. G. Gall, et al., J. Org. Chem., 20, 1538 (1955)] according to the method for obtaining compound (XII) from compound (X) as described in Production Method 1.

The compound (XXX) can be produced by converting halogen of compound (XXIX) to cyano by a method known per se, hydrolysis of cyano, and introducing a protecting group into the obtained carboxy.

The compound (XXXI) can be produced from compound (XXX) by reducing nitro of compound (XXX) by a method known per se, and according to the method for obtaining compound (VII) from compound (IV) as described in Production Method 1.

The compound (Ie) can be produced by eliminating the protecting group at $R^{20}$ of compound (XXXI) by a method known per se.

Production Method 6

The compound (XXXII) can be produced by converting amino of compound (IV) to hydroxy by a method known per se and introducing a protecting group into hydroxy.

The compound (XXXIII) can be produced from compound (XXXII) by introducing nitro and reducing nitro by a method known per se.

The compound (XXXIV) can be produced from compound (XXXIII) according to the method for obtaining compound (VII) from compound (IV) as described in Production Method 1.

The compound (XXXV) can be produced from compound (XXXIV) according to the method for obtaining compound (XII) from compound (IX) via compound (X) as described in Production Method 1.

The compound (If) can be produced by eliminating the protecting group at $R^{21}$ of compound (XXXV) by a method known per se.

Production Method 7

The compound (XXXVI) can be produced by alkylation of amino or by introducing a protecting group of amino of compound (IV) by a method known per se.

The compound (XXXVII) can be produced from compound (XXXVI) by introducing nitro and reducing nitro by a method known per se.

The compound (XXXVIII) can be produced from compound (XXXVII) according to the method for obtaining compound (VII) from compound (IV) as described in Production Method 1.

The compound (XXXIX) can be produced from compound (XXXVIII) according to the method for obtaining compound (XII) from compound (IX) via compound (X) as described in Production Method 1.

The compound (Ig) can be produced by eliminating the protecting group at $R^{22}$ of compound (XXXIX) by a method known per se.

The compound (I) of the present invention obtained by the above methods can be purified by a method conventionally known such as chromatography and recrystallization.

Said compound (I) can be converted to pharmaceutically acceptable salts by a method known per se.

A pharmaceutical composition containing the compound (I) of the present invention or a pharmaceutically acceptable salt thereof can further contain additives. Examples of the additive include excipients (e g., starch, lactose, sugar, calcium carbonate and calcium phosphate), binders (e.g., starch, gum arabic, carboxymethylcellulose, hydroxypropylcellulose and crystalline cellulose), lubricants (e.g., magnesium stearate and talc), and disintegrators (e.g., carboxymethyl-cellulose calcium and talc), and the like.

The above-mentioned ingredients are mixed and the mixture is prepared into oral preparations such as capsules, tablets, fine granules, granules and dry syrups, or parenteral preparations such as injections and suppositories by a method known per se.

While the dose of the compound (I) of the present invention and pharmaceutically acceptable salts thereof varies depending on administration targets, symptoms and others, when, for example, orally administered to adult patients of hypercholesterolemia, it is generally 0.1 mg–50 mg/kg body weight per dose which is administered about 1 to 3 time(s) a day.

The compound (I) of the present invention and pharmaceutically acceptable salts thereof exhibit superior ACAT inhibitory activity and lipoperoxidation inhibitory activity in mammals (e.g., human, cow, horse, dog, cat, rabbit, rat, mouse, hamster etc.) and are useful as ACAT inhibitors and lipoperoxidation inhibitors. In other words, they are useful for the prophylaxis and treatment of arteriosclerosis, hyperlipemia, arteriosclerosis in diabetes, cerebrovascular and cardiovascular ischemic diseases, and the like.

The present invention is described in more detail by way of Examples, to which the present invention is not limited.

EXAMPLE 1

N-(1-Octyl-5-hydroxymethyl-4,6-dimethylindolin-7-yl)-2,2-dimethylpropanamide (1) N-(1-Acetyl-5-chloromethyl-4,6-dimethylindolin-7-yl)-2,2-dimethylpropanamide (7.0 g) was dissolved in a mixed solvent (50 ml) of $CH_3CN/DMF=1/1$. Potassium acetate (12.0 g) was added and the mixture was stirred at 60° C. for 1 hr. $CH_3CN$ was evaporated under reduced pressure and AcOEt (200 ml) was added. After washing with water, the mixture was dried over anhydrous sodium sulfate, and AcOEt was evaporated under reduced pressure. The residue was purified by silica gel column chromatography (eluent: $CHCl_3/MeOH=1/0–10/1$) to give 7.5 g of N-(1-acetyl-5-acetoxymethyl-4,6-dimethylindolin-7-yl)-2,2-dimethylpropanamide.

$^1$H-NMR (CDCl$_3$) δ:
1.27 (9H, s, —C(CH$_3$)$_3$), 2.04 (3H, s, OCOCH$_3$), 2.23, 2.26, 2.30 (9H, s×3, —CH$_3$×2, >NCOCH$_3$), 3.00 (2H, br, Indoline C$_3$—H), 4.05 (2H, br, Indoline C$_2$—H), 5.20 (2H, s, —CH$_2$O—), 9.10 (1H, br, >NH).

(2) N-(1-Acetyl-5-acetoxymethyl-4,6-dimethylindolin-7-yl)-2,2-dimethylpropanamide (7.5 g) was dissolved in EtOH (70 ml) and a solution of NaOH (8.3 g) in water (20 ml) was added, which was followed by refluxing for 10 hr. EtoH was evaporated under reduced pressure and CHCl$_3$ (200 ml) was added. After washing with water, the mixture was dried over anhydrous sodium sulfate and CHCl$_3$ was evaporated under reduced pressure. The residue was purified by silica gel column chromatography (eluent: $CHCl_3/MeOH=1/0–10/1$) to give 3.0 g of N-(5-hydroxymethyl-4,6-dimethylindolin-7-yl)-2,2-dimethylpropanamide.

$^1$H-NMR (CDCl$_3$) δ:
1.35 (9H, s, —C(CH$_3$)$_3$), 2.23, 2.26 (6H, s×2, —CH$_3$×2), 2.99 (2H, t, J=8.5 Hz, Indoline C$_3$—H), 3.58 (2H, t, J=8.5 Hz, Indoline C$_2$—H), 4.65 (2H, s, —CH$_2$OH), 7.10 (2H, br, OH, >NH).

(3) N-(5-Hydroxymethyl-4,6-dimethylindolin-7-yl)-2,2-dimethylpropanamide (1.5 g) was dissolved in DMF (15 ml) and 1-iodooctane (2.6 g) and K$_2$CO$_3$ (1.5 g) were added, which was followed by stirring under a nitrogen atmosphere at 50° C. for 2 hr. AcOEt (200 ml) was added, and the mixture was washed with water and dried over anhydrous sodium sulfate. AcOEt was evaporated under reduced pressure. The residue was purified by silica gel column chromatography (eluent: $CHCl_3/MeOH=1/0–10/1$) to give 1.0 g of the title compound.

IR (Nujol) cm$^{-1}$: 1652, 1600, 1508.
$^1$H-NMR (CDCl$_3$) δ:
0.70–1.10 (3H, br, —(CH$_2$)$_7$CH$_3$), 1.10–1.70 (12H, m, —CH$_2$(CH$_2$)$_6$CH$_3$), 1.37 (9H, s, —C(CH$_3$)$_3$), 2.14, 2.22 (6H, s×2, —H$_3$×2), 2.87 (2H, t, J=8.5 Hz, Indoline C$_3$—H), 3.14 (2H, t, J=7.5 Hz, >NCH$_2$—), 3.42 (2H, t, J=8.5 Hz, Indoline C$_2$—H), 4.62 (2H, s, CH$_2$OH), 6.86 (2H, br, OH, >NH).

EXAMPLE 2

N-(1-Octyl-5-dimethylaminomethyl-4,6-dimethylindolin-7-yl)-2,2-dimethylpropanamide (1) N-(1-Acetyl-5-chloromethyl-4,6-dimethylindolin-7-yl)-2,2-dimethylpropanamide (2.0 g) was dissolved in $CHCl_3$ (40 ml) and $(CH_3)_2NH\cdot HCl$ (3.5 g) and $K_2CO_3$ (11.8 g) were added, which was followed by stirring at room temperature for 4 hr. $CHCl_3$ (300 ml) was added, and the mixture was washed successively with 2N-hydrochloric acid, 2N aqueous NaOH and saturated brine, and dried over anhydrous sodium sulfate. $CHCl_3$ was evaporated under reduced pressure. The residue was purified by silica gel column chromatography (eluent: $CHCl_3$/MeOH=10/1–1/1) to give 700 mg of N-(1-acetyl-5-dimethylaminomethyl-4,6-dimethylindolin-7-yl)-2,2-dimethylpropanamide.

$^1$H-NMR ($CDCl_3$) δ:
1.26 (9H, s —$C(CH_3)_3$), 2.12, 2.15 (6H, s×2, —$CH_3$×2), 2.24 (6H, s, —$N(CH_3)_2$), 2.31 (3H, s, >$NCOCH_3$), 3.00 (2H, br, Indoline $C_3$—H), 3.35 (2H, s, >$NCH_2$—), 4.15 (2H, br, Indoline $C_2$—H), 9.23 (1H, br, >NH).

(2) N-(1-Acetyl-5-dimethylaminomethyl-4,6-dimethylindolin-7-yl)-2,2-dimethylpropanamide (1.0 g) was dissolved in MeOH (10 ml) and a solution of NaOH (580 mg) in water (3 ml) was added, which was followed by stirring at 60° C. for 2 hr. MeOH was evaporated under reduced pressure and $CHCl_3$ (100 ml) was added. The mixture was washed with saturated brine and dried over anhydrous sodium sulfate. $CHCl_3$ was evaporated under reduced pressure to give 700 mg of N-(5-dimethylaminomethyl-4,6-dimethylindolin-7-yl)-2,2-dimethylpropanamide.

$^1$H-NMR ($CDCl_3$) δ:
1.30 (9H, s, —$C(CH_3)_3$), 2.19 (12H, s, —$CH_3$×2, —$N(CH_3)_2$), 3.00 (2H, t, J=8.5 Hz, Indoline $C_3$—H), 3.28 (2H, s, >$NCH_2$—), 3.55 (2H, t, J=8.5 Hz, Indoline $C_2$—H), 4.40 (1H, br, >NH), 7.20 (1H, br, >NH).

(3) N-(5-Dimethylaminomethyl-4,6-dimethylindolin-7-yl)-2,2-dimethylpropanamide (700 mg) was dissolved in DMF (7 ml) and Na (P=60%, 160 mg) was added under a nitrogen atmosphere at 5° C. After stirring at the same temperature for 30 min, 1-iodooctane (240 mg) was added, which was followed by stirring at 30° C. for 3 hr. AcOEt (200 ml) was added, and the mixture was washed with water and dried over anhydrous sodium sulfate. AcOEt was evaporated under reduced pressure. The residue was purified by silica gel column chromatography (eluent: $CHCl_3$/MeOH=10/1–3/1) to give 500 mg of the title compound.

IR (Nujol) cm$^{-1}$: 1654, 1600.
$^1$H-NMR ($CDCl_3$) δ:
0.70–1.10 (3H, br, —$(CH_2)_7CH_3$), 1.10–1.70 (12H, m, —$CH_2(CH_2)_6CH_3$), 1.33 (9H, s, —$(CH_3)_3$), 2.00, 2.09 (6H, s×2, —$CH_3$×2), 2.23 (6H, s, —$N(CH_3)_2$), 2.85 (2H, t, J=8.5 Hz, Indoline $C_3$—H), 3.18 (2H, br-t, >$NCH_2$—), 3.31 (2H, s, —$CH_2$N<), 3.38 (2H, t, J=8.5 Hz, Indoline $C_2$—H), 6.84 (1H, br, >NH).

EXAMPLE 3

N-(1-Octyl-5-ethoxycarbonylmethyl-4,6-dimethylindolin-7-yl)-2,2-dimethylpropanamide (1) 1-Acetyl-5-bromo-4,6-dimethyl-7-nitroindoline (30 g) was dissolved in a mixture (600 ml) of $CHCl_3$/MeOH=1/1 and 5% Pd-C (5.0 g) was added, which was followed by catalytic hydrogenation at 35° C. The precipitate was collected by filtration together with Pd-C, and dissolved in $CHCl_3$ (300 ml). The mixture was washed with saturated aqueous solution of sodium hydrogencarbonate. The solvent was evaporated under reduced pressure from the filtrate and $CHCl_3$ (300 ml) was added. The mixture was washed with saturated aqueous solution of sodium hydrogencarbonate and combined with the layer of above-mentioned $CHCl_3$. The combined $CHCl_3$ layer was washed with saturated brine and dried over anhydrous sodium sulfate. $CHCl_3$ was evaporated under reduced pressure and the residue was dissolved in $CHCl_3$ (150 ml). Thereto were successively added at 10° C. pivaloyl chloride (11.7 g) and $Et_3N$ (10.8 g). The mixture was stirred at room temperature for 1 hr and $CHCl_3$ (200 ml) was added. The mixture was washed successively with 5% aqueous citric acid and water, and dried over anhydrous sodium sulfate. $CHCl_3$ was evaporated under reduced pressure and the obtained crude residue was washed with cool $Et_2O$ (100 ml) to give 21 g of N-(1-acetyl-4,6-dimethylindolin-7-yl)-2,2-dimethylpropanamide.

IR (Nujol)cm$^{-1}$: 1676, 1639, 1581.
$^1$H-NMR ($CDCl_3$) δ:
1.24 (9H, s, —$C(CH_3)_3$), 2.17 (6H, s, —$CH_3$×2), 2.30 (3H, s, >$NCOCH_3$), 2.99 (2H, t, J=8.5 Hz, Indoline $C_3$—H), 4.10 (2H, t, J=8.5 Hz, Indoline $C_2$—H), 6.87 (1H, s, Indoline $C_5$—H), 9.10 (1H, br, >NH).

(2) N-(1-Acetyl-4,6-dimethylindolin-7-yl)-2,2-dimethylpropanamide (20.0 g) was dissolved in conc. hydrochloric acid (100 ml), and 35% formalin (8.5 g) and zinc chloride (1.8 g) were added. The mixture was stirred at 40–50° C. for 2 hr while blowing hydrogen chloride therein. The reaction mixture was poured into ice water and extracted with $CHCl_3$ (400 ml). The $CHCl_3$ layer was washed twice with saturated brine and dried over anhydrous sodium sulfate. $CHCl_3$ was evaporated under reduced pressure to give 21 g of N-(1-acetyl-5-chlorooethyl-4,6-dimethylindolin-7-yl)-2,2-dimethylpropanamide.

IR (Nujol)cm$^{-1}$: 1679, 1645, 1587.
$^1$H-NMR ($CDCl_3$) δ:
1.27 (9H, s, —$C(CH_3)_3$), 2.25 (3H, s, —$CH_3$), 2.30 (6H, s, —$CH_3$, >$NCOCH_3$), 3.00 (2H, br, Indoline $C_3$—H), 4.05 (2H, br, Indoline $C_2$—H), 4.68 (2H, s, —$CH_2Cl$), 9.16 (1H, br, >NH).

(3) N-(1-Acetyl-5-chloromethyl-4,6-dimethylindolin-7-yl)-2,2-dimethylpropanamide (21 g) was suspended in $CH_3CN$ (150 ml), and NaCN (8.1 g) and 18-crown-6 (870 mg) were added, which was followed by refluxing for 15 hr. $CH_3CN$ was evaporated under reduced pressure and $CHCl_3$ (300 ml) was added. The mixture was washed with water and dried over anhydrous sodium sulfate. $CHCl_3$ was evaporated under reduced pressure. The obtained residue was washed with boiling MeOH to give 15.5 g of N-(1-acetyl-5-cyanomethyl-4,6-dimethylindolin-7-yl)-2,2-dimethylpropanamide.

IR (Nujol)cm$^{-1}$: 2232, 1678, 1639.
$^1$H-NMR ($CDCl_3$) δ:
1.27 (9H, s, —$C(CH_3)_3$), 2.26, 2.30, 2.40 (9H, s×3, $CH_3$×2, >$NCOCH_3$), 3.00 (2H, br, Indoline $C_3$—H), 3.66 (2H, s, —$CH_2CN$), 4.05 (2H, br, Indoline $C_2$—H), 9.21 (1H, br, >NH).

(4) N-(1-Acetyl-5-cyanomethyl-4,6-dimethylindolin-7-yl)-2,2-dimethylpropanamide (5.0 g) was suspended in n-PrOH (25 ml) and a solution of NaOH (9.6 g) in water (10 ml) was added, which was followed by stirring at 90° C. for 8 hr in an autoclave under a nitrogen atmosphere.

The aqueous layer was separated, and the organic layer was neutralized with 2N-hydrochloric acid. The solvent was evaporated under reduced pressure. The residue was suspended in EtOH (200 ml), and 10N HCl-EtOH (7.2 ml) was added, which was followed by refluxing for 1 hr. EtOH was evaporated under reduced pressure, and the mixture was neutralized with saturated aqueous solution of sodium hydrogencarbonate and extracted with AcOEt (200 ml). The AcOEt layer was washed with water and dried over anhydrous sodium sulfate. AcOEt was evaporated under reduced pressure and the residue was purified by silica gel column chromatography (eluent: CHCl$_3$/MeOH=1/0–20/1) to give 3.0 g of N-(5-ethoxycarbonylmethyl-4,6-dimethylindolin-7-yl)-2,2-dimethylpropanamide.

IR (Nujol)cm$^{-1}$: 1732, 1654.

$^1$H-NMR (CDCl$_3$) δ:

1.34 (9H, s, —C(CH$_3$)$_3$), 2.14, 2.18 (6H, s×2, —CH$_3$×2), 2.99 (2H, t, J=8.5 Hz, Indoline C$_3$—H), 3.56 (2H, t, J=8.5 Hz, Indoline C$_2$—H), 3.60 (2H, s, —CH$_2$CO$_2$—), 4.11 (2H, q, J=7.8 Hz, —CH$_2$CH$_3$), 4.20 (1H, br, >NH), 7.00 (1H, br, >NH).

(5) N-(5-Ethoxycarbonylmethyl-4,6-dimethylindolin-7-yl)-2,2-dimethylpropanamide (3.5 g) was dissolved in DMF (15 ml), and 1-iodooctane (5.0 g) and K$_2$CO$_3$ (2.9 g) were added, which was followed by stirring under a nitrogen atmosphere at 50° C. for 2 hr. AcOEt (200 ml) was added, and the mixture was washed with water and dried over anhydrous sodium sulfate. AcOEt was evaporated under reduced pressure. The residue was purified by silica gel column chromatography (eluent: CHCl$_3$/MeOH=1/0 –50/1) to give 3.5 g of the title compound.

IR (Neat) cm$^{-1}$: 1732, 1654, 1600.

$^1$H-NMR (CDCl$_3$) δ:

0.70–1.10 (3H, br, —(CH$_2$)$_7$CH$_3$), 1.10–1.70 (15H, m, —CH$_2$CH$_3$, —CH$_2$(CH$_2$)$_6$CH$_3$), 1.33 (9H, s, —C(CH$_3$)$_3$), 2.04, 2.13 (6H, s×2, —CH$_3$×2), 2.87 (2H, t, J=8.5 Hz, Indoline C$_3$—H), 3.12 (2H, t, J=7.5 Hz, >NCH$_2$—), 3.39 (2H, t, J=8.5 Hz, Indoline C$_2$—H), 3.58 (2H, s, —CH$_2$CO$_2$—), 4.12 (2H, q, J=7.5 Hz, —CH$_2$CH$_3$), 6.79 (1H, br, >NH).

EXAMPLE 4

N-(1-Octyl-5-carboxymethyl-4,6-dimethylindolin-7-yl)-2,2-dimethylpropanamide N-(1-Octyl-5-ethoxycarbonylmethyl-4,6-dimethylindolin-7-yl)-2,2-dimethylpropanamide (3.5 g) was dissolved in EtOH (50 ml) and a solution of NaOH (1.6 g) in water (20 ml) was added, which was followed by stirring at 60° C. for 1 hr. EtOH was evaporated under reduced pressure. The residue was dissolved in water (20 ml) and the mixture was washed with AcOEt (20 ml). The aqueous layer was neutralized with 2N-hydrochloric acid and extracted with AcOEt (50 ml). The AcOEt layer was washed with saturated brine and dried over anhydrous sodium sulfate. AcOEt was evaporated under reduced pressure to give 2.4 g of the title compound.

IR (Nujol)cm$^{-1}$: 1732, 1651, 1600.

$^1$H-NMR (CDCl$_3$) δ:

0.70–1.10 (3H, br, —(CH$_2$)$_7$CH$_3$), 1.10–1.70 (12H, m, —CH$_2$(CH$_2$)$_6$CH$_3$), 1.33 (9H, s, —C(CH$_3$)$_3$), 2.01, 2.15 (6H, s×2, —CH$_3$×2), 2.70–3.20 (4H, m, Indoline C$_3$—H, >NCH$_2$—), 3.41 (2H, t, J=8.5 Hz, Indoline C$_2$—H), 3.56 (2H, s, —CH$_2$CO$_2$H), 7.60 (1H, br, >NH), 7.90 (1H, br, —CO$_2$H).

EXAMPLE 5

N-(1-Octyl-5-carboxymethyl-4,6-dimethylindolin-7-yl)-2,2-dimethylpropanamide.hydrochloride N-(1-Octyl-5-ethoxycarbonylmethyl-4,6-dimethylindolin-7-yl)-2,2-dimethylpropanamide (3.5 g) was dissolved in EtOH (50 ml) and a solution of NaOH (1.6 g) in water (20 ml) was added, which was followed by stirring at 60° C. for 1 hr. EtOH was evaporated under reduced pressure. The residue was dissolved in water (20 ml) and the mixture was washed with AcOEt (20 ml). The aqueous layer was adjusted to pH 1–2 with hydrochloric acid and extracted with AcOEt (50 ml). The AcOEt layer was washed with saturated brine and dried over anhydrous sodium sulfate. AcOEt was evaporated under reduced pressure to give 2.0 g of the title compound.

IR (Nujol)cm$^{-1}$: 1722, 1654.

$^1$H-NMR (CDCl$_3$) δ:

0.70–1.10 (3H, br, —(CH$_2$)$_7$CH$_3$), 1.10–1.70 (12H, m, —CH$_2$(CH$_2$)$_6$CH$_3$), 1.39 (9H, s, —C(CH$_3$)$_3$), 2.06, 2.26 (6H, s×2, —CH$_3$×2), 2.90–3.30 (4H, m, Indoline C$_3$—H, >NCH$_2$—), 3.50–3.90 (2H, br-t, Indoline C$_2$—H), 3.72 (2H, s, —CH$_2$CO$_2$H), 6.00–7.00 (1H, br, HCl), 9.05 (2H, br, >NH, —CO$_2$H).

EXAMPLE 6

N-(1-Octyl-5-carboxymethyl-4,6-dimethylindolin-7-yl)-2,2-dimethylpropanamide.sulfate N-(1-Octyl-5-ethoxycarbonylmethyl-4,6-dimethylindolin-7-yl)-2,2-dimethylpropanamide (4.0 g) was dissolved in EtOH (57 ml) and a solution of NaOH (1.8 g) in water (23 ml) was added, which was followed by stirring at 60° C. for 1 hr. EtOH was evaporated under reduced pressure. The residue was dissolved in water (30 ml) and the mixture was washed with AcOEt (30 ml). The aqueous layer was adjusted to pH 1–2 with sulfuric acid and extracted with AcOEt (50 ml). The AcOEt layer was washed with saturated brine and dried over anhydrous sodium sulfate. AcOEt was evaporated under reduced pressure to give 2.5 g of the title compound.

IR (Nujol)cm$^{-1}$: 1718, 1654, 1637.

$^1$H-NMR (CDCl$_3$) δ:

0.70–1.10 (3H, br, —(CH$_2$)$_7$CH$_3$), 1.10–1.70 (12H, m, —CH$_2$(CH$_2$)$_6$CH$_3$), 1.33 (9H, s, —C(CH$_3$)$_3$), 2.02, 2.16 (6H, s×2, —CH$_3$×2), 2.80–3.30 (4H, m, Indoline C$_3$—H, >NCH$_2$—), 3.30–3.70 (2H, br-t, Indoline C$_2$—H), 3.59 (2H, s, CH$_2$CO$_2$H), 6.00–7.00 (2H, br, H$_2$SO$_4$), 7.20 (1H, br, —CO$_2$H), 8.30 (1H, br, >NH).

EXAMPLE 7

N-(1-Octyl-5-carboxymethyl-4,6-dimethylindolin-7-yl)-2,2-dimethylpropanamide.nitrate N-(1-Octyl-5-ethoxycarbonylmethyl-4,6-dimethylindolin-7-yl)-2,2-dimethylpropanamide (3.0 g) was dissolved in EtOH (42 ml) and a solution of NaOH (1.4 g) in water (17 ml) was added, which was followed by stirring at 60° C. for 1 hr. EtOH was evaporated under reduced pressure. The residue was dissolved in water (20 ml) and the mixture was washed with AcOEt (20 ml). The aqueous layer was adjusted to pH 1–2 with nitric acid and extracted with AcOEt (50 ml). The AcOEt layer was washed with saturated brine and dried over anhydrous sodium sulfate. AcOEt was evaporated under reduced pressure to give 2.0 g of the title compound.

IR (Nujol)cm$^{-1}$: 1724, 1654

$^1$H-NMR (CDCl$_3$) δ:

0.70–1.10 (3H, br, —(CH$_2$)$_7$CH$_3$), 1.10–1.70 (12H, m, —CH$_2$(CH$_2$)$_6$CH$_3$), 1.33 (9H, s, —(CH$_3$)$_3$), 2.02, 2.21 (6H, s×2, CH$_3$×2), 2.80–3.30 (4H, m, Indoline C$_3$—H, >NCH$_2$—), 3.50–3.80 (2H, br-t, Indoline C$_2$—H), 3.64 (2H, s, CH$_2$CO$_2$H), 6.00–7.00 (1H, br, HNO$_3$), 9.03 (2H, br, >NH, —CO$_2$H).

EXAMPLE 8

N-(1-Octyl-5-carboxymethyl-4,6-dimethylindolin-7-yl)-2,2-dimethylpropanamide.sodium Salt N-(1-Octyl-5-ethoxycarbonylmethyl-4,6-dimethylindolin-7-yl)-2,2-dimethylpropanamide (3.5 g) was dissolved in EtOH (50 ml) and a solution of NaOH (1.6 g) in water (20 ml) was added, which was followed by stirring at 60° C. for 1 hr. EtOH was evaporated under reduced pressure. The residue was dissolved in water (20 ml) and the mixture was adsorbed onto DIAION® HP-21 (70 ml). After washing with water, the mixture was eluted with 50% aqueous methanol. The objective fraction was concentrated under reduced pressure. The residue was freeze-dried to give 1.0 g of the title-compound.

IR (Nujol)cm$^{-1}$: 1630, 1605.
$^1$H-NMR (CDCl$_3$) δ:
0.70–1.10 (3H, br, —(CH$_2$)$_7$CH$_3$), 1.10–1.70 (12H, m, —CH$_2$(CH$_2$)$_6$CH$_3$), 1.38 (9H, s, —C(CH$_3$)$_3$), 1.93, 2.08 (6H, s×2, —CH$_3$×2), 2.70–3.20 (4H, m, Indoline C$_3$—H, >NCH$_2$—), 3.30–3.40 (2H, br-t, Indoline C$_2$—H), 3.15 (2H, s, —CH$_2$CO$_2$Na), 8.54 (1H, br, >NH).

EXAMPLE 9

N-[(1-Octyl-3-(2-hydroxyethyl)-4,6-dimethylindolin-7-yl)]-2,2-dimethylpropanamide (1) 4,6-Dimethylindole (130 g) was dissolved in Et$_2$O (130 ml), and oxalyl chloride (23.0 g) was dropwise added at 0° C. The mixture was stirred at room temperature for 5 hr, and Et$_2$O was evaporated under reduced pressure. EtOH (200 ml) was added to the residue and the mixture was stirred at room temperature for 15 hr. EtOH was evaporated under reduced pressure. The residue was dissolved in CHCl$_3$ (200 ml). After washing with water, the mixture was dried over anhydrous sodium sulfate. CHCl$_3$ was evaporated under reduced pressure. The obtained residue was added to a suspension of LiAlH$_4$ (17.0 g) in Et$_2$O (200 ml), which was followed by refluxing for 2 hr. The reaction mixture was poured into ice water and extracted with AcOEt (200 ml). The AcOEt layer was washed with water and dried over anhydrous sodium sulfate. AcOEt was evaporated under reduced pressure. The residue was purified by silica gel column chromatography (eluent: CHCl$_3$/MeOH=50/1–10/1) to give 13.0 g of 3-(2-hydroxyethyl)-4,6-dimethylindole.

IR (Nujol)cm$^{-1}$: 1456, 1377.
$^1$H-NMR (CDCl$_3$) δ:
2.39, 2.63 (6H, s×2, —CH$_3$×2), 3.13 (2H, t, J=7.0 Hz, —CH$_2$CH$_2$OH), 3.86 (2H, t, J=7.0 Hz, —CH$_2$CH$_2$OH), 6.69 (1H, s, Indole C$_5$—H), 6.91 (2H, m, Indole C$_2$—H, C$_7$—H), 6.92 (1H, br, —OH), 7.90 (1H, br, >NH).

(2) 3-(2-Hydroxyethyl)-4,6-dimethylindole (13.0 g) was dissolved in AcOH (100 ml) and NaBH$_3$CN (8.7 g) was added by portions under ice-cooling. After stirring at the same temperature for 1 hr, the reaction mixture was poured into ice water and neutralized with aqueous NaOH. The mixture was extracted with CHCl$_3$ (200 ml). The CHCl$_3$ layer was washed with water and dried over anhydrous sodium sulfate. CHCl$_3$ was evaporated under reduced pressure. The residue was dissolved in benzene (100 ml), and Ac$_2$O (15 g) and Et$_3$N (8.3 g) were added, which was followed by stirring at room temperature for 1 hr. AcOEt (200 ml) was added and the mixture was washed successively with saturated aqueous solution of sodium hydrogencarbonate, 5% aqueous citric acid and saturated brine, and dried over anhydrous sodium sulfate. The solvent was evaporated under reduced pressure. The residue was purified by silica gel column chromatography (eluent: CHCl$_3$/MeOH=50/1–10/1) to give 13.0 g of 1-acetyl-3-(2-acetoxyethyl)-4,6-dimethylindoline.

IR (Nujol)cm$^{-1}$: 1652, 1460.
$^1$H-NMR (CDCl$_3$) δ:
1.60–2.20 (2H, m, —CH$_2$CH$_2$O—), 2.04 (3H, s, —OCOCH$_3$), 2.24 (3H, s, >NCOCH$_3$), 2.24, 2.30 (6H, s×2, —CH$_3$×2), 3.34 (1H, m, Indoline C$_3$—H), 3.94 (2H, m, Indoline C$_2$—H), 4.12 (2H, t, J=7.1 Hz, —CH$_2$CH$_2$O—), 6.67 (1H, s, Indoline C$_5$—H), 7.90 (1H, s, Indoline C$_7$—H).

(3) 1-Acetyl-3-(2-acetoxyethyl)-4,6-dimethylindoline (2.0 g) was dissolved in AcOH (40 ml) and Br$_2$ (1.9 g) was added, which was followed by stirring at room temperature for 30 min. The reaction mixture was poured into ice water and precipitate was collected by filtration. The precipitate was dissolved in CHCl$_3$, and the mixture was washed with water and dried over anhydrous sodium sulfate. CHCl$_3$ was evaporated under reduced pressure. The residue was purified by silica gel column chromatography (eluent: CHCl$_3$/MeOH=50/1–10/1) to give 2.7 g of crude crystals of 1-acetyl-3-(2-acetoxyethyl)-5-bromo-4,6-dimethylindoline. The crude crystals were added by portions to a mixture of nitric acid (0.47 ml), AcOH (10 ml) and conc. hydrochloric acid (10 ml) under ice-cooling, and the mixture was stirred at the same temperature for 4 hr. The reaction mixture was poured into ice water and precipitate was collected by filtration. The precipitate was dissolved in CHCl$_3$. After washing with water, the mixture was dried over anhydrous sodium sulfate and CHCl$_3$ was evaporated under reduced pressure. The residue was purified by silica gel column chromatography (eluent: CHCl$_3$/MeOH=50/1–10/1) to give 1.4 g of 1-acetyl-3-(2-acetoxyethyl)-5-bromo-4,6-dimethyl-7-nitroindoline.

$^1$H-NMR (DMSO-d$_6$) δ:
1.60–2.20 (2H, m, —CH$_2$CH$_2$O—), 1.99 (3H, s, —OCOCH$_3$), 2.21 (3H, s, >NCOCH$_3$), 2.38 (6H, s, —CH$_3$×2), 3.40 (1H, m, Indoline C$_3$—H), 4.11 (2H, t, J=7.0 Hz, —CH$_2$CH$_2$O—), 4.14 (2H, d, J=8.5 Hz, Indoline C$_2$—H).

(4) 1-Acetyl-3-(2-acetoxyethyl)-5-bromo-4,6-dimethyl-7-nitroindoline (1.4 g) was dissolved in benzene (20 ml) and 5% Pd-C (500 mg) was added, which was followed by catalytic hydrogenation at room temperature under atmospheric pressure. Pd-C was filtered off and benzene was evaporated under reduced pressure. The residue was dissolved in CHCl$_3$ (50 ml) and the mixture was washed successively with saturated aqueous solution of sodium hydrogencarbonate and saturated brine, and dried over anhydrous sodium sulfate. Pivaloyl chloride (440 mg) and Et$_3$N (448 mg) were added to the obtained solution and the mixture was stirred at room temperature for 30 min. The mixture was washed successively with 5% aqueous citric acid and saturated brine, and dried over anhydrous sodium sulfate. CHCl$_3$ was evaporated under reduced pressure. The residue was purified by silica gel column chromatography (eluent: CHCl$_3$/MeOH=50/1–10/1) to give 1.0 g of N-[1-acetyl-3-(2-acetoxyethyl)-4,6-dimethylindolin-7-yl]-2,2-dimethylpropanamide.

IR (Nujol)cm$^{-1}$: 1730, 1649.
$^1$H-NMR (CDCl$_3$) δ:
1.27 (9H, s, —C(CH$_3$)$_3$), 1.60–2.20 (2H, m, —CH$_2$CH$_2$O—), 2.06 (3H, s, —OCOCH$_3$), 2.17, 2.22 (6H, s, —CH$_3$×2), 2.30 (3H, s, >NCOCH$_3$), 3.10 (1H, m, Indoline C$_3$—H), 4.03 (2H, d, J=8.5 Hz, Indoline C$_2$—H), 4.14 (1H, t, J=7.0 Hz, —CH$_2$CH$_2$O—), 6.88 (1H, s, Indoline C$_5$—H), 9.00 (1H, br, >NH)

(5) N-[1-Acetyl-3-(2-acetoxyethyl)-4,6-dimethylindolin-7-yl]-2,2-dimethylpropanamide (4.0 g) was dissolved in EtOH (40 ml) and a solution of NaOH (2.2 g) in water (10 ml) was added, which was followed by stirring at 60° C. for 10 hr. EtOH was evaporated under reduced pressure, and CHCl$_3$ (100 ml) was added. After washing with water, the mixture was dried over anhydrous sodium sulfate, and CHCl$_3$ was evaporated under reduced pressure. The residue was purified by silica gel column chromatography (eluent: CHCl$_3$/MeOH=50/1–10/1) to give 1.6 g of N-[3-(2-hydroxyethyl)-4,6-dimethylindolin-7-yl)-2,2-dimethylpropanamide.

$^1$H-NMR (CDCl$_3$) δ:
1.34 (9H, s, —C(CH$_3$)$_3$), 1.60–2.20 (2H, m, —CH$_2$CH$_2$OH), 2.17, 2.19 (6H, s×2, —CH$_3$×2), 3.20–3.80 (7H, m, Indoline C$_2$—H, C$_3$—H, >NH, —CH$_2$CH$_2$OH), 6.45 (1H, s, Indoline C$_5$—H), 7.20 (1H, br, —CONH—).

(6) N-[3-(2-Hydroxyethyl)-4,6-dimethylindolin-7-yl]-2,2-dimethylpropanamide (1.6 g) was dissolved in DMF (15 ml) and 1-iodooctane (3.9 g) and K$_2$CO$_3$ (2.3 g) were added, which was followed by stirring at 70° C. for 10 hr. AcOEt (200 ml) was added, and the mixture was washed with water and dried over anhydrous sodium sulfate. AcOEt was evaporated under reduced pressure. The residue was purified by silica gel column chromatography (eluent: benzene/AcOEt=5/1–1/2) to give 300 mg of the title compound.

IR (Nujol)cm$^{-1}$: 1645, 1600.
$^1$H-NMR (CDCl$_3$) δ:
0.70–1.00 (3H, br-t, —(CH$_2$)$_6$CH$_3$), 1.33 (9H, s, —(CH$_3$)$_3$), 1.00–2.00 (14H, m, —(CH$_2$)$_6$CH$_3$, —CH$_2$CH$_2$OH), 2.07, 2.16 (6H, s×2, —CH$_3$×2), 2.60–3.60 (8H, m, Indoline C$_2$—H, C$_3$—H, >NCH$_2$—, —CH$_2$OH), 6.44 (1H, s, Indoline C$_5$—H), 6.78 (1H, br, —CONH—).

EXAMPLE 10

N-[(1-Octyl-3-(2-methoxycarbonylethyl)-4,6-dimethylindolin-7-yl)]-2,2-dimethylpropanamide (1) 1-Acetyl-3-(2-acetoxyethyl)-4,6-dimethylindoline (2.0 g) was dissolved in a mixture of CHCl$_3$/MeOH=1/1 (25 ml), and a solution of NaOH (1.5 g) in water (5 ml) was added, which was followed by stirring at room temperature for 1 hr. The solvent was evaporated under reduced pressure. CHCl$_3$ (100 ml) was added, and the mixture was washed with water and dried over anhydrous sodium sulfate. CHCl$_3$ was evaporated under reduced pressure. The residue was purified by silica gel column chromatography (eluent: CHCl$_3$/MeOH=50/1–10/1) to give 1.2 g of 1-acetyl-3-(2-hydroxyethyl)-4,6-dimethylindoline.

$^1$H-NMR (CDCl$_3$) δ:
1.60–2.00 (3H, m, —CH$_2$CH$_2$OH), 2.26, 2.30, 2.39 (9H, s×3, —CH$_3$×2, >NCOCH$_3$), 3.50 (1H, m, Indoline C$_3$—H), 3.77 (2H, t, J=7.0 Hz, —CH$_2$CH$_2$OH), 3.97 (2H, m, Indoline C$_2$—H), 6.67 (1H, s, Indoline C$_5$—H), 7.89 (1H, s, Indoline C$_7$—H).

(2) 1-Acetyl-3-(2-hydroxyethyl)-4,6-dimethylindoline (7.0 g) and CBr$_4$ (9.9 g) were dissolved in CH$_3$CN (70 ml), and Ph$_3$P (9.4 g) was added, which was followed by stirring at room temperature for 30 min. CH$_3$CN was evaporated under reduced pressure. AcOEt (100 ml) was added, and the mixture was washed with water and dried over anhydrous sodium sulfate. AcOEt was evaporated under reduced pressure. The residue was purified by silica gel column chromatography (eluent: benzene/AcOEt=50/1–10/1) to give 5.4 g of 1-acetyl-3-(2-bromoethyl)-4,6-dimethylindoline.

IR (Nujol)cm$^{-1}$: 1650, 1460.
$^1$H-NMR (CDCl$_3$) δ:
1.80–2.20 (2H, m, —CH$_2$CH$_2$Br), 2.23, 2.26, 2.30 (9H, s×3, —CH$_3$×2, >NCOCH$_3$), 3.42 (2H, t, J=7.0 Hz, —CH$_2$CH$_2$Br), 3.20–3.60 (1H, m, Indoline C$_3$—H), 4.00 (2H, m, Indoline C$_2$—H), 6.68 (1H, s, Indoline C$_5$—H), 7.89 (1H, s, Indoline C$_7$—H).

(3) 1-Acetyl-3-(2-bromoethyl)-4,6-dimethylindoline (5.4 g), NaCN (3.7 g) and 18-crown-6 (480 mg) were suspended in CH$_3$CN (50 ml), and the suspension was refluxed for 15 hr. CH$_3$CN was evaporated under reduced pressure. CHCl$_3$ (100 ml) was added, and the mixture was washed with water and dried over anhydrous sodium sulfate. CHCl$_3$ was evaporated under reduced pressure. The residue was purified by silica gel column chromatography (eluent: CHCl$_3$/MeOH=50/1–10/1) to give 4.5 g of 1-acetyl-3-(2-cyanoethyl)-4,6-dimethylindoline.

IR (Nujol)cm$^{-1}$: 2364, 1647.
$^1$H-NMR (CDCl$_3$) δ:
1.70–2.20 (2H, m, —CH$_2$CH$_2$CN), 2.26, 2.31 (9H, s×3, —CH$_3$×2, >NCOCH$_3$), 2.20–2.40 (2H, m, —CH$_2$CH$_2$CN), 3.44 (1H, m, Indoline C$_3$—H), 3.70–4.20 (2H, m, Indoline C$_2$—H), 6.69 (1H, s, Indoline C$_5$—H), 7.90 (1H, s, Indoline C$_7$—H).

(4) 1-Acetyl-3-(2-cyanoethyl)-4,6-dimethylindoline (4.5 g) was dissolved in EtOH (150 ml), and a solution of KOH (10.4 g) in water (50 ml) was added, which was followed by refluxing for 15 hr. EtOH was evaporated under reduced pressure, and the aqueous layer was adjusted to weak acidic with 6N hydrochloric acid and extracted with CHCl$_3$ (100 ml). The CHCl$_3$ layer was washed with water and dried over anhydrous sodium sulfate. CHCl$_3$ was evaporated under reduced pressure. The residue was dissolved in CHCl$_3$ (20 ml) and Ac$_2$O (1.9 g) was added, which was followed by stirring at room temperature for 1 hr. CHCl$_3$ (100 ml) was added, and the mixture was washed with water and dried over anhydrous sodium sulfate. CHCl$_3$ was evaporated under reduced pressure. The residue was purified by silica gel column chromatography (eluent: CHCl$_3$/MeOH=50/1–10/1) to give 3.4 g of 1-acetyl-3-(2-carboxyethyl)-4,6-dimethylindoline.

$^1$H-NMR (CDCl$_3$) δ:
1.60–2.20 (2H, m, —CH$_2$CH$_2$CO$_2$H), 2.26, 2.29 (9H, s×3, —CH$_3$×2, >NCOCH$_3$), 2.20–2.40 (2H, m, —CH$_2$CH$_2$CO$_2$H), 3.37 (1H, m, Indoline C$_3$—H), 3.80–4.10 (2H, m, Indoline C$_2$—H), 6.68 (1H, s, Indoline C$_5$—H), 7.50 (1H, br, —CO$_2$H), 7.88 (1H, s, Indoline C$_7$—H).

(5) 1-Acetyl-3-(2-carboxyethyl)-4,6-dimethylindoline (3.4 g) was dissolved in EtOH (50 ml) and 10N HCl-EtOH (3.9 ml) was added, which was followed by refluxing for 30 min. EtOH was evaporated under reduced pressure and AcOEt (100 ml) was added. After washing with water, the mixture was dried over anhydrous sodium sulfate. AcOEt was evaporated under reduced pressure. The residue was purified by silica gel column chromatography (eluent: CHCl$_3$/MeOH=50/1–10/1) to give 3.3 g of 1-acetyl-3-(2-ethoxycarbonylethyl)-4,6-dimethylindoline.

$^1$H-NMR (CDCl$_3$) δ:
1.24 (3H, t, J=7.1 Hz, —CH$_2$CH$_3$), 1.60–2.20 (2H, m, —CH$_2$CH$_2$CO$_2$—), 2.22, 2.27, 2.30 (9H, s×3, —CH$_3$×2, >NCOCH$_3$), 2.00, 2.20 (2H, m, —CH$_2$CH$_2$CO$_2$—), 3.10–3.30 (1H, m, Indoline C$_3$—H), 3.90 (2H, m, Indoline C$_2$—H), 4.10 (2H, q, J=7.1 Hz, —CH$_2$CH$_3$), 6.76 (1H, s, Indoline C$_5$—H), 7.90 (1H, s, Indoline C$_7$—H).

(6) 1-Acetyl-3-(2-ethoxycarbonylethyl)-4,6-dimethylindoline (3.3 g) was dissolved in AcOH (30 ml)

and Br$_2$ (0.93 ml) was added, which was followed by stirring for 30 min. The reaction mixture was poured into ice water and precipitated crude crystals were collected by filtration. The obtained crystals were dissolved in CHCl$_3$ (100 ml). After washing with water, the mixture was dried over anhydrous sodium sulfate. CHCl$_3$ was evaporated under reduced pressure. The residue was purified by silica gel column chromatography (eluent: CHCl$_3$/MeOH=50/1–10/1) to give 3.0 g of 1-acetyl-5-bromo-3-(2-ethoxycarbonylethyl)-4,6-dimethylindoline.

IR (Nujol)cm$^{-1}$: 1729, 1641.

$^1$H-NMR (CDCl$_3$) δ:

1.24 (3H, t, J=7.1 Hz, —CH$_2$CH$_3$), 1.60–2.20 (2H, m, —CH$_2$CH$_2$CO$_2$—), 2.00–2.20 (2H, m, —CH$_2$CH$_2$CO$_2$—), 2.21 (3H, s, >NCOCH$_3$), 2.36, 2.39 (6H, s×2, —CH$_3$×2), 3.10–3.60 (1H, m, Indoline C$_3$—H), 3.90 (2H, m, Indoline C$_2$—H), 4.10 (2H, q, J=7.1 Hz, —CH$_2$CH$_3$), 8.08 (1H, s, Indoline C$_7$—H).

(7) To a mixture of AcOH (10 ml), conc. sulfuric acid (10 ml) and nitric acid (0.55 ml) was added by portions 1-acetyl-5-bromo-3-(2-ethoxycarbonylethyl)-4,6-dimethylindoline (3.0 g) at 0° C., and the mixture was stirred at the same temperature for 5 hr. The reaction mixture was poured into ice water and extracted with CHCl$_3$ (100 ml). After washing with water, the mixture was dried over anhydrous sodium sulfate. CHCl$_3$ was evaporated under reduced pressure. The residue was purified by silica gel column chromatography (eluent: CHCl$_3$/MeOH=50/1–10/1) to give 2.7 g of 1-acetyl-5-bromo-3-(2-ethoxycarbonylethyl)-4,6-dimethyl-7-nitroindoline.

$^1$H-NMR (CDCl$_3$) δ:

1.26 (3H, t, J=7.1 Hz, —CH$_2$CH$_3$), 1.60–2.20 (2H, m, —CH$_2$CH$_2$CO$_2$—), 2.00–2.20 (2H, m, —CH$_2$CH$_2$CO$_2$—), 2.23 (3H, s, >NCOCH$_3$), 2.44, 2.47 (6H, s×2, —CH$_3$×2), 3.10–3.60 (1H, m, Indoline C$_3$—H), 4.00 (2H, m, Indoline C$_2$—H), 4.10 (2H, q, J=7.1 Hz, —CH$_2$CH$_3$).

(8) 1-Acetyl-5-bromo-3-(2-ethoxycarbonylethyl)-4,6-dimethyl-7-nitroindoline (2.7 g) was dissolved in benzene (100 ml), and 5% Pd-C (500 mg) was added, which was followed by catalytic hydrogenation at room temperature under atmospheric pressure. PdC was filtered off and benzene was evaporated under reduced pressure. CHCl$_3$ (100 ml) was added to the residue, and the mixture was washed successively with saturated aqueous solution of sodium hydrogencarbonate and saturated brine and dried over anhydrous sodium sulfate. CHCl$_3$ was evaporated under reduced pressure. The residue was dissolved in CHCl$_3$ (20 ml) and pivaloyl chloride (790 mg) and Et$_3$N (80 mg) were added, which was followed by stirring at room temperature for 30 min. CHCl$_3$ (100 ml) was added, and the mixture was washed successively with 5% aqueous citric acid and saturated brine and dried over anhydrous sodium sulfate. CHCl$_3$ was evaporated under reduced pressure. The residue was purified by silica gel column chromatography (eluent: CHCl$_3$/MeOH=50/1–10/1) to give 2.6 g of N-[1-acetyl-3-(2-ethoxycarbonylethyl)-4,6-dimethylindolin-7-yl]-2,2-dimethylpropanamide.

$^1$H-NMR (CDCl$_3$) δ:

1.25 (9H, s, —C(CH$_3$)$_3$), 1.26 (3H, t, J=7.1 Hz, —CH$_2$CH$_3$), 1.60–2.20 (2H, m, —CH$_2$CH$_2$CO$_2$—), 2.00–2.20 (2H, m, CH$_2$CH$_2$CO$_2$—), 2.17, 2.20, 2.27 (9H, s×3, —CH$_3$×2, >NCOCH$_3$), 3.00–3.20 (1H, m, Indoline C$_3$—H), 3.90 (2H, m, Indoline C$_2$—H), 4.10 (2H, q, J=7.1 Hz, —CH$_2$CH$_3$), 6.88 (1H, s, Indoline C$_5$—H), 9.00 (1H, br, —CONH—).

(9) N-[1-Acetyl-3-(2-ethoxycarbonylethyl)-4,6-dimethylindolin-7-yl]-2,2-dimethylpropanamide (2.6 g) was dissolved in EtOH (40 ml), and a solution of KOH (1.3 g) in water (10 ml) was added, which was followed by refluxing for 20 hr. EtOH was evaporated under reduced pressure, and the mixture was adjusted to pH 5 with 2N hydrochloric acid and extracted with CHCl$_3$ (100 ml). The CHCl$_3$ layer was washed with water and dried over anhydrous sodium sulfate. CHCl$_3$ was evaporated under reduced pressure to give 1.5 g of N-[3-(2-carboxyethyl)-4,6-dimethylindolin-7-yl]-2,2-dimethylpropanamide.

$^1$H-NMR (CDCl$_3$) δ:

1.33 (9H, s, —C(CH$_3$)$_3$), 1.60–2.20 (2H, m, —CH$_2$CH$_2$CO$_2$H), 2.14, 2.26 (6H, s×3, —CH$_3$×2), 2.20–2.40 (2H, m, —CH$_2$CH$_2$CO$_2$H), 3.10–3.80 (3H, m, Indoline C$_2$—H, C$_3$—H), 6.44 (1H, s, Indoline C$_5$—H), 6.74 (2H, br, —CO$_2$H, >NH).

(10) N-[3-(2-Carboxyethyl)-4,6-dimethylindolin-7-yl]-2,2-dimethylpropanamide (1.5 g) was dissolved in AcOEt (10 ml) and a solution of CH$_2$N$_2$ in ether was added. AcOEt (100 ml) was added, and after washing with water, the mixture was dried over anhydrous sodium sulfate. AcOEt was evaporated under reduced pressure. The residue was purified by silica gel column chromatography (eluent: CHCl$_3$/MeOH=50/1–10/1) to give 1.0 g of N-[3-(2-methoxycarbonylethyl)-4,6-dimethylindolin-7-yl]-2,2-dimethylpropanamide.

$^1$H-NMR (CDCl$_3$) δ:

1.34 (9H, s, —C(CH$_3$)$_3$), 1.60–2.20 (2H, m, —CH$_2$CH$_2$CO$_2$—), 2.15, 2.23 (6H, s×2, —CH$_3$×2), 2.20–2.40 (2H, m, —CH$_2$CH$_2$CO$_2$CH$_3$), 3.10–3.80 (3H, m, Indoline C$_2$—H, C$_3$—H), 3.64 (2H, s, —CO$_2$CH$_3$), 6.40 (1H, s, Indoline C$_5$—H), 7.05 (1H, br, >NH).

(11) N-[3-(2-Methoxycarbonylethyl)-4,6-dimethylindolin-7-yl]-2,2-dimethylpropanamide (1.0 g) was dissolved in DMF (10 ml) and 1-iodooctane (1.44 g) and K$_2$CO$_3$ (830 mg) were added, which was followed by stirring at 40° C. for 10 hr. AcOEt (100 ml) was added, and after washing with water, the mixture was dried over anhydrous sodium sulfate. AcOEt was evaporated under reduced pressure. The residue was purified by silica gel column chromatography (eluent: benzene/AcOEt=20/1–5/1) to give 1.1 g of the title compound.

IR (Nujol) cm$^{-1}$: 1730, 1620.

$^1$H-NMR (CDCl$_3$) δ:

0.70–1.00 (3H, br-t, —(CH$_2$)$_6$CH$_3$), 1.32 (9H, s, —C(CH$_3$)$_3$), 1.00–1.60 (12H, m, —(CH$_2$)$_6$CH$_3$), 1.60–2.20 (2H, m, —CH$_2$CH$_2$CO$_2$—), 2.05, 2.18 (6H, s×2, —CH$_3$×2), 2.20–2.40 (2H, m, —CH$_2$CH$_2$CO$_2$CH$_3$), 3.10–3.80 (5H, m, Indoline C$_2$—H, C$_3$—H, >NCH$_2$—), 3.64 (3H, s, —CO$_2$CH$_3$), 6.38 (1H, s, Indoline C$_5$—H), 6.70 (1H, br, —CONH—).

EXAMPLE 11

N-[(1-Octyl-3-(2-carboxyethyl)-4,6-dimethylindolin-7-yl)]-2,2-dimethylpropanamide N-[(1-Octyl-3-(2-methoxycarbonylethyl)-4,6-dimethylindolin-7-yl)]-2,2-dimethylpropanamide (1.1 g) was dissolved in EtOH (10 ml) and a solution of NaOH (494 mg) in water (3 ml) was added, which was followed by stirring at room temperature for 30 min. EtOH was evaporated under reduced pressure and CHCl$_3$ (50 ml) was added. After washing successively with 5% aqueous citric acid and saturated brine, the mixture was dried over anhydrous sodium sulfate. CHCl$_3$ was evaporated under reduced pressure. The residue was purified by silica gel column chromatography (eluent: CHCl$_3$/MeOH=50/1–10/1) to give 800 mg of the title compound.

IR (Nujol) cm$^{-1}$: 1700, 1680.
$^1$H-NMR (CDCl$_3$) δ:
0.70–1.00 (3H, br-t, —(CH$_2$)$_7$CH$_3$), 1.38 (9H, s, —C(CH$_3$)$_3$), 1.00–1.60 (12H, m, —(CH$_2$)$_6$CH$_3$), 1.60–2.20 (2H, m, —CH$_2$CH$_2$CO$_2$H), 2.07, 2.16 (6H, s×2, —CH$_3$×2), 2.20–2.40 (2H, m, CH$_2$CH$_2$CO$_2$H), 3.10–3.80 (3H, m, Indoline C$_2$—H, C$_3$—H), 3.27 (2H, br-t, >NCH$_2$—), 6.45 (1H, s, Indoline C$_5$—H), 7.20 (1H, br, —CONH—), 7.60 (1H, br, —CO$_2$H).

EXAMPLE 12

N-(1-Octyl-5-carboxymethyl-4,6-dimethylindol-7-yl)-2,2-dimethylpropanamide (1) N-(5-ethoxycarbonylmethyl-4,6-dimethylindolin-7-yl)-2,2-dimethylpropanamide (1.0 g) was dissolved in xylene (75 ml), and 10% Pd-C (250 mg) was added, which was followed by refluxing for 1 hr. Pd-C was filtered off and xylene was evaporated under reduced pressure. The residue was purified by silica gel column chromatography (eluent: benzene-CHCl$_3$) to give 0.9 g of N-(5-ethoxycarbonylmethyl-4,6-dimethylindol-7-yl)-2,2-dimethylpropanamide.

IR (Nujol) cm$^{-1}$: 1732, 1629.
$^1$H-NMR (CDCl$_3$) δ:
1.23 (3H, t, J=7.0 Hz, —CH$_2$CH$_3$), 1.40 (9H, s, —C(CH$_3$)$_3$), 2.32 (3H, s, —CH$_3$), 2.52 (3H, s, —CH$_3$), 3.80 (2H, m, —CH$_2$CO$_2$—), 4.13 (2H, q, J=7.0 HZ, —CH$_2$CH$_3$), 6.50 (1H, t, J=2.0 Hz, Indole C$_3$—H), 7.11 (1H, t, J=2.0 Hz, Indole C$_2$—H), 7.35 (1H, br, —CONH—), 8.88 (1H, br, >NH ).

(2) N-(5-Ethoxycarbonylmethyl-4,6-dimethylindol-7-yl)-2,2-dimethylpropanamide (1.45 g) was dissolved in DMF (10 ml) and NaH (P=60%, 132 mg) was added under a nitrogen atmosphere, which was followed by stirring at room temperature for 1 hr. Then, 1-iodooctane (1.06 g) was added and the mixture was stirred at the same temperature for 2 hr. The reaction mixture was poured into ice water. The mixture was extracted with AcOEt (100 ml), washed with water and dried over anhydrous sodium sulfate. AcOEt was evaporated under reduced pressure. The residue was purified by silica gel column chromatography (eluent: benzene/AcOEt-1/0–1/1) to give 1.02 g of N-(1-octyl-5-ethoxycarbonylmethyl-4,6-dimethylindol-7-yl)-2,2-dimethylpropanamide.

IR (Nujol) cm$^{-1}$: 1735, 1651.
$^1$H-NMR (CDCl$_3$) δ:
0.70–1.10 (3H, br-t, —(CH$_2$)$_7$CH$_3$), 1.10–1.70 (15H, m, —CH$_2$CH$_3$, —(CH$_2$)$_6$CH$_3$), 1.38 (9H, s, —C(CH$_3$)$_3$), 2.21 (3H, s, —CH$_3$), 2.47 (3H, s, —CH$_3$), 3.79 (2H, m, —CH$_2$CO$_2$—), 3.90–4.30 (4H, m, —CH$_2$CH$_3$, >NCH$_2$—), 6.42 (1H, t, J=3.5 Hz, Indole C$_3$—H), 6.91 (1H, t, J=3.5 Hz, Indole C$_2$—H), 7.12 (1H, br, —CONH—).

(3) N-(1-Octyl-5-ethoxycarbonylmethyl-4,6-dimethylindol-7-yl)-2,2-dimethylpropanamide (3.5 g) was dissolved in EtOH (50 ml), and a solution of NaOH (1.6 g) in water (20 ml) was added, which was followed by stirring at 60° C. for 1 hr. EtOH was evaporated under reduced pressure, and the residue was dissolved in water (20 ml), and washed with AcOEt (10 ml). The aqueous layer was neutralized with 2N HCl and extracted with AcOEt (50 ml). The AcOEt layer was washed successively with saturated brine and dried over anhydrous sodium sulfate. AcOEt was evaporated under reduced pressure to give 2.0 g of the title compound.

IR (Nujol) cm$^{-1}$: 1705, 1647.
$^1$H-NMR (CDCl$_3$) δ:
0.70–1.10 (3H, br, —(CH$_2$)$_7$CH$_3$), 1.10–1.70 (12H, m, —CH$_2$(CH$_2$)$_6$CH$_3$), 1.33 (9H, s, —C(CH$_3$)$_3$), 2.10 (3H, s, —CH$_3$), 2.39 (3H, s, —CH$_3$), 3.65 (1H, br, —CO$_2$H), 4.07 (2H, br-t, >NCH$_2$—), 4.15 (2H, s, —CH$_2$CO$_2$—), 6.38 (1H, t, J=3.5 Hz, Indole C$_3$—H), 6.89 (1H, t, J=3.5 Hz, Indole C$_2$—H), 7.25 (11H, br, —CONH—).

EXAMPLES 13–119

According to the method as described in any of the above-mentioned Examples 1–12, the compounds of Tables 1–9 were obtained.

TABLE 1

R$^4$ = —NHCOR$^7$

| Example | R$^1$ | R$^2$ | R$^3$ | R$^7$ | R$^6$ |
|---|---|---|---|---|---|
| 13 | —CH$_3$ | —CH$_2$CO$_2$H | —CH$_3$ | —C(CH$_3$)$_3$ | —(CH$_2$)$_4$CH$_3$ |
| 14 | —CH$_3$ | —CH$_2$CO$_2$H | —CH$_3$ | —C(CH$_3$)$_3$ | cyclopentyl |
| 15 | —CH$_3$ | —CH$_2$CO$_2$H | —CH$_3$ | —C(CH$_3$)$_3$ | —(CH$_2$)$_2$CH(CH$_3$)$_2$ |
| 16 | —CH$_3$ | —CH$_2$CO$_2$H | —CH$_3$ | —C(CH$_3$)$_3$ | —CH$_2$CH=C(CH$_3$)$_2$ |
| 17 | —CH$_3$ | —CH$_2$CO$_2$H | —CH$_3$ | —C(CH$_3$)$_3$ | —(CH$_2$)$_2$OCH$_2$CH$_3$ |
| 18 | —CH$_3$ | —CH$_2$CO$_2$H | —CH$_3$ | —C(CH$_3$)$_3$ | —(CH$_2$)$_5$CH$_3$ |

TABLE 1-continued $R^4 = -NHCOR^7$

| Example | R¹ | R² | R³ | R⁷ | R⁶ |
|---|---|---|---|---|---|
| 19 | —CH₃ | —CH₂CO₂H | —CH₃ | —C(CH₃)₃ | —cyclohexyl-H |
| 20 | —CH₃ | —CH₂CO₂H | —CH₃ | —C(CH₃)₃ | —CH₂-cyclopentyl-H |
| 21 | —CH₃ | —CH₂CO₂H | —CH₃ | —C(CH₃)₃ | —(CH₂)₃CH(CH₃)₂ |
| 22 | —CH₃ | —CH₂CO₂H | —CH₃ | —C(CH₃)₃ | —CH₂CH(CH₂CH₃)₂ |
| 23 | —CH₃ | —CH₂CO₂H | —CH₃ | —C(CH₃)₃ | —(CH₂)₂O(CH₂)₂CH₃ |
| 24 | —CH₃ | —CH₂CO₂H | —CH₃ | —C(CH₃)₃ | —(CH₂)₆CH₃ |
| 25 | —CH₃ | —CH₂CO₂H | —CH₃ | —C(CH₃)₃ | —CH₂-cyclohexyl-H |
| 26 | —CH₃ | —CH₂CO₂H | —CH₃ | —C(CH₃)₃ | —(CH₂)₄CH(CH₃)₂ |

TABLE 2

$R^4 = -NHCOR^7$

| Example | R¹ | R² | R³ | R⁷ | R⁶ |
|---|---|---|---|---|---|
| 27 | —CH₃ | —CH₂CO₂H | —CH₃ | —C(CH₃)₃ | —(CH₂)₂CH(CH₂CH₃)₂ |
| 28 | —CH₃ | —CH₂CO₂H | —CH₃ | —C(CH₃)₃ | —(CH₂)₂O(CH₂)₃CH₃ |
| 29 | —CH₃ | —CH₂CO₂H | —CH₃ | —C(CH₃)₃ | —(CH₂)₂-cyclohexyl-H |
| 30 | —CH₃ | —CH₂CO₂H | —CH₃ | —C(CH₃)₃ | —(CH₂)₅CH(CH₃)₂ |
| 31 | —CH₃ | —CH₂CO₂H | —CH₃ | —C(CH₃)₃ | —(CH₂)₃CH(CH₂CH₃)₂ |
| 32 | —CH₃ | —CH₂CO₂H | —CH₃ | —C(CH₃)₃ | —(CH₂)₂O(CH₂)₄CH₃ |
| 33 | —CH₃ | —CH₂CO₂H | —CH₃ | —C(CH₃)₃ | —(CH₂)₈CH₃ |
| 34 | —CH₃ | —CH₂CO₂H | —CH₃ | —C(CH₃)₃ | —(CH₂)₆CH(CH₃)₂ |
| 35 | —CH₃ | —CH₂CO₂H | —CH₃ | —C(CH₃)₃ | —(CH₂)₄CH(CH₂CH₃)₂ |
| 36 | —CH₃ | —CH₂CO₂H | —CH₃ | —C(CH₃)₃ | —(CH₂)₉CH₃ |
| 37 | —CH₃ | —CH₂CO₂H | —CH₃ | —C(CH₃)₃ | —(CH₂)₇CH(CH₃)₂ |
| 38 | —CH₃ | —CH₂CO₂H | —CH₃ | —C(CH₃)₃ | —(CH₂)₁₀CH₃ |
| 39 | —CH₃ | —CH₂CO₂H | —CH₃ | —C(CH₃)₃ | —(CH₂)₈CH(CH₃)₂ |
| 40 | —CH₃ | —CH₂CO₂H | —CH₃ | —C(CH₃)₃ | —(CH₂)₁₁CH₃ |
| 41 | —CH₃ | —CH₂CO₂H | —CH₃ | —C(CH₃)₃ | —(CH₂)₉CH(CH₃)₂ |

TABLE 3

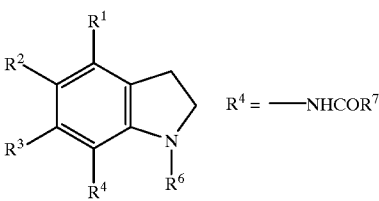

R⁴ = —NHCOR⁷

| Example | R¹ | R² | R³ | R⁷ | R⁶ |
|---|---|---|---|---|---|
| 42 | —CH₃ | —CH₂CO₂H | —CH₃ | —C(CH₃)₂C₄H₉ | —(CH₂)₅CH₃ |
| 43 | —CH₃ | —CH₂CO₂H | —CH₃ | —C(CH₃)₂C₄H₉ | —(CH₂)₆CH₃ |
| 44 | —CH₃ | —CH₂CO₂H | —CH₃ | —C(CH₃)₂C₄H₉ | —(CH₂)₇CH₃ |
| 45 | —CH₃ | —CH₂CO₂H | —CH₃ | —C(CH₃)₂C₆H₁₃ | —(CH₂)₅CH₃ |
| 46 | —CH₃ | —CH₂CO₂H | —CH₃ | —C(CH₃)₂C₆H₁₃ | —(CH₂)₆CH₃ |
| 47 | —CH₃ | —CH₂CO₂H | —CH₃ | —C(CH₃)₂C₆H₁₃ | —(CH₂)₇CH₃ |
| 48 | —CH₃ | —CH₂CO₂H | —CH₃ | —C(CH₃)₂C₈H₁₇ | —(CH₂)₅CH₃ |
| 49 | —CH₃ | —CH₂CO₂H | —CH₃ | —C(CH₃)₂C₈H₁₇ | —(CH₂)₆CH₃ |
| 50 | —CH₃ | —CH₂CO₂H | —CH₃ | —C(CH₃)₂C₈H₁₇ | —(CH₂)₇CH₃ |
| 51 | —CH₂CH₃ | —CH₂CO₂H | —CH₂CH₃ | —C(CH₃)₃ | —(CH₂)₅CH₃ |
| 52 | —CH₂CH₃ | —CH₂CO₂H | —CH₂CH₃ | —C(CH₃)₃ | —(CH₂)₆CH₃ |
| 53 | —CH₂CH₃ | —CH₂CO₂H | —CH₂CH₃ | —C(CH₃)₃ | —(CH₂)₇CH₃ |
| 54 | —CH₂CH₃ | —CH₂CO₂H | —CH₂CH₃ | —C(CH₃)₃ | —(CH₂)₈CH₃ |
| 55 | —CH₂CH₃ | —CH₂CO₂H | —CH₂CH₃ | —C(CH₃)₃ | —(CH₂)₉CH₃ |
| 56 | —OCH₃ | —CH₂CO₂H | —OCH₃ | —C(CH₃)₃ | —(CH₂)₅CH₃ |
| 57 | —OCH₃ | —CH₂CO₂H | —OCH₃ | —C(CH₃)₃ | —(CH₂)₆CH₃ |
| 58 | —OCH₃ | —CH₂CO₂H | —OCH₃ | —C(CH₃)₃ | —(CH₂)₇CH₃ |
| 59 | —OCH₃ | —CH₂CO₂H | —OCH₃ | —C(CH₃)₃ | —(CH₂)₈CH₃ |
| 60 | —OCH₃ | —CH₂CO₂H | —OCH₃ | —C(CH₃)₃ | —(CH₂)₉CH₃ |
| 61 | —CH₃ | —CH₂OH | —CH₃ | —C(CH₃)₃ | —(CH₂)₅CH₃ |
| 62 | —CH₃ | —CH₂OH | —CH₃ | —C(CH₃)₃ | —(CH₂)₆CH₃ |

TABLE 4

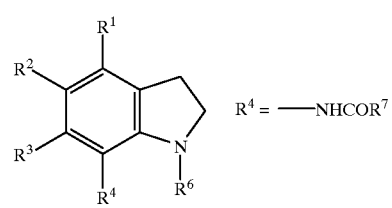

R⁴ = —NHCOR⁷

| Example | R¹ | R² | R³ | R⁷ | R⁶ |
|---|---|---|---|---|---|
| 63 | —CH₃ | —CH₂OH | —CH₃ | —C(CH₃)₃ | —(CH₂)₈CH₃ |
| 64 | —CH₃ | —CH₂OH | —CH₃ | —C(CH₃)₃ | —(CH₂)₉CH₃ |
| 65 | —CH₃ | —CH₂N(CH₃)₂ | —CH₃ | —C(CH₃)₃ | —(CH₂)₅CH₃ |
| 66 | —CH₃ | —CH₂N(CH₃)₂ | —CH₃ | —C(CH₃)₃ | —(CH₂)₆CH₃ |
| 67 | —CH₃ | —CH₂N(CH₃)₂ | —CH₃ | —C(CH₃)₃ | —(CH₂)₈CH₃ |
| 68 | —CH₃ | —CH₂N(CH₃)₂ | —CH₃ | —C(CH₃)₃ | —(CH₂)₉CH₃ |
| 69 | —H | —CH₂CO₂H | —CH₃ | —C(CH₃)₃ | —(CH₂)₅CH₃ |
| 70 | —H | —CH₂CO₂H | —CH₃ | —C(CH₃)₃ | —(CH₂)₆CH₃ |
| 71 | —H | —CH₂CO₂H | —CH₃ | —C(CH₃)₃ | —(CH₂)₇CH₃ |
| 72 | —H | —CH₂CO₂H | —CH₃ | —C(CH₃)₃ | —(CH₂)₈CH₃ |
| 73 | —H | —CH₂CO₂H | —CH₃ | —C(CH₃)₃ | —(CH₂)₉CH₃ |
| 74 | —H | —CH₂OH | —CH₃ | —C(CH₃)₃ | —(CH₂)₅CH₃ |
| 75 | —H | —CH₂OH | —CH₃ | —C(CH₃)₃ | —(CH₂)₆CH₃ |
| 76 | —H | —CH₂OH | —CH₃ | —C(CH₃)₃ | —(CH₂)₇CH₃ |
| 77 | —H | —CH₂OH | —CH₃ | —C(CH₃)₃ | —(CH₂)₈CH₃ |
| 78 | —H | —CH₂OH | —CH₃ | —C(CH₃)₃ | —(CH₂)₉CH₃ |
| 79 | —H | —CH₂N(CH₃)₂ | —CH₃ | —C(CH₃)₃ | —(CH₂)₅CH₃ |
| 80 | —H | —CH₂N(CH₃)₂ | —CH₃ | —C(CH₃)₃ | —(CH₂)₆CH₃ |
| 81 | —H | —CH₂N(CH₃)₂ | —CH₃ | —C(CH₃)₃ | —(CH₂)₇CH₃ |
| 82 | —H | —CH₂N(CH₃)₂ | —CH₃ | —C(CH₃)₃ | —(CH₂)₈CH₃ |
| 83 | —H | —CH₂N(CH₃)₂ | —CH₃ | —C(CH₃)₃ | —(CH₂)₉CH₃ |

TABLE 5

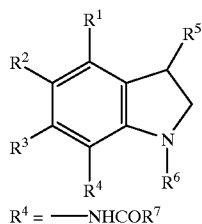

$R^4 =$ —NHCOR$^7$

| Example | R$^1$ | R$^2$ | R$^3$ | R$^7$ | R$^5$ | R$^6$ |
|---|---|---|---|---|---|---|
| 84 | —CH$_3$ | —H | —CH$_3$ | —C(CH$_3$)$_3$ | —(CH$_2$)$_2$CO$_2$H | —(CH$_2$)$_5$CH$_3$ |
| 85 | —CH$_3$ | —H | —CH$_3$ | —C(CH$_3$)$_3$ | —(CH$_2$)$_2$CO$_2$H | —(CH$_2$)$_6$CH$_3$ |
| 86 | —CH$_3$ | —H | —CH$_3$ | —C(CH$_3$)$_3$ | —(CH$_2$)$_2$OH | —(CH$_2$)$_5$CH$_3$ |
| 87 | —CH$_3$ | —H | —CH$_3$ | —C(CH$_3$)$_3$ | —(CH$_2$)$_2$OH | —(CH$_2$)$_6$CH$_3$ |
| 88 | —CH$_3$ | —H | —CH$_3$ | —C(CH$_3$)$_3$ | —(CH$_2$)$_2$N(CH$_3$)$_2$ | —(CH$_2$)$_5$CH$_3$ |
| 89 | —CH$_3$ | —H | —CH$_3$ | —C(CH$_3$)$_3$ | —(CH$_2$)$_2$N(CH$_3$)$_2$ | —(CH$_2$)$_6$CH$_3$ |
| 90 | —CH$_3$ | —H | —CH$_3$ | —C(CH$_3$)$_3$ | —(CH$_2$)$_2$N(CH$_3$)$_2$ | —(CH$_2$)$_7$CH$_3$ |

TABLE 6

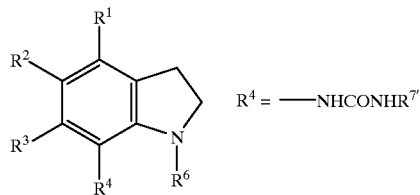

$R^4 =$ —NHCONHR$^{7'}$

| Example | R$^1$ | R$^2$ | R$^3$ | R$^7$ | R$^6$ |
|---|---|---|---|---|---|
| 91 | —CH$_3$ | —CH$_2$CO$_2$H | —CH$_3$ | —(CH$_2$)$_3$CH$_3$ | —(CH$_2$)$_7$CH$_3$ |
| 92 | —CH$_3$ | —CH$_2$CO$_2$H | —CH$_3$ | —(CH$_2$)$_3$CH$_3$ | —(CH$_2$)$_8$CH$_3$ |
| 93 | —CH$_3$ | —CH$_2$CO$_2$H | —CH$_3$ | —(CH$_2$)$_3$CH$_3$ | —(CH$_2$)$_9$CH$_3$ |
| 94 | —CH$_2$CH$_3$ | —CH$_2$CO$_2$H | —CH$_2$CH$_3$ | —(CH$_2$)$_3$CH$_3$ | —(CH$_2$)$_7$CH$_3$ |
| 95 | —CH$_2$CH$_3$ | —CH$_2$CO$_2$H | —CH$_2$CH$_3$ | —(CH$_2$)$_3$CH$_3$ | —(CH$_2$)$_8$CH$_3$ |
| 96 | —CH$_2$CH$_3$ | —CH$_2$CO$_2$H | —CH$_2$CH$_3$ | —(CH$_2$)$_3$CH$_3$ | —(CH$_2$)$_9$CH$_3$ |
| 97 | —OCH$_3$ | —CH$_2$CO$_2$H | —OCH$_3$ | —(CH$_2$)$_3$CH$_3$ | —(CH$_2$)$_7$CH$_3$ |
| 98 | —OCH$_3$ | —CH$_2$CO$_2$H | —OCH$_3$ | —(CH$_2$)$_3$CH$_3$ | —(CH$_2$)$_8$CH$_3$ |
| 99 | —OCH$_3$ | —CH$_2$CO$_2$H | —OCH$_3$ | —(CH$_2$)$_3$CH$_3$ | —(CH$_2$)$_9$CH$_3$ |

TABLE 7

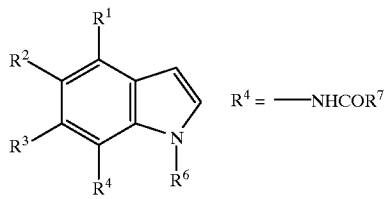

$R^4 =$ —NHCOR$^7$

| Example | R$^1$ | R$^2$ | R$^3$ | R$^7$ | R$^6$ |
|---|---|---|---|---|---|
| 100 | —CH$_3$ | —CH$_2$CO$_2$H | —CH$_3$ | —C(CH$_3$)$_3$ | —(CH$_2$)$_8$CH$_3$ |
| 101 | —CH$_3$ | —CH$_2$CO$_2$H | —CH$_3$ | —C(CH$_3$)$_3$ | —(CH$_2$)$_9$CH$_3$ |
| 102 | —CH$_2$CH$_3$ | —CH$_2$CO$_2$H | —CH$_2$CH$_3$ | —C(CH$_3$)$_3$ | —(CH$_2$)$_7$CH$_3$ |
| 103 | —CH$_2$CH$_3$ | —CH$_2$CO$_2$H | —CH$_2$CH$_3$ | —C(CH$_3$)$_3$ | —(CH$_2$)$_8$CH$_3$ |
| 104 | —CH$_2$CH$_3$ | —CH$_2$CO$_2$H | —CH$_2$CH$_3$ | —C(CH$_3$)$_3$ | —(CH$_2$)$_9$CH$_3$ |
| 105 | —OCH$_3$ | —CH$_2$CO$_2$H | —OCH$_3$ | —C(CH$_3$)$_3$ | —(CH$_2$)$_7$CH$_3$ |
| 106 | —OCH$_3$ | —CH$_2$CO$_2$H | —OCH$_3$ | —C(CH$_3$)$_3$ | —(CH$_2$)$_8$CH$_3$ |
| 107 | —OCH$_3$ | —CH$_2$CO$_2$H | —OCH$_3$ | —C(CH$_3$)$_3$ | —(CH$_2$)$_9$CH$_3$ |

TABLE 8

[Structure: indoline with R1, R2, R3, R4 on benzene ring and R6 on N; R4 = —NHCOR7]

| Example | R¹ | R² | R³ | R⁷ | R⁶ |
|---|---|---|---|---|---|
| 108 | —CH₃ | —CH₂CO₂H | —CH₃ | —(CH₂)₂OCH₃ | —(CH₂)₇CH₃ |
| 109 | —CH₃ | —CH₂CO₂H | —CH₃ | —(CH₂)₂SCH₃ | —(CH₂)₇CH₃ |
| 110 | —CH₃ | —CH₂CO₂H | —CH₃ | cyclohexyl | —(CH₂)₇CH₃ |
| 111 | —CH₃ | —CH₂CO₂H | —CH₃ | —CH₂-cyclohexyl | —(CH₂)₇CH₃ |
| 112 | —CH₃ | —CH₂CO₂H | —CH₃ | phenyl | —(CH₂)₇CH₃ |
| 113 | —CH₃ | —CH₂CO₂H | —CH₃ | —CH₂-phenyl | —(CH₂)₇CH₃ |
| 114 | —CH₃ | —CH₂CO₂H | —CH₃ | —C(CH₃)₃ | —(CH₂)₂S(CH₂)₃CH₃ |
| 115 | —CH₃ | —CH₂CO₂H | —CH₃ | —C(CH₃)₃ | —CH₂-phenyl |
| 116 | —H | —CH₂CO₂Et | —CH₃ | —C(CH₃)₃ | —(CH₂)₇CH₃ |

TABLE 9

[Structure: indoline with R¹, R², R⁴ on benzene ring and R⁶ on N; R⁴ = —NHCOR⁷]

| Example | R¹ | R² | R⁴ | R⁷ | R⁶ |
|---|---|---|---|---|---|
| 117 | —CH₂CO₂H | —CH₃ | —CH₃ | —C(CH₃)₃ | —(CH₂)₅CH₃ |
| 118 | —CH₂CO₂H | —CH₃ | —CH₃ | —C(CH₃)₃ | —(CH₂)₈CH₃ |
| 119 | —CH₂CO₂H | —CH₃ | —CH₃ | —C(CH₃)₃ | —(CH₂)₁₀CH₃ |

The $^1$H-NMR values of the compound of the above Examples 13–119 are shown in the following.

Example 13: 0.7–1.1 (3H, br-t), 1.1–1.7 (6H, m), 1.33 (9H, s), 2.01 (3H, s), 2.15 (3H, s), 2.70–3.10 (4H, m), 3.41 (2H, t), 3.56 (2H, s), 7.6–8.1 (2H, br).

Example 14: 0.70–1.70 (8H, m), 1.1–1.7 (6H, m), 1.33 (9H, s), 2.01 (3H, s), 2.15 (3H, s), 2.70–3.10 (3H, m), 3.41 (2H, t), 3.56 (2H, s), 7.6–8.1 (2H, br).

Example 15: 0.87 (6H, d), 1.1–1.8 (3H, m), 1.33 (9H, s), 2.01 (3H, s), 2.15 (3H, s), 2.70–3.10 (4H, m), 3.41 (2H, t), 3.56 (2H, s), 7.6–8.1 (2H, br).

Example 16: 1.65 (6H, s), 1.33 (9H, s), 2.01 (3H, s), 2.15 (3H, s), 2.70–3.10 (41, m), 3.41 (2H, t), 3.56 (2H, s), 5.20 (1H, br-t), 7.6–8.1 (2H, br).

Example 17: 1.59 (3H, t), 1.33 (9H, s), 2.01 (3H, s), 2.15 (3H, s), 2.70–3.10 (4H, m), 3.3–3.6 (6H, m), 3.56 (2H, s), 7.6–8.1 (2H, br).

Example 18: 0.7–1.1 (3H, br-t), 1.1–1.7 (8H, m), 1.33 (9H, s), 2.01 (3H, s), 2.15 (3H, s), 2.70–3.10 (4H, m), 3.41 (2H, t), 3.56 (2H, s), 7.6–8.1 (2H, br).

Example 19: 0.7–1.70 (10H, m), 1.33 (9H, s), 2.01 (3H, s), 2.15 (3H, s), 2.70–3.10 (3H, m), 3.41 (2H, t), 3.56 (2H, s), 7.6–8.1 (2H, br).

Example 20: 0.7–1.70 (9H, m), 1.33 (9H, s), 2.01 (3H, s), 2.15 (3H, s), 2.70–3.10 (4H, m), 3.41 (2H, t), 3.56 (2H, s), 7.6–8.1 (2H, br).

Example 21: 0.87 (6H, d), 1.1–1.8 (5H, m), 1.33 (9H, s), 2.01 (3H, s), 2.15 (3H, s), 2.70–3.10 (4H, m), 3.41 (2H, t), 3.56 (2H, s), 7.6–8.1 (2H, br).

Example 22: 0.7–1.0 (6H, br-t), 1.0–1.7 (5H, m), 1.33 (9H, s), 2.01 (3H, s), 2.15 (3H, s), 2.70–3.10 (4H, m), 3.41 (2H, t), 3.56 (2H, s), 7.6–8.1 (2H, br).

Example 23: 1.59 (3H, br-t), 1.0–1.7 (2H, m), 1.33 (9H, s), 2.01 (3H, s), 2.15 (3H, s), 2.70–3.10 (4H, m), 3.3–3.6 (6H, m), 3.56 (2H, s), 7.6–8.1 (2H, br).

Example 24: 0.7–1.10 (3H, br-t), 1.1–1.7 (10H,1 m), 1.33 (9H, s), 2.01 (3H, s), 2.15 (3H, s), 2.70–3.10 (4H, m), 3.41 (2H, t), 3.56 (2H, s), 7.6–8.1 (2H, br).

Example 25: 0.7–1.70 (11H, m), 1.33 (9H, s), 2.01 (3H, s), 2.15 (3H, s), 2.70–3.10 (4H, m), 3.41 (2H, t), 3.56 (2H, s), 7.6–8.1 (2H, br).

Example 26: 0.87 (6H, d), 1.1–1.8 (7H, m), 1.33 (9H, s), 2.01 (3H, s), 2.15 (3H, s), 2.70–3.10 (4H, m), 3.41 (2H, t), 3.56 (2H, s), 7.6–8.1 (2H, br).

Example 27: 1.59 (6H, br-t), 1.1–1.7 (7H, m), 1.33 (9H, s), 2.01 (3H, s), 2.15 (3H, s), 2.70–3.10 (4H, m), 3.41 (2H, t), 3.56 (2H, s), 7.6–8.1 (2H, br).

Example 28: 1.59 (3H, br-t), 1.0–1.7 (4H, m), 1.33 (9H, s), 2.01 (3H, s), 2.15 (3H, s), 2.70–3.10 (4H, m), 3.3–3.6 (6H, m), 3.56 (2H, s), 7.6–8.1 (2H, br).

Example 29: 0.7–1.70 (13H, m), 1.33 (9H, s), 2.01 (3H, s), 2.15 (3H, s), 2.70–3.10 (4H, m), 3.41 (2H, t), 3.56 (2H, s), 7.6–8.1 (2H, br).

Example 30: 0.87 (6H, d), 1.1–1.8 (9H, m), 1.33 (9H, s), 2.01 (3H, s), 2.15 (3H, s), 2.70–3.10 (4H, m), 3.41 (2H, t), 3.56 (2H, s), 7.6–8.1 (2H, br).

Example 31: 1.59 (6H, br-t), 1.0–1.7 (9H, m), 1.33 (9H, s), 2.01 (3H, s), 2.15 (3H, s), 2.70–3.10 (4H, m), 3.41 (2H, t), 3.56 (2H, s), 7.6–8.1 (2H, br).

Example 32: 1.59 (3H, br-t), 1.0–1.7 (6H, m), 1.33 (9H, s), 2.01 (3H, s), 2.15 (3H, s), 2.70–3.10 (4H, m), 3.3–3.6 (6H, m), 3.56 (2H, s), 7.6–8.1 (2H, br).

Example 33: 0.7–1.10 (3H, br-t), 1.1–1.7 (14H, m), 1.33 (9H, s), 2.01 (3H, s), 2.15 (3H, s), 2.70–3.10 (4H, m), 3.41 (2H, t), 3.56 (2H, s), 7.6–8.1 (2H, br).

Example 34: 0.87 (6H, d), 1.1–1.8 (11H, m), 1.33 (9H, s), 2.01 (3H, s), 2.15 (3H, s), 2.70–3.10 (4H, m), 3.41 (2H, t), 3.56 (2H, s), 7.6–8.1 (2H, br).

Example 35: 1.59 (6H, br-t), 1.0–1.7 (11H, m), 1.33 (9H, s), 2.01 (3H, s), 2.15 (3H, s), 2.70–3.10 (4H, m), 3.41 (2H, t), 3.56 (2H, s), 7.6–8.1 (2H, br).

Example 36: 0.7–1.10 (3H, br-t), 1.1–1.7 (16H, m), 1.33 (9H, s), 2.01 (3H, s), 2.15 (3H, s), 2.70–3.10 (4H, m), 3.41 (2H, t), 3.56 (2H, s), 7.6–8.1 (2H, br).

Example 37: 0.87 (6H, d), 1.1–1.8 (13H, m), 1.33 (9H, s), 2.01 (3H, s), 2.15 (3H, s), 2.70–3.10 (4H, m), 3.41 (2H, t), 3.56 (2H, s), 7.6–8.1 (2H, br).

Example 38: 0.7–1.10 (3H, br-t), 1.1–1.7 (18H, m), 1.33 (9H, s), 2.01 (3H, s), 2.15 (3H, s), 2.70–3.10 (4H, m), 3.41 (2H, t), 3.56 (2H, s), 7.6–8.1 (2H, br).

Example 39: 0.87 (6H, d), 1.1–1.8 (15H, m), 1.33 (9H, s), 2.01 (3H, s), 2.15 (3H, s), 2.70–3.10 (4H, m), 3.41 (2H, t), 3.56 (2H, s), 7.6–8.1 (2H, br).

Example 40: 0.7–1.10 (3H, br-t), 1.1–1.7 (20H, m), 1.33 (9H, s), 2.01 (3H, s), 2.15 (3H, s), 2.70–3.10 (4H, m), 3.41 (2H, t), 3.56 (2H, s), 7.6–8.1 (2H, br).

Example 41: 0.87 (6H, d), 1.1–1.8 (17H, m), 1.33 (9H, s), 2.01 (3H, s), 2.15 (3H, s), 2.70–3.10 (4H, m), 3.41 (2H, t), 3.56 (2H, s), 7.6–8.1 (2H, br).

Example 42: 0.7–1.10 (6H, br-t), 1.1–2.0 (20H, m), 2.01 (3H, s), 2.15 (3H, s), 2.70–3.10 (4H, m), 3.41 (2H, t), 3.56 (2H, s), 7.6–8.1 (2H, br).

Example 43: 0.7–1.10 (6H, br-t), 1.0–2.0 (22H, m), 2.01 (3H, s), 2.15 (3H, s), 2.70–3.10 (4H, m), 3.41 (2H, t), 3.56 (2H, s), 7.6–8.1 (2H, br).

Example 44: 0.7–1.10 (6H, br-t), 1.0–2.0 (24H, m), 2.01 (3H, s), 2.15 (3H, s), 2.70–3.10 (4H, m), 3.41 (2H, t), 3.56 (2H, s), 7.6–8.1 (2H, br).

Example 45: 0.7–1.10 (6H, br-t), 1.0–2.0 (24H, m), 2.01 (3H, s), 2.15 (3H, s), 2.70–3.10 (4H, m), 3.41 (2H, t), 3.56 (2H, s), 7.6–8.1 (2H, br).

Example 46: 0.7–1.10 (6H, br-t), 1.0–2.0 (26H, m), 2.01 (3H, s), 2.15 (3H, s), 2.70–3.10 (4H, m), 3.41 (2H, t), 3.56 (2H, s), 7.6–8.1 (2H, br).

Example 47: 0.7–1.10 (6H, br-t), 1.0–2.0 (28H, m), 2.01 (3H, s), 2.15 (3H, s), 2.70–3.10 (4H, m), 3.41 (2H, t), 3.56 (2H, s), 7.6–8.1 (2H, br).

Example 48: 0.7–1.10 (6H, br-t), 1.0–2.0 (28H, m), 2.01 (3H, s), 2.15 (3H, s), 2.70–3.10 (4H, m), 3.41 (2H, t), 3.56 (2H, s), 7.6–8.1 (2H, br).

Example 49: 0.7–1.10 (6H, br-t), 1.0–2.0 (30H, m), 2.01 (3H, s), 2.15 (3H, s), 2.70–3.10 (4H, m), 3.41 (2H, t), 3.56 (2H, s), 7.6–8.1 (2H, br).

Example 50: 0.7–1.10 (6H, br-t), 1.0–2.0 (32H, m), 2.01 (3H, s), 2.15 (3H, s), 2.70–3.10 (4H, m), 3.41 (2H, t), 3.56 (2H, s), 7.6–8.1 (2H, br).

Example 51: 0.7–1.1 (3H, br-t), 1.1–1.7 (14H, m), 1.33 (9H, s), 2.42 (2H, q), 2.46 (2H, q), 2.7–3.1 (4H, m), 3.41 (2H, t), 3.56 (2H, t), 7.6–8.1 (2H, br).

Example 52: 0.7–1.1 (3H, br-t), 1.0–1.7 (16H, m), 1.33 (9H, s), 2.42 (2H, q), 2.46 (2H, q), 2.7–3.1 (4H, m), 3.41 (2H, t), 3.56 (2H, t), 7.6–8.1 (2H, br).

Example 53: 0.7–1.1 (3H, br-t), 1.0–1.7 (18H, m), 1.33 (9H, s), 2.42 (2H, q), 2.46 (2H, q), 2.7–3.1 (4H, m), 3.41 (2H, t), 3.56 (2H, t), 7.6–8.1 (2H, br).

Example 54: 0.7–1.1 (3H, br-t), 1.0–1.7 (20H, m), 1.33 (9H, s), 2.42 (2H, q), 2.46 (2H, q), 2.7–3.1 (4H, m), 3.41 (2H, t), 3.56 (2H, t), 7.6–8.1 (2H, br).

Example 55: 0.7–1.1 (3H, br-t), 1.0–1.7 (22H, m), 1.33 (9H, s), 2.42 (2H, q), 2.46 (2H, q), 2.7–3.1 (4H, m), 3.41 (2H, t), 3.56 (2H, t), 7.6–8.1 (2H, br).

Example 56: 0.7–1.1 (3H, br-t), 1.1–1.7 (8H, m), 1.33 (9H, s), 2.50–3.10 (4H, m), 3.32 (2H, t), 3.45 (2H, s), 3.73 (3H, s), 3.77 (3H, s), 7.6–8.1 (2H, br).

Example 57: 0.7–1.1 (3H, br-t), 1.0–1.7 (10H, m), 1.33 (9H, s), 2.50–3.10 (4H, m), 3.32 (2H, t), 3.45 (2H, s), 3.73 (3H, s), 3.77 (3H, s), 7.6–8.1 (2H, br).

Example 58: 0.7–1.1 (3H, br-t), 1.0–1.7 (12H, m), 1.33 (9H, s), 2.50–3.10 (4H, m), 3.32 (2H, t), 3.45 (2H, s), 3.73 (3H, s), 3.77 (3H, s), 7.6–8.1 (2H, br).

Example 59: 0.7–1.1 (3H, br-t), 1.0–1.7 (14H, m), 1.33 (9H, s), 2.50–3.10 (4H, m), 3.32 (2H, t), 3.45 (2H, s), 3.73 (3H, s), 3.77 (3H, s), 7.6–8.1 (2H, br).

Example 60: 0.7–1.1 (3H, br-t), 1.0–1.7 (16H, m), 1.33 (9H, s), 2.50–3.10 (4H, m), 3.32 (2H, t), 3.45 (2H, s), 3.73 (3H, s), 3.77 (3H, s), 7.6–8.1 (2H, br).

Example 61: 0.7–1.1 (3H, br-t), 1.1–1.7 (8H, m), 1.33 (9H, s), 2.14 (3H, s), 2.22 (3H, s), 2.70–3.10 (4H, s), 3.41 (2H, t), 4.62 (2H, s), 6.86 (2H, br).

Example 62: 0.7–1.1 (3H, br-t), 1.1–1.7 (10H, m), 1.33 (9H, s), 2.14 (3H, s), 2.22 (3H, s), 2.70–3.10 (4H, m), 3.41 (2H, t), 4.62 (2H, s), 6.86 (2H, br).

Example 63: 0.7–1.1 (3H, br-t), 1.1–1.7 (14H, m), 1.33 (9H, s), 2.14 (3H, s), 2.22 (3H, s), 2.70–3.10 (4H, m), 3.41 (2H, t), 4.62 (2H, s), 6.86 (2H, br).

Example 64: 0.7–1.1 (3H, br-t), 1.1–1.7 (16H, m), 1.33 (9H, s), 2.14 (3H, s), 2.22 (3H, s), 2.70–3.10 (4H, m), 3.41 (2H, t), 4.62 (2H, s), 6.86 (2H, br).

Example 65: 0.7–1.1 (3H, br-t), 1.1–1.7 (8H, m), 1.33 (9H, s), 2.00 (6H, s), 2.09 (3H, s), 2.23 (3H, s), 2.70–3.20 (4H, m), 3.31 (2H, s), 3.38 (2H, t), 6.84 (1H, br).

Example 66: 0.7–1.1 (3H, br-t), 1.1–1.7 (10H, m), 1.33 (9H, s), 2.00 (6H, s), 2.09 (3H, s), 2.23 (3H, s), 2.70–3.20 (4H, m), 3.31 (2H, s), 3.38 (2H, t), 6.84 (1H, br).

Example 67: 0.7–1.1 (3H, br-t), 1.1–1.7 (14H, m), 1.33 (9H, s), 2.00 (6H, s), 2.09 (3H, s), 2.23 (3H, s), 2.70–3.20 (4H, m), 3.31 (2H, s), 3.38 (2H, t), 6.84 (1H, br).

Example 68: 0.7–1.1 (3H, br-t), 1.1–1.7 (16H, m), 1.33 (9H, s), 2.00 (6H, s), 2.09 (3H, s), 2.23 (3H, s), 2.70–3.20 (4H, m), 3.31 (2H, s), 3.38 (2H, t), 6.84 (1H, br).

Example 69: 0.7–1.0 (3H, br), 1.0–1.7 (8H, m), 1.33 (9H, s), 1.97 (3H, s), 2.7–3.1 (4H, m), 3.35 (2H, t), 3.47 (2H, s), 6.90 (1H, s), 7.6–8.1 (2H, br).

Example 70: 0.7–1.0 (3H, br), 1.0–1.7 (10H, m), 1.33 (9H, s), 1.97 (3H, s), 2.7–3.1 (4H, m), 3.35 (2H, t), 3.47 (2H, s), 6.90 (1H, s), 7.6–8.1 (2H, br).

Example 71: 0.7–1.0 (3H, br), 1.0–1.7 (12H, m), 1.33 (9H, s), 1.97 (3H, s), 2.7–3.1 (4H, m), 3.35 (2H, t), 3.47 (2H, s), 6.90 (1H, s), 7.6–8.1 (2H, br).

Example 72: 0.7–1.0 (3H, br), 1.0–1.7 (14H, m), 1.33 (9H, s), 1.97 (3H, s), 2.7–3.1 (4H, m), 3.35 (2H, t), 3.47 (2H, s), 6.90 (1H, s), 7.6–8.1 (2H, br).

Example 73: 0.7–1.0 (3H, br), 1.0–1.7 (16H, m), 1.33 (9H, s), 1.97 (3H, s), 2.7–3.1 (4H, m), 3.35 (2H, t), 3.47 (2H, s), 6.90 (1H, s), 7.6–8.1 (2H, br).

Example 74: 0.7–1.0 (3H, br), 1.0–1.7 (8H, m), 1.33 (9H, s), 2.07 (3H, s), 2.89 (2H, t), 3.09 (2H, t), 3.40 (2H, t), 4.51 (2H, s), 6.90 (1H, s), 7.0–7.4 (2H, br).

Example 75: 0.7–1.0 (3H, br), 1.0–1.7 (10H, m), 1.33 (9H, s), 2.07 (3H, s), 2.89 (2H, t), 3.09 (2H, t), 3.40 (2H, t), 4.51 (2H, s), 6.90 (1H, s), 7.0–7.4 (2H, br).

Example 76: 0.7–1.0 (3H, br), 1.0–1.7 (12H, m), 1.33 (9H, s), 2.07 (3H, s), 2.89 (2H, t), 3.09 (2H, t), 3.40 (2H, t), 4.51 (2H, s), 6.90 (1H, s), 7.0–7.4 (2H, br).

Example 77: 0.7–1.0 (3H, br), 1.0–1.7 (14H, m), 1.33 (9H, s), 2.07 (3H, s), 2.89 (2H, t), 3.09 (2H, t), 3.40 (2H, t), 4.51 (2H, s), 6.90 (1H, s), 7.0–7.4 (2H, br).

Example 78: 0.7–1.0 (3H, br), 1.0–1.7 (16H, m), 1.33 (9H, s), 2.07 (3H, s), 2.89 (2H, t), 3.09 (2H, t), 3.40 (2H, t), 4.51 (2H, s), 6.90 (1H, s), 7.0–7.4 (2H, br).

Example 79: 0.7–1.0 (3H, br), 1.0–1.7 (8H, m), 1.33 (9H, s), 2.08 (3H, s), 2.23 (6H, s), 2.89 (2H, t), 3.14 (2H, t), 3.30 (2H, s), 3.38 (2H, t), 6.84 (1H, s), 6.90 (1H, br).

Example 80: 0.7–1.0 (3H, br), 1.0–1.7 (10H, m), 1.33 (9H, s), 2.08 (3H, s), 2.23 (6H, s), 2.89 (2H, t), 3.14 (2H, t), 3.30 (2H, s), 3.38 (2H, t), 6.84 (1H, s), 6.90 (1H, br).

Example 81: 0.7–1.0 (3H, br), 1.0–1.7 (12H, m), 1.33 (9H, s), 2.08 (3H, s), 2.23 (6H, s), 2.89 (2H, t), 3.14 (2H, t), 3.30 (2H, s), 3.38 (2H, t), 6.84 (1H, s), 6.90 (1H, br).

Example 82: 0.7–1.0 (3H, br), 1.0–1.7 (14H, m), 1.33 (9H, s), 2.08 (3H, s), 2.23 (6H, s), 2.89 (2H, t), 3.14 (2H, t), 3.30 (2H, s), 3.38 (2H, t), 6.84 (1H, s), 6.90 (1H, br).

Example 83: 0.7–1.0 (3H, br), 1.0–1.7 (16H, m), 1.33 (9H, s), 2.08 (3H, s), 2.23 (6H, s), 2.89 (2H, t), 3.14 (2H, t), 3.30 (2H, s), 3.38 (2H, t), 6.84 (1H, s), 6.90 (1H, br).

Example 84: 0.7–1.0 (3H, br-t), 1.00–1.60 (8H, m), 1.38 (9H, s), 1.60–2.20 (2H, m), 2.07 (3H, s), 2.16 (3H, s), 2.20–2.40 (2H, m), 3.10–3.80 (3H, m), 3.27 (2H, br-t), 6.45 (1H, s), 7.20–7.60 (2H, br).

Example 85: 0.7–1.0 (3H, br-t), 1.00–1.60 (10H, m), 1.38 (9H, s), 1.60–2.20 (2H, m), 2.07 (3H, s), 2.16 (3H, s), 2.20–2.40 (2H, m), 3.10–3.80 (3H, m), 3.27 (2H, br-t), 6.45 (1H, s), 7.20–7.60 (2H, br).

Example 86: 0.7–1.0 (3H, br-t), 1.0–2.0 (10H, m), 1.33 (9H, s), 2.07 (3H, s), 2.16 (3H, s), 2.60–3.60 (7H, m), 6.44 (1H, s), 6.78 (2H, br).

Example 87: 0.7–1.0 (3H, br-t), 1.0–2.0 (12H, m), 1.33 (9H, s), 2.07 (3H, s), 2.16 (3H, s), 2.60–3.60 (7H, m), 6.44 (1H, s), 6.78 (2H, br).

Example 88: 0.7–1.0 (3H, br-t), 1.0–2.0 (10H, m), 1.35 (9H, s), 2.07 (3H, s), 2.16 (3H, s), 2.19 (6H, s), 2.21 (2H, t), 2.6–3.6 (5H, m), 6.45 (1H, s), 7.2 (1H, br).

Example 89: 0.7–1.0 (3H, br-t), 1.0–2.0 (12H, m), 1.35 (9H, s), 2.07 (3H, s), 2.16 (3H, s), 2.19 (6H, s), 2.21 (2H, t), 2.6–3.6 (5H, m), 6.45 (1H, s), 7.2 (1H, br).

Example 90: 0.7–1.0 (3H, br-t), 1.0–2.0 (14H, m), 1.35 (9H, s), 2.07 (3H, s), 2.16 (3H, s), 2.19 (6H, s), 2.21 (2H, t), 2.6–3.6 (5H, m), 6.45 (1H, s), 7.2 (1H, br).

Example 91: 0.70–1.10 (6H, m), 1.10–1.90 (16H, m), 2.10 (6H, s), 1.80–2.00 (2H, br-t), 2.00–4.00 (6H, m), 3.55 (2H, s), 4.80 (1H, br), 5.50 (1H, br), 6.40 (1H, br).

Example 92: 0.70–1.10 (6H, m), 1.10–1.90 (18H, m), 2.10 (6H, s), 1.80–2.00 (2H, br-t), 2.00–4.00 (6H, m), 3.55 (2H, s), 4.80 (1H, br), 5.50 (1H, br), 6.40 (1H, br).

Example 93: 0.70–1.10 (6H, m), 1.10–1.90 (20H, m), 2.10 (6H, s), 1.80–2.00 (2H, br-t), 2.00–4.00 (6H, m), 3.55 (2H, s), 4.80 (1H, br), 5.50 (1H, br), 6.40 (1H, br).

Example 94: 0.70–1.10 (6H, m), 1.10–1.90 (22H, m), 2.09 (4H, br-t), 1.80–2.00 (2H, br-t), 2.00–4.00 (6H, m), 3.55 (2H, s), 4.80 (1H, br), 5.50 (1H, br), 6.40 (1H, br).

Example 95: 0.70–1.10 (6H, m), 1.10–1.90 (24H, m), 2.09 (4H, br-t), 1.80–2.00 (2H, br-t), 2.00–4.00 (6H, m), 3.55 (2H, s), 4.80 (1H, br), 5.50 (1H, br), 6.40 (1H, br).

Example 96: 0.70–1.10 (6H, m), 1.10–1.90 (26H, m), 2.09 (4H, br-t), 1.80–2.00 (2H, br-t), 2.00–4.00 (6H, m), 3.55 (2H, s), 4.80 (1H, br), 5.50 (1H, br), 6.40 (1H, br).

Example 97: 0.70–1.10 (6H, m), 1.10–1.90 (16H, m), 1.80–2.00 (2H, br-t), 2.00–4.00 (6H, m), 3.35 (2H, s), 3.74 (3H, s), 3.78 (3H, s), 4.80 (1H, br), 5.50 (1H, br), 6.40 (1H, br).

Example 98: 0.70–1.10 (6H, m), 1.10–1.90 (18H, m), 1.80–2.00 (2H, br-t), 2.00–4.00 (6H, m), 3.35 (2H, s), 3.74 (3H, s), 3.78 (3H, s), 4.80 (1H, br), 5.50 (1H, br), 6.40 (1H, br).

Example 99: 0.70–1.10 (6H, m), 1.10–1.90 (20H, m), 1.80–2.00 (2H, br-t), 2.00–4.00 (6H, m), 3.35 (2H, s), 3.74 (3H, s), 3.78 (3H, s), 4.80 (1H, br), 5.50 (1H, br), 6.40 (1H, br).

Example 100: 0.70–1.10 (3H, br-t), 1.10–1.70 (14H, m), 1.33 (9H, s), 2.10 (3H, s), 2.39 (3H, s), 3.71 (2H, br), 3.99 (2H, br-t), 4.15 (2H, s), 6.38 (1H, d), 6.89 (1H, d).

Example 101: 0.70–1.10 (3H, br-t), 1.10–1.70 (10H, m), 1.33 (9H, s), 2.10 (3H, s), 2.39 (3H, s), 3.71 (2H, br), 3.99 (2H, br-t), 4.15 (2H, s), 6.38 (1H, d), 6.89 (1H, d).

Example 102: 0.70–1.10 (3H, br-t), 1.10–1.70 (18H, m), 1.33 (9H, s), 2.08 (2H, q), 2.46 (2H, q), 3.71 (2H, br), 3.99 (2H, br-t), 4.15 (2H, s), 6.38 (1H, d), 6.89 (1H, d).

Example 103: 0.70–1.10 (3H, br-t), 1.10–1.70 (20H, m), 1.33 (9H, s), 2.08 (2H, q), 2.46 (2H, q), 3.71 (2H, br), 3.99 (2H, br-t), 4.15 (2H, s), 6.38 (1H, d), 6.89 (1H, d).

Example 104: 0.70–1.10 (3H, br-t), 1.10–1.70 (22H, m), 1.33 (9H, s), 2.42 (2H, q), 2.46 (2H, q), 3.71 (2H, br), 3.99 (2H, br-t), 4.15 (2H, s), 6.38 (1H, d), 6.89 (1H, d).

Example 105: 0.70–1.10 (3H, br-t), 1.10–1.70 (12H, m), 1.33 (9H, s), 3.60 (3H, s), 3.65 (3H, s), 3.71 (2H, br), 3.99 (2H, br-t), 4.15 (2H, s), 6.15 (1H, d), 6.70 (1H, d).

Example 106: 0.70–1.10 (3H, br-t), 1.10–1.70 (14H, m), 1.33 (9H, s), 3.60 (3H, s), 3.65 (3H, s), 3.71 (2H, br), 3.99 (2H, br-t), 4.15 (2H, s), 6.15 (1H, d), 6.70 (1H, d).

Example 107: 0.70–1.10 (3H, br-t), 1.10–1.70 (16H, m), 1.33 (9H, s), 3.60 (3H, s), 3.65 (3H, s), 3.71 (2H, br), 3.99 (2H, br-t), 4.15 (2H, s), 6.15 (1H, d), 6.70 (1H, d).

Example 108: 0.70–1.10 (3H, br-t), 1.10–2.00 (15H, m), 2.01 (3H, s), 2.15 (3H, s), 2.70–3.10 (4H, m), 3.37 (3H, s), 3.40 (2H, t), 3.41 (2H, t), 3.56 (2H, s), 7.60–8.10 (2H, br).

Example 109: 0.70–1.10 (3H, br-t), 1.10–2.00 (15H, m), 2.01 (3H, s), 2.15 (3H, s), 2.17 (3H, s), 2.45 (2H, s), 2.70–3.10 (4H, m), 3.41 (2H, t), 3.56 (2H, s), 7.60–8.10 (2H, br).

Example 110: 0.70–1.10 (3H, br-t), 1.10–2.00 (23H, m), 2.01 (3H, s), 2.70–3.10 (4H, m), 3.41 (2H, t), 3.56 (2H, s), 7.60–8.10 (2H, br).

Example 111: 0.70–1.10 (3H, br-t), 1.10–2.00 (25H, m), 2.01 (3H, s), 2.15 (3H, s), 2.70–3.10 (4H, m), 3.41 (2H, t), 3.56 (2H, s), 7.60–8.10 (2H, br).

Example 112: 0.70–1.10 (3H, br-t), 1.10–1.70 (12H, m), 2.01 (3H, s), 2.15 (3H, s), 2.70–3.10 (4H, m), 3.41 (2H, t), 3.56 (2H, s), 7.30–7.80 (3H, m), 7.60–8.10 (2H, br), 8.12 (2H, d).

Example 113: 0.70–1.10 (3H, br-t), 1.10–1.70 (12H, m), 2.01 (3H, s), 2.15 (3H, s), 2.70–3.10 (4H, m), 3.41 (2H, t), 3.53 (2H, s), 3.56 (2H, s), 7.30 (5H, s), 7.60–8.10 (2H, br).

Example 114: 1.59 (3H, br-t), 1.10–1.70 (4H, m), 1.33 (9H, s), 2.01 (3H, s), 2.15 (3H, s), 2.10–2.50 (4H, m), 2.70–3.10 (4H, m), 3.41 (2H, t), 3.56 (2H, s), 7.60–8.10 (2H, br).

Example 115: 1.33 (9H, s), 2.01 (3H, s),2.15 (3H, s), 3.02 (2H, t), 3.41 (2H, t), 3.56 (2H, s), 4.30 (2H, s), 7.30 (5H, s) 7.60–8.10 (2H, br).

Example 116: 0.70–1.10 (3H, br-t), 1.10–1.60 (15H, m), 1.34 (9H, s), 2.02 (3H, s), 2.90 (2H, t), 3.13 (2H, t), 3.38 (2H, t), 3.50 (2H, s), 4.12 (2H, q), 6.80 (1H, br), 6.85 (1H, s).

Example 117: 0.70–1.10 (3H, br-t), 1.10–2.00 (8H, m), 1.23 (9H, s), 2.07 (3H, s), 2.24 (3H, s), 2.70–3.10 (4H, m), 3.39 (2H, t), 3.35 (2H, s), 6.60–7.50 (2H, br).

Example 118: 0.70–1.10 (3H, br-t), 1.10–2.00 (12H, m), 1.23 (9H, s), 2.07 (3H, s), 2.24 (3H, s), 2.70–3.10 (4H, m), 3.39 (2H, t), 3.35 (2H, s), 6.60–7.50 (2H, br).

Example 119: 0.70–1.10 (3H, br-t), 1.10–2.00 (16H, m), 1.23 (9H, s), 2.07 (3H, s), 2.24 (3H, s), 2.70–3.10 (4H, m), 3.39 (2H, t), 3.35 (2H, s), 6.60–7.50 (2H, br).

EXAMPLE 120

N-(1-Octyl-5-carboxyethyl-4,6-dimethylindolin-7-yl)-2,2-dimethylpropanamide (1) N-(1-Octyl-5-chloroethyl-4,6-dimethylindolin-7-yl)-2,2-dimethylpropanamide (3.0 g) was dissolved in $CH_3CN$ (30 ml), and NaCH (3.7 g) and 18-crown-6 (0.1 g) were added, which was followed by refluxing for 17 hr under a nitrogen atmosphere. $CH_3CN$ was evaporated under reduced pressure, and water (100 ml) was added to the obtained residue. The mixture was extracted twice with AcOEt (100 ml). The AcOEt layer was washed with saturated brine (100 ml) and dried over anhydrous sodium sulfate, and AcOEt was evaporated under reduced pressure. The obtained residue was purified by silica gel column chromatography (eluent: AcOEt/benzene=1/10–1/5) to give 1.14 g of N-(1-octyl-5-cyanoethyl-4,6-dimethylindolin-7-yl)-2,2-dimethylpropanamide.

IR (Nujol)$cm^{-1}$: 2243, 1647, 1601.

$^1$H-NMR (CDCl$_3$) σ:

0.88 (3H, br-t, J=6.0 Hz, —(CH$_2$)$_7$CH$_3$), 1.10–1.90 (12H, m, —CH$_2$(CH$_2$)$_6$CH$_3$), 1.33 (9H, s, —C(CH$_3$)$_3$), 2.05, 2.15 (3H×2, s×2, indoline C$_{4,6}$ —CH$_3$), 2.38 (2H, t, J=7 Hz, —CH$_2$CN), 2.70–3.30 (6H, m, indoline C$_3$—H$_2$, >NCH$_2$—, —CH$_2$CH$_2$CN), 3.41 (2H, t, J=9 Hz, indoline C$_2$—H$_2$), 6.81 (1H, br, —CONH—).

(2) N-(1-Octyl-5-cyanoethyl-4,6-dimethylindolin-7-yl)-2,2-dimethylpropanamide (1.14 g) was dissolved in EtOH (26 ml), and a solution of NaOH (1.1 g) in water (7.5 ml) was added, which was followed by refluxing for 14 hr under a nitrogen atmosphere. EtOH was evaporated under reduced pressure. The obtained residue was dissolved in warm water (30 ml) and washed with ArOEt (30 ml). The aqueous layer was neutralized with 2N HCl and extracted with CHCl$_3$ (50 ml). CHCl$_3$ layer was evaporated under reduced pressure to give 830 mg of the title compound.

IR (Nujol)$cm^{-1}$: 1724, 1655, 1618.

$^1$H-NMR (CDCl$_3$) σ:

0.86 (3H, br-t, J=5.0 Hz, —(CH$_2$)$_7$CH$_3$), 1.10–2.10 (12H, m, —CH$_2$(CH$_2$)$_6$CH$_3$)1.42 (9H, s, —C(CH$_3$)$_3$), 2.12, 2.26 (3H×2, s×2, indoline C$_{4,6}$ —CH$_3$), 2.30–2.60 (2H, m, —CH$_2$O$_2$—), 2.90–3.40 (6H, m, indoline C$_3$—H$_2$, >NCH$_2$—, —CH$_2$CH$_2$CO$_2$—), 3.78 (1H, br, indoline C$_2$—H$_2$), 7.70 (1H, br —CO$_2$H), 9.91 (1H, br, —CONH—).

EXAMPLES 121–123

The compounds of Table 10 were obtained according to the method of the above Example 120.

TABLE 10

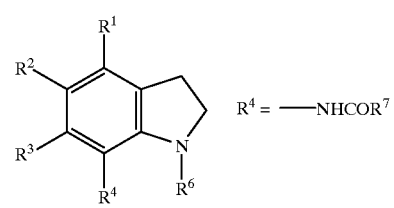

R$^4$ = —NHCOR$^7$

| Example | R$^1$ | R$^2$ | R$^3$ | R$^7$ | R$^6$ |
|---|---|---|---|---|---|
| 121 | —CH$_3$ | —CH$_2$CO$_2$H | —CH$_3$ | —C(CH$_3$)$_3$ | —(CH$_2$)$_6$S(CH$_2$)$_3$CH$_3$ |
| 122 | —CH$_3$ | —CH$_2$CO$_2$H | —CH$_3$ | —C(CH$_3$)$_3$ | —(CH$_2$)$_3$S(CH$_2$)$_3$CH$_3$ |
| 123 | —CH$_3$ | —(CH$_2$)$_3$CO$_2$H | —CH$_3$ | —C(CH$_3$)$_3$ | —(CH$_2$)$_7$CH$_3$ |

The $^1$H-NMR values of the compounds of the above Examples 121–123 are shown in the following.

Example 121: 0.91 (3H, br-t), 1.00–1.80 (12H, m), 1.37 (9H, s), 1.93 (3H, s), 2.06 (3H, s), 2.47 (4H, br-t), 3.00 (4H, br), 3.30–3.90 (4H, m), 8.60–9.90 (2H, br).

Example 122: 0.90 (3H, br-t), 1.00–1.80 (6H, m), 2.08 (3H, s), 2.21 (3H, s), 2.48 (4H, br-t), 2.90–3.40 (4H, m), 3.40–3.80 (2H, m), 3.61 (2H, s), 7.34 (1H, br), 8.48 (1H, br).

Example 123: 0.86 (3H, br-t), 1.00–1.50 (12H, m), 1.42 (9H, s), 2.00–2.90 (6H, m), 2.11 (3H, s), 2.23 (3H, s), 2.90–3.30 (4H, m), 3.70 (2H, br), 6.10 (1H, br), 9.21 (1H, br).

EXAMPLE 124

N-(1-Octyl-6-ethoxycarbonylmthyl-5,7-dimethyl-1,2,3,4-tetrahydroquinolin-8-yl)-2,2-dimethylpropanamide (1) 3,5-Xylidine (5.0 g) and acrylonitrile (2.3 g) were dissolved in acetic acid (2 ml), and the mixture was stirred at 60° C. for 20 hr. Ethyl acetate (200 ml) was added to the reaction mixture and neutralized with saturated aqueous solution of sodium hydrogencarbonate. The mixture was washed with water and dried over anhydrous sodium sulfate. The solvent was evaporated under reduced pressure. The residue was purified by silica gel column chromatography (eluent: ethyl acetate/benzene=1/10–1/3) to give 4.5 g of oily β-(3,5-dimethylanilino)propionitrile.
IR (Nujol) cm$^{-1}$; 2248, 1602.
$^1$H-NMR (CDCl$_3$) δ;
2.24 (6H, s, C$_{3,5}$—CH$_3$), 2.60 (2H, t, J=7.5 Hz, —CH$_2$CH$_2$CN), 3.48 (2H, t, J=7.5 Hz, —CH$_2$CH$_2$CN), 3.90 (1H, br, >NH), 6.24 (2H, s, C$_{2,6}$—H), 6.43 (1H, s, C$_4$—H).

(2) β-(3,5-Dimethylanilino)propionitrile (4.5 g) was dissolved in ethanol (50 ml), and a solution of NaOH (5.1 g) in water (25 ml) was added, which was followed by refluxing for 4 hr. The solvent was evaporated under reduced pressure. 2N Hydrochloric acid was added to adjust the residue acidic, and the mixture was washed with chloroform (100 ml). The aqueous layer was concentrated to about 20 ml and allowed to stand. The precipitated crystals were collected by filtration and dried to give 4.0 g of β-(3,5-dimethylanilino)propionic acid.
IR (Nujol) cm$^{-1}$; 1560.
$^1$H-NMR (DMSO-d$_6$) δ:
2.29 (6H, s, C$_{3,5}$—CH$_3$), 2.73 (2H, t, J=7.5 Hz, —CH$_2$CH$_2$CO—), 3.44 (2H, t, J=7.5 Hz, —CH$_2$CH$_2$CO—), 7.0 (3H, s, C$_{2,4,6}$—H), 9.80 (2H, br, —CO$_2$H, >NH).

(3) β-(3,5-Dimethylanilino)propionic acid (1.2 g) was added by portions to sulfuric acid (60° C., 12 ml), and the mixture was stirred at the same temperature for 0.5 hr. The reaction mixture was poured into ice water (100 ml) and extracted with chloroform (100 ml). After washing with water, the chloroform layer was dried over anhydrous sodium sulfate. The solvent was evaporated under reduced pressure. The residue was purified by silica gel column chromatography (eluent: ethyl acetate/benzene= 1/5–1/1) to give 750 mg of 5,7-dimethylquinolone as crystals.
IR (Nujol) cm$^{-1}$; 1645, 1614.
$^1$H-NMR (CDCl$_3$) δ;
2.19 (3H, s, C$_5$—CH$_3$), 2.57 (3H, s, C$_7$—CH$_3$), 2.63 (2H, t, J=7.5 Hz, C$_3$—H$_2$), 3.49 (2H, t, J=7.5 Hz, C$_2$—H$_2$), 4.39 (1H, br, >NH), 6.32 (2H, s, C$_{6,8}$—H).

(4) Lithium aluminum hydride (687 mg) was suspended in ether (16 ml), and aluminum chloride (4.2 g) was added. A solution of 5,7-dimethylquinolone (1.6 g) in ether (16 ml) was dropwise added and the mixture was refluxed for 0.5 hr. The reaction mixture was poured into ice water (100 ml) and extracted with chloroform (100 ml). After washing with water, the chloroform layer was dried over anhydrous sodium sulfate. The solvent was evaporated under reduced pressure. The obtained 5,7-dimethyl-1,2,3,4-tetrahydroquinoline was dissolved in chloroform (30 ml), and acetic anhydride (929 mg) was added, which was followed by stirring at room temperature for 1 hr. Chloroform (100 ml) was added to the reaction mixture, and the mixture was washed successively with saturated aqueous solution of sodium hydrogencarbonate and water and dried over anhydrous sodium sulfate. The solvent was evaporated under reduced pressure. The residue was purified by silica gel column chromatography (eluent: ethyl acetate/benzene=1/5–1/1) to give 1.5 g of oily 1-acetyl-5,7-dimethyl-1,2,3,4-tetrahydroquinoline.
IR (Nujol) cm$^{-1}$; 1625, 1614.
$^1$H-NMR (CDCl$_3$) δ;
1.70–2.10 (2H, m, C$_3$—H$_2$), 2.21 (6H, s×2, —OCH$_3$, Ar—CH$_3$), 2.29 (3H, s, Ar—CH$_3$), 2.54 (2H, t, J=7.1 Hz, C$_4$—H$_2$), 3.77 (2H, t, J=7.1 Hz, C$_2$—H$_2$), 6.83 (2H, s, C$_{6,8}$—H).

(5) 1-Acetyl-5,7-dimethyl-1,2,3,4-tetrahydroquinoline (3.0 g) was dissolved in conc. hydrochloric acid (6 ml), and 35% formaldehyde solution (2.5 g) and zinc chloride (400 mg) were added. The mixture was stirred at 40–50° C. for 2 hr while blowing hydrogen chloride. The reaction mixture was poured into ice water (100 ml) and extracted with chloroform (100 ml). After washing with water, the chloroform layer was dried over anhydrous sodium sulfate. The solvent was evaporated under reduced pressure. The obtained 1-acetyl-6-chloromethyl-5,7-dimethyl-1,2,3,4-tetrahydroquinoline was dissolved in acetonitrile (30 ml), and sodium cyanide (3.6 g) and 18-crown-6 (780 mg) were added, which was followed by refluxing for 5 hr. The solvent was evaporated under reduced pressure, and the residue was extracted with chloroform (100 ml). After washing with water, the chloroform layer was dried over anhydrous sodium sulfate. The solvent was evaporated under reduced pressure. The residue was purified by silica gel column chromatography (eluent: chloroform-chloroform/methanol=10/1) to give 2.4 g of oily 1-acetyl-6-cyanomethyl-5,7-dimethyl-1,2,3,4-tetrahydroquinoline.
IR (Nujol) cm$^{-1}$; 2248, 1650.
$^1$H-NMR (CDCl$_3$) δ;
1.80–2.20 (2H, m, C$_3$—H$_2$), 2.21, 2.29 (3H×2, s×2, C$_{5,7}$—CH$_3$), 2.37 (3H, s, —COCH$_3$), 2.68 (2H, t, J=7.5 Hz, C$_4$—H$_2$), 3.66 (2H, s, —CH$_2$CN), 3.76 (2H, t, J=7.5 Hz, C$_2$—H$_2$), 7.00 (1H, s, C$_8$—H).

(6) 1-Acetyl-6-cyanomethyl-5,7-dimethyl-1,2,3,4-tetrahydroquinoline (2.7 g) was dissolved in ethanol (30 ml), and a solution of NaOH (4.4 g) in water (10 ml) was added, which was followed by refluxing for 10 hr under nitrogen. The solvent was evaporated under reduced pressure, and the residue was extracted with chloroform (100 ml). After washing with water, the chloroform layer was dried over anhydrous sodium sulfate. The solvent was evaporated under reduced pressure. The obtained 6-carbamoylmethyl-5,7-dimethyl-1,2,3,4-tetrahydroquinoline was dissolved in N,N-dimethylformamide (10 ml), and octyl bromide (1.6 g), potassium carbonate (1.2 g) and potassium iodide (166 mg) were added, which was followed by stirring at 40° C. for 10 hr in nitrogen. The reaction mixture was extracted with ethyl acetate (100 ml). After washing with water, the ethyl acetate layer was dried over anhydrous sodium sulfate. The solvent was evaporated under reduced pressure. The residue was purified by silica gel column chromatography (eluent: chloroform/methanol=50/1–10/1) to give 600 mg of 1-octyl-6-carbamoylmethyl-5,7-dimethyl-1,2,3,4-tetrahydroquinoline as crystals.

IR (Nujol) cm$^{-1}$; 1654, 1624.

$^1$H-NMR (CDCl$_3$) δ;

0.60–1.10 (3H, br-t, —(CH$_2$)$_7$CH$_3$), 1.10–1.80 (12H, m, —(CH$_2$)$_6$CH$_3$), 1.80–2.10 (2H, m, C$_3$—H$_2$), 2.16, 2.24 (3H×2, s×2, C$_{5,7}$—CH$_3$), 2.63 (2H, t, J=7.5 Hz, C$_4$—H$_2$), 3.00–3.50 (4H, m, C$_2$—H$_2$, >NCH$_2$—), 3.57 (2H, s, —CH$_2$CO—), 3.44 (2H, br, —CONH$_2$), 6.35 (1H, s, C$_8$—H).

(7) 1-Octyl-6-carbamoylmethyl-5,7-dimethyl-1,2,3,4-tetrahydroquinoline (2.5 g) was dissolved in n-propanol (50 ml) and a solution of NaOH (3.0 g) in water (30 ml) was added, which was followed by stirring at 130° C. for 20 hr under nitrogen. The organic layer of the reaction mixture was separated and the solvent was evaporated under reduced pressure. The residue was dissolved in water (300 ml) and washed with ethyl acetate (100 ml). The aqueous layer was adjusted to pH 1–2 with 6N hydrochloric acid and extracted with chloroform (200 ml). The chloroform layer was dried over anhydrous sodium sulfate. The solvent was evaporated under reduced pressure. The obtained 1-octyl-6-carboxymethyl-5,7-dimethyl- 1,2,3,4-tetrahydroquinoline was dissolved in ethanol (50 ml), and conc. hydrochloric acid (4 ml) was added, which was followed by stirring at 70° C. for 1 hr. The solvent was evaporated under reduced pressure. The residue was neutralized with saturated aqueous solution of sodium hydrogencarbonate and extracted with chloroform (100 ml). After washing with water, the chloroform layer was dried over anhydrous sodium sulfate. The solvent was evaporated under reduced pressure. The residue was purified by silica gel column chromatography (eluent: benzene) to give 1.0 g of oily 1-octyl-6-ethoxycarbonylmethyl-5,7-dimethyl-1,2,3,4-tetrahydroquinoline.

IR (Nujol) cm$^{-1}$; 1732, 1599.

$^1$H-NMR (CDCl$_3$) δ;

0.70–1.00 (3H, br-t, —(CH$_2$)$_7$CH$_3$), 1.10–1.80 (15H, m, —(CH$_2$)$_6$CH$_3$, —COCH$_2$CH$_3$), 1.80–2.10 (2H, m, C$_3$—H$_2$), 2.12, 2.26 (3H×2, s×2, C$_{5,7}$—CH$_3$), 2.62 (2H, t, J=7.5 Hz, C$_4$—H$_2$), 3.00–3.30 (4H, m, C$_2$—H$_2$, >NCH$_2$—), 3.59 (2H, s, —CH$_2$CO—), 4.13 (2H, q, J=7.0 Hz, —COCH$_2$—), 6.33 (1H, s, C$_8$—H).

(8) 1-Octyl-6-ethoxycarbonylmethyl-5,7-dimethyl-1,2,3,4-tetrahydroquinoline (1.0 g) was dissolved in acetic anhydride (5 ml), and a solution of 70% nitric acid (517 mg) in acetic anhydride (3 ml) was dropwise added, which was followed by stirring at the same temperature for 0.5 hr. The reaction mixture was poured into ice water (50 ml), neutralized with saturated aqueous solution of sodium hydrogencarbonate, and extracted with chloroform (50 ml). After washing with water, the chloroform layer was dried over anhydrous sodium sulfate. The solvent was evaporated under reduced pressure. The residue was purified by silica gel column chromatography (eluent: n-hexane-ethyl acetate/n-hexane=1/5) to give 700 mg of oily 1-octyl-6-ethoxycarbonylmethyl-5,7-dimethyl-8-nitro-1,2,3,4-tetrahydroquinoline.

IR (Nujol) cm$^{-1}$; 1732, 1527.

$^1$H-NMR (CDCl$_3$) δ;

0.70–1.00 (3H, br-t, —(CH$_2$)$_7$CH$_3$), 1.10–1.70 (15H, m, —(CH$_2$)$_6$CH$_3$, —COCH$_2$CH$_3$), 1.80–2.10 (2H, m, C$_3$—H$_2$), 2.16 (6H, s, C$_{5,7}$—CH$_3$), 2.64 (2H, t, J=7.5 Hz, C$_4$—H$_2$), 2.70–3.20 (4H, m, C$_2$—H$_2$, >NCH$_2$—), 3.65 (2H, s, —CH$_2$CO—), 4.13 (2H, q, J=7.0 Hz, —COCH$_2$—).

(9) 1-Octyl-6-ethoxycarbonylmethyl-5,7-dimethyl-8-nitro-1,2,3,4-tetrahydroquinoline (700 mg) was dissolved in ethanol (500 ml), and 10% palladium-carbon (200 mg) was added. The mixture was subjected to hydrogenation at room temperature under atmospheric pressure. 10% Palladium-carbon was filtered off and the solvent was evaporated under reduced pressure. The obtained 1-octyl-6-ethoxycarbonylmethyl-5,7-dimethyl-8-amino-1,2,3,4-tetrahydroquinoline was dissolved in chloroform (50 ml). Pivaloyl chloride (207 mg) and triethylamine (192 mg) were added under ice-cooling, and the mixture was stirred at the same temperature for 1 hr. The reaction mixture was washed successively with 5% aqueous citric acid and water, and dried over anhydrous sodium sulfate. The solvent was evaporated under reduced pressure. The residue was purified by silica gel column chromatography (eluent: chloroform-chloroform/methanol=10/1) to give 230 mg of oily title compound.

IR (Nujol) cm$^{-1}$; 1732, 1483.

$^1$H-NMR (CDCl$_3$) δ;

0.70–1.00 (3H, br-t, —(CH$_2$)$_7$CH$_3$), 1.10–1.70 (15H, m, —(CH$_2$)$_6$CH$_3$, —COCH$_2$CH$_3$), 1.35 (9H, s, —C(CH$_3$)$_3$), 1.80–2.10 (2H, m, C$_3$—H$_2$), 2.05, 2.11 (3H×2, s×2, C$_{5,7}$—CH$_3$), 2.40–2.70 (4H, m, C$_4$—H$_2$, >NCH$_2$—), 2.80–2.90 (2H, m, C$_2$—H$_2$), 3.68 (2H, s, —CH$_2$CO—), 4.14 (2H, q, J=7.0 Hz, —COCH$_2$—), 7.35 (1H, br, —CONH—).

EXAMPLE 125

N-(1-Octyl-6-carboxymethyl-5,7-dimethyl-1,2,3,4-tetrahydroquinolin-8-yl)-2,2-dimethylpropanamide N-(1-Octyl-6-ethoxycarbonylmethyl-5,7-dimethyl-1,2,3,4-tetrahydroquinolin-8-yl)-2,2-dimethylpropanamide (230 mg) was dissolved in ethanol (5 ml), and a solution of NaOH (100 mg) in water (2 ml) was added, which was followed by stirring at 50° C. for 1 hr. The solvent of the reaction mixture was evaporated under reduced pressure. The residue was dissolved in water (50 ml) and washed with ethyl acetate (20 ml). The aqueous layer was adjusted to pH 1–2 with 2N sulfuric acid and extracted with chloroform. The chloroform layer was dried over anhydrous sodium sulfate. The solvent was evaporated under reduced pressure to give 130 mg of powdery title compound.

TLC; Silica gel 60F254 Art. 5714 (Merck), CHCl$_3$-MeOH (10:1), Rf value 0.5.

IR (Nujol) cm$^{-1}$; 1732, 1722.

$^1$H-NMR (CDCl$_3$) δ;

0.70–1.00 (3H, br-t, —(CH$_2$)$_7$CH$_3$), 1.10–1.70 (12H, m, —(CH$_2$)$_6$CH$_3$), 1.35 (9H, s, —C(CH$_3$)$_3$), 1.80–2.10 (2H, M, C$_3$—H$_2$), 2.10 (6H, s, C$_{5,7}$—CH$_3$), 2.40–2.70 (4H, m, C$_4$—H$_2$, >NCH$_2$—), 2.80–2.90 (2H, m, C$_2$—H$_2$), 3.68 (2H, s, —CH$_2$CO—), 7.35 (1H, br, —CONH—), 9.50 (2H, br, ½H$_2$SO$_4$, —CO$_2$H).

EXAMPLES 126–154

The compounds of Tables 11 and 12 were obtained according to the method of the above Example 124.

TABLE 11

$R^4 = -\text{NHCOR}^7$

| Example | R¹ | R² | R³ | R⁷ | R⁶ |
|---|---|---|---|---|---|
| 126 | —CH₃ | —CH₂CO₂H | —CH₃ | —C(CH₃)₃ | —(CH₂)₅CH₃ |
| 127 | —CH₃ | —CH₂CO₂H | —CH₃ | —C(CH₃)₃ | —CH₂CH(CH₂CH₃)₂ |
| 128 | —CH₃ | —CH₂CO₂H | —CH₃ | —C(CH₃)₃ | —(CH₂)₆CH₃ |
| 129 | —CH₃ | —CH₂CO₂H | —CH₃ | —C(CH₃)₃ | —CH₂-C₆H₁₁ |
| 130 | —CH₃ | —CH₂CO₂H | —CH₃ | —C(CH₃)₃ | —(CH₂)₂CH(CH₂CH₃)₂ |
| 131 | —CH₃ | —CH₂CO₂H | —CH₃ | —C(CH₃)₃ | —(CH₂)₂O(CH₂)₃CH₃ |
| 132 | —CH₃ | —CH₂CO₂H | —CH₃ | —C(CH₃)₃ | —(CH₂)₂S(CH₂)₃CH₃ |
| 133 | —CH₃ | —CH₂CO₂H | —CH₃ | —C(CH₃)₃ | —CH₂CH₂-C₆H₁₁ |
| 134 | —CH₃ | —CH₂CO₂H | —CH₃ | —C(CH₃)₃ | —(CH₂)₃CH(CH₂CH₃)₂ |
| 135 | —CH₃ | —CH₂CO₂H | —CH₃ | —C(CH₃)₃ | —(CH₂)₃O(CH₂)₃CH₃ |
| 136 | —CH₃ | —CH₂CO₂H | —CH₃ | —C(CH₃)₃ | —(CH₂)₃S(CH₂)₃CH₃ |
| 137 | —CH₃ | —CH₂CO₂H | —CH₃ | —C(CH₃)₃ | —(CH₂)₈CH₃ |
| 138 | —CH₃ | —CH₂CO₂H | —CH₃ | —C(CH₃)₃ | —(CH₂)₉CH₃ |
| 139 | —CH₂CH₃ | —CH₂CO₂H | —CH₂CH₃ | —C(CH₃)₃ | —(CH₂)₅CH₃ |
| 140 | —CH₂CH₃ | —CH₂CO₂H | —CH₂CH₃ | —C(CH₃)₃ | —(CH₂)₇CH₃ |
| 141 | —CH₂CH₃ | —CH₂CO₂H | —CH₂CH₃ | —C(CH₃)₃ | —(CH₂)₉CH₃ |

TABLE 12

$R^4 = -\text{NHCOR}^7$

| Example | R¹ | R² | R³ | R⁷ | R⁶ |
|---|---|---|---|---|---|
| 142 | —OCH₃ | —CH₂CO₂H | —OCH₃ | —C(CH₃)₃ | —(CH₂)₅CH₃ |
| 143 | —OCH₃ | —CH₂CO₂H | —OCH₃ | —C(CH₃)₃ | —(CH₂)₇CH₃ |
| 144 | —OCH₃ | —CH₂CO₂H | —OCH₃ | —C(CH₃)₃ | —(CH₂)₉CH₃ |
| 145 | —CH₃ | —CH₂OH | —CH₃ | —C(CH₃)₃ | —(CH₂)₅CH₃ |
| 146 | —CH₃ | —CH₂OH | —CH₃ | —C(CH₃)₃ | —(CH₂)₇CH₃ |
| 147 | —CH₃ | —CH₂OH | —CH₃ | —C(CH₃)₃ | —(CH₂)₉CH₃ |
| 148 | —CH₃ | —CH₂CO₂H | —CH₃ | —C(CH₃)₂(CH₂)₃CH₃ | —(CH₂)₇CH₃ |
| 149 | —CH₃ | —CH₂CO₂H | —CH₃ | —C(CH₃)₂(CH₂)₅CH₃ | —(CH₂)₇CH₃ |
| 150 | —CH₃ | —CH₂CO₂H | —CH₃ | —CH₂-C₆H₁₁ | —(CH₂)₇CH₃ |
| 151 | —CH₃ | —CH₂CO₂H | —CH₃ | —CH₂-C₆H₅ | —(CH₂)₇CH₃ |
| 152 | —CH₃ | —CH₂CO₂H | —CH₃ | —NH(CH₂)₃CH₃ | —(CH₂)₅CH₃ |

TABLE 12-continued

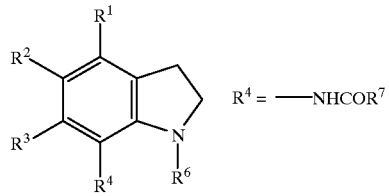

| Example | R$^1$ | R$^2$ | R$^3$ | R$^7$ | R$^6$ |
|---|---|---|---|---|---|
| 153 | —CH$_3$ | —CH$_2$CO$_2$H | —CH$_3$ | —NH(CH$_2$)$_3$CH$_3$ | —(CH$_2$)$_7$CH$_3$ |
| 154 | —CH$_3$ | —CH$_2$CO$_2$H | —CH$_3$ | —NH(CH$_2$)$_3$CH$_3$ | —(CH$_2$)$_9$CH$_3$ |

The $^1$H-NMR values of the compounds of the above Examples 126–154 are shown in the following.

Example 126: 0.70–1.00 (3H, br-t), 1.10–1.70 (8H, m), 1.35 (9H, s), 1.80–2.10 (2H, m), 2.10 (6H, s), 2.40–2.70 (4H, m), 2.80–2.90 (2H, m), 3.68 (2H, s), 7.35 (1H, br), 9.50 (2H, br).

Example 127: 0.70–1.00 (6H, br-t), 1.10–1.70 (5H, m), 1.35 (9H, s), 1.80–2.10 (2H, m), 2.10 (6H, s), 2.40–2.70 (4H, m), 2.80–2.90 (2H, m), 3.68 (2H, s), 7.35 (1H, br), 9.50 (2H, br).

Example 128: 0.70–1.00 (3H, br-t), 1.10–1.70 (10H, m), 1.35 (9H, s), 1.80–2.10 (2H, m), 2.10 (6H, s), 2.40–2.70 (4H, m), 2.80–2.90 (2H, m), 3.68 (2H, s), 7.35 (1H, br), 9.50 (2H, br).

Example 129: 0.80–1.70 (11H, m), 1.35 (9H, s), 1.80–2.10 (2H, m), 2.10 (6H, s), 2.40–2.70 (4H, m), 2.80–2.90 (2H, m), 3.68 (2H, s), 7.35 (1H, br), 9.50 (2H, br).

Example 130: 0.70–1.00 (6H, br-t), 1.10–1.70 (7H, m), 1.35 (9H, s), 1.80–2.10 (2H, m), 2.10 (6H, s), 2.40–2.70 (4H, m), 2.80–2.90 (21H, m), 3.68 (2H, s), 7.35 (1H, br), 9.50 (2H, br).

Example 131: 0.70–1.10 (3H, br-t), 1.10–1.70 (4H, m), 1.35 (9H, s), 1.80–2.10 (2H, m), 2.10 (6H, s), 2.40–2.70 (4H, m), 2.80–2.90 (2H, m), 3.30–3.60 (4H, m), 3.68 (2H, s), 7.35 (1H, br), 9.50 (2H, br).

Example 132: 0.70–1.10 (3H, br-t), 1.10–1.70 (4H, m), 1.35 (9H, s), 1.80–2.10 (2H, m), 2.10 (6H, s), 2.40–2.70 (4H, m), 2.80–2.90 (2H, m), 3.20–3.50 (4H, m), 3.68 (2H, s), 7.35 (1H, br), 9.50 (2H, br).

Example 133: 0.80–1.70 (13H, m), 1.35 (9H, s), 1.80–2.10 (2H, m), 2.10 (6H, s), 2.40–2.70 (4H, m), 2.80–2.90 (2H, m), 3.68 (2H, s), 7.35 (1H, br), 9.50 (2H, br).

Example 134: 0.70–1.00 (6H, br-t), 1.10–1.70 (9H, m), 1.35 (9H, s), 1.80–2.10 (2H, m), 2.10 (6H, s), 2.40–2.70 (4H, m), 2.80–2.90 (2H, m), 3.68 (2H, s), 7.35 (1H, br), 9.50 (2H, br).

Example 135: 0.70–1.10 (3H, br-t), 1.10–1.70 (6H, m), 1.35 (9H, s), 1.80–2.10 (2H, m), 2.10 (6H, s), 2.40–2.70 (4H, m), 2.80–2.90 (2H, m), 3.30–3.60 (4H, m), 3.68 (2H, s), 7.35 (1H, br), 9.50 (2H, br).

Example 136: 0.70–1.10 (3H, br-t), 1.10–1.70 (6H, m), 1.35 (9H, s), 1.80–2.10 (2H, m), 2.10 (6H, s), 2.40–2.70 (4H, m), 2.80–2.90 (2H, m), 3.20–3.50 (4H, m), 3.68 (2H, s), 7.35 (1H, br), 9.50 (2H, br).

Example 137: 0.70–1.10 (3H, br-t), 1.10–1.70 (14H, m), 1.35 (9H, s), 1.80–2.10 (2H, m), 2.10 (6H, s), 2.40–2.70 (4H, m), 2.80–2.90 (2H, m), 3.68 (2H, s), 7.35 (1H, br), 9.50 (2H, br).

Example 138: 0.70–1.10 (3H, br-t), 1.10–1.70 (16H, m), 1.35 (9H, s), 1.80–2.10 (2H, m), 2.10 (6H, s), 2.40–2.70 (4H, m), 2.80–2.90 (2H, m), 3.68 (2H, s), 7.35 (1H, br), 9.50 (2H, br).

Example 139: 0.70–1.10 (3H, br-t), 1.10–1.70 (14H, m), 1.35 (9H, s), 1.80–2.10 (2H, m), 2.40 (2H, q), 2.43 (2H, q), 2.40–2.70 (4H, m), 2.80–2.90 (2H, m), 3.68 (2H, s), 7.35 (1H, br), 9.50 (2H, br).

Example 140: 0.70–1.10 (3H, br-t), 1.10–1.70 (18H, m), 1.35 (9H, s), 1.80–2.10 (2H, m), 2.40 (2H, q), 2.43 (2H, q), 2.40–2.70 (4H, m), 2.80–2.90 (2H, m), 3.68 (2H, s), 7.35 (1H, br), 9.50 (2H, br).

Example 141: 0.70–1.10 (3H, br-t), 1.10–1.70 (22H, m), 1.35 (9H, s), 1.80–2.10 (2H, m), 2.40 (2H, q), 2.43 (2H, q), 2.40–2.70 (4H, m), 2.80–2.90 (2H, m), 3.68 (2H, s), 7.35 (1H, br), 9.50 (2H, br).

Example 142: 0.70–1.10 (3H, br-t), 1.10–1.70 (8H, m), 1.35 (9H, s), 1.80–2.10 (2H, m), 2.40–2.70 (4H, m), 2.80–2.90 (2H, m), 3.52 (2H, s), 3.73 (3H, s), 3.77 (3H, s), 7.35 (1H, br), 9.50 (2H, br).

Example 143: 0.70–1.10 (3H, br-t), 1.10–1.70 (12H, m), 1.35 (9H, s), 1.80–2.10 (2H, m), 2.40–2.70 (4H, m), 2.80–2.90 (2H, m), 3.52 (2H, s), 3.73 (3H, s), 3.77 (3H, s), 7.35 (1H, br), 9.50 (2H, br).

Example 144: 0.70–1.10 (3H, br-t), 1.10–1.70 (16H, m), 1.35 (9H, s), 1.80–2.10 (2H, m), 2.40–2.70 (4H, m), 2.80–2.90 (2H, m), 3.52 (2H, s), 3.73 (3H, s), 3.77 (3H, s), 7.35 (1H, br), 9.50 (2H, br).

Example 145: 0.70–1.10 (3H, br-t), 1.10–1.70 (8H, m), 1.35 (9H, s), 1.80–2.10 (2H, m), 2.17 (3H, s), 2.23 (3H, s), 2.40–2.70 (4H, m), 2.80–2.90 (2H, m), 4.65 (2H, s), 7.35 (1H, br), 9.50 (2H, br).

Example 146: 0.70–1.10 (3H, br-t), 1.10–1.70 (12H, m), 1.35 (9H, s), 1.80–2.10 (2H, m), 2.17 (3H, s), 2.23 (3H, s), 2.40–2.70 (4H, m), 2.80–2.90 (2H, m), 4.65 (2H, s), 7.35 (1H, br), 9.50 (2H, br).

Example 147: 0.70–1.10 (3H, br-t), 1.10–1.70 (16H, m), 1.35 (9H, s), 1.80–2.10 (2H, m), 2.17 (3H, s), 2.23 (3H, s), 2.40–2.70 (4H, m), 2.80–2.90 (2H, m), 4.65 (2H, s), 7.35 (1H, br), 9.50 (2H, br).

Example 148: 0.70–1.00 (6H, br-t), 1.10–1.70 (18H, m), 1.35 (6H, s), 1.80–2.10 (2H, m), 2.10 (6H, s), 2.40–2.70 (4H, m), 2.80–2.90 (2H, m), 3.68 (2H, s), 7.35 (1H, br), 9.50 (2H, br).

Example 149: 0.70–1.00 (6H, br-t), 1.10–1.70 (22H, m), 1.35 (6H, s), 1.80–2.10 (2H, m), 2.10 (6H, s), 2.40–2.70 (4H, m), 2.80–2.90 (2H, m), 3.68 (2H, s), 7.35 (1H, br), 9.50 (2H, br).

Example 150: 0.70–1.10 (3H, br-t), 1.10–2.00 (27H, m), 2.10 (6H, s), 2.40–2.70 (4H, m), 2.80–2.90 (2H, m), 3.68 (2H, s), 7.35 (1H, br), 9.50 (2H, br).

Example 151: 0.70–1.10 (3H, br-t), 1.10–1.70 (12H, m), 1.80–2.10 (2H, m), 2.10 (6H, s), 2.40–2.70 (4H, m), 2.80–2.90 (2H, m), 3.53 (2H, s), 3.68 (2H, s), 7.30 (5H, s), 7.35 (1H, br), 9.50 (2H, br).

Example 152: 0.70–1.10 (6H, br-t), 1.10–1.70 (12H, m), 1.80–2.10 (2H, m), 2.10 (6H, s), 2.40–2.90 (8H, m), 3.68 (2H, s), 7.35 (1H, br), 9.50 (2H, br).

Example 153: 0.70–1.10 (6H, br-t), 1.10–1.70 (16H, m), 1.80–2.10 (2H, m), 2.10 (6H, s), 2.40–2.90 (8H, m), 3.68 (2H, s), 7.35 (1H, br), 9.50 (2H, br).

Example 154: 0.70–1.10 (6H, br-t), 1.10–1.70 (20H, m), 1.80–2.10 (2H, m), 2.10 (6H, s), 2.40–2.90 (8H, m), 3.68 (2H, s), 7.35 (1H, br), 9.50 (2H, br).

EXAMPLE 155

N-(1-Octyl-5carboxy-6-methylindolin-7-yl)-2,2-dimethylpropanamide (1) 5-Bromo-7-methyl-7-nitroindoline (3.6 g) was dissolved in N,N-dimethylformamide (36 ml), and sodium hydride (677 mg) was added, which was followed by stirring at room temperature for 0.5 hr. 1-Iodooctane (3.4 g) was added to the reaction mixture and the mixture was stirred at the same temperature for 24 hr. Ethyl acetate (200 ml) was added to the reaction mixture, and the mixture was washed with water and dried over anhydrous sodium sulfate. Ethyl acetate was evaporated under reduced pressure. The residue was purified by gel column chromatography (eluent: ethyl acetate/n-hexane=1/100–1/50) to give 4.0 g of oily 1-octyl-5-bromo-6-methyl-7-nitroindoline.

IR (Nujol)cm$^{-1}$; 1610, 1568.

$^1$H-NMR (CDCl$_3$) δ;

0.88 (3H, br-t, J=7 Hz, —(CH$_2$)$_7$CH$_3$), 1.00–1.70 (12H, m, —CH$_2$(CH$_2$)$_6$—), 2.25 (3H, s, indoline C$_6$—CH$_3$) 2.93 (2H, t, J=8 Hz, indoline C$_3$—H$_2$), 2.94 (2H, t, J=7 Hz, >NCH$_2$—), 3.57 (2H, t, J=8 Hz, indoline C$_2$—H$_2$), 7.19 (1H, s, indoline C$_4$—H).

(2) 1-Octyl-5-bromo-6-methyl-7-nitroindoline (4.0 g) was dissolved in N-methylpyrrolidone (40 ml), and copper cyanide (1.9 g) was added, which was followed by stirring at 190° C. for 1 hr. Ethyl acetate (100 ml) and water (100 ml) were added to the reaction mixture. The insoluble matter was filtered off. The ethyl acetate layer was washed with water and dried over anhydrous sodium sulfate. Ethyl acetate was evaporated under reduced pressure. The residue was purified by silica gel column chromatography (eluent: ethyl acetate/n-hexane=1/5–1/3) to give 2.4 g of oily 1-octyl-5-cyano-6-methyl-7-nitroindoline.

IR (Nujol)cm$^{-1}$; 2214, 1620.

$^1$H-NMR (CDCl$_3$) δ;

0.88 (3H, br-t, J=7 Hz, —(CH$_2$)$_7$CH$_3$), 1.00–1.70 (12H, m, —CH$_2$(CH$_2$)$_6$—), 2.38 (3H, s, indoline C$_6$—CH$_3$), 3.03 (2H, t, J=8 Hz, indoline C$_3$—H$_2$), 3.04 (2H, t, J=7 Hz, >NCH$_2$—), 3.73 (2H, t, J=8 Hz, indoline C$_2$—H$_2$), 7.15 (1H, s, indoline C$_4$—H).

(3) 1-Octyl-5-cyano-6-methyl-7-nitroindoline (2.4 g) was dissolved in n-propanol and a solution of NaOH (3.0 g) in water (10 ml) was added, which was followed by refluxing for 20 hr. n-Propanol was evaporated under reduced pressure and ethyl acetate (100 ml) was added to the residue. The mixture was washed with water and dried over anhydrous sodium sulfate. Ethyl acetate was evaporated under reduced pressure. The residue was purified by silica gel column chromatography (eluent: ethyl acetate/benzenel1/5–1/1) to give 1.4 g of 1-octyl-5-carboxy-6-methyl-7-nitroindoline as crystals.

IR (Nujol)cm$^{-1}$; 1679, 1620.

$^1$H-NMR (CDCl$_3$) δ;

0.88 (3H, br-t, J=7 Hz, —(CH$_2$)$_7$CH$_3$), 1.00–1.70 (12H, m, —CH$_2$(CH$_2$)$_6$—), 2.47 (3H, s, indoline C$_6$—CH$_3$), 3.02 (2H, t, J=8 Hz, indoline C$_3$—H$_2$), 3.03 (2H, t, J=7 Hz, >NCH$_2$—), 3.69 (2H, t, J=8 Hz, indoline C$_2$—H$_2$), 5.00 (1H, br, —CO$_2$H), 7.73 (1H, s, indoline C$_4$—H).

(4) 1-Octyl-5-carboxy-6-methyl-7-nitroindoline (1.4 g) was dissolved in methanol (30 ml), and conc. sulfuric acid (4.1 g) was added, which was followed by refluxing for 4 hr. Methanol was evaporated under reduced pressure. Ethyl acetate (100 ml) was added to the residue. The mixture was washed with water and dried over anhydrous sodium sulfate. Ethyl acetate was evaporated under reduced pressure. The residue was purified by silica gel column chromatography (eluent: chloroform/methanol=1/0–10/1) to give 750 mg of 1-octyl-5-methoxycarbonyl-6-methyl-7-nitroindoline as crystals.

IR (Nujol) cm$^{-1}$; 1679, 1620.

$^1$H-NMR (CDCl$_3$) δ;

0.88 (3H, br-t, J=7 Hz, —(CH$_2$)$_7$CH$_3$), 1.00–1.70 (12H, m, —CH$_2$(CH$_2$)$_6$—), 2.43 (3H, s, indoline C$_6$—CH$_3$), 3.00 (2H, t, J=8 Hz, indoline C$_3$—H$_2$), 3.02 (2H, t, J=7 Hz, >NCH$_2$—), 3.66 (2H, t, J=8 Hz, indoline C$_2$—H$_2$), 3.82 (3H, s, —CO$_2$CH$_3$), 7.62 (1H, s, indoline C$_2$—H).

(5) 1-Octyl-5-methoxycarbonyl-6-methyl-7-nitroindoline (750 mg) was dissolved in ethanol (50 ml), and 10% palladium-carbon (150 mg), which was followed by hydrogenation at 40° C. for 15 hr. 10% Palladium-carbon was filtered off and ethanol was evaporated under reduced pressure. Chloroform (100 ml) was added to the residue. The mixture was washed with water and dried over anhydrous sodium sulfate. Chloroform was evaporated under reduced pressure. The obtained 1-octyl-7-amino-5-methoxycarbonyl-6-methylindoline was dissolved in chloroform (10 ml). Pivaloyl chloride (310 mg) and triethylamine (286 mg) were added under ice-cooling, which was followed by stirring at room temperature for 1 hr. Chloroform (50 ml) was added to the reaction mixture. The mixture was washed successively with 5% aqueous citric acid and water, and dried over anhydrous sodium sulfate. Chloroform was evaporated under reduced pressure. The residue was purified by silica gel column chromatography (eluent: chloroform/methanol=1/0–20/1) to give 580 mg of oily N-(1-octyl-5-methoxycarbonyl-6-methylindolin-7-yl)-2,2-dimethylpropanamide.

IR (Nujol)cm$^{-1}$; 1708, 1651.

$^1$H-NMR (CDCl$_3$) δ;

0.87 (3H, br-t, J=7 Hz, —(CH$_2$)$_7$CH$_3$), 1.00–1.70 (12H, m, —CH$_2$(CH$_2$)$_6$—), 1.34 (9H, s, —C(CH$_3$)$_3$), 2.39 (3H, s, indoline C$_6$—CH$_3$), 2.93 (2H, t, J=8 Hz, indoline C$_3$—H$_2$), 3.25 (2H, t, J=7 Hz, >NCH$_2$—), 3.51 (2H, t, J=8 Hz, indoline C$_2$—H$_2$), 3.79 (3H, s, —CO$_2$CH$_3$), 6.76 (1H, br, —CONH—), 7.55 (1H, s, indoline C$_4$—H).

(6) N-(1-Octyl-5-methoxycarbonyl-6-methylindolin-7-yl)-2,2-dimethylpropanamide (580 mg) was dissolved in methanol (10 ml) and a solution of NaOH (290 mg) in water (5 ml) was added, which was followed by stirring at 60° C. for 4 hr. Methanol was evaporated under reduced pressure. Water (50 ml) was added to the residue and the mixture was washed with ethyl acetate (20 ml). The aqueous layer was adjusted to pH 6–7 with 2N sulfuric acid and extracted with chloroform (100 ml). The chloroform layer was washed with water and dried over anhydrous sodium sulfate. Chloroform was evaporated under reduced pressure to give 380 mg of the title compound.

IR (Nujol)cm$^{-1}$; 1668, 1645, 1615.

$^1$H-NMR (CDCl$_3$) δ;
0.79 (3H, br, —(CH$_2$)$_7$CH$_3$), 0.80–1.80 (12H, m, —CH$_2$(CH$_2$)$_6$), 1.34 (9H, s, —C(CH$_3$)$_3$), 2.38 (3H, s, indoline C$_6$—H$_3$), 2.94 (2H, t, J=8 Hz, indoline C$_3$—H$_2$), 3.27 (2H, t, J=7 Hz, >NCH$_2$—), 3.54 (2H, t, J=8 Hz, indoline C$_2$—H$_2$), 6.80 (2H, br, —CONH—, —CO$_2$H), 7.67 (1H, s, indoline C$_4$—H).

EXAMPLES 156–160

The compounds of Table 13 were obtained according to the method of the above Example 155.

TABLE 13

R$^4$ = —NHCOR$^7$

| Example | R$^1$ | R$^2$ | R$^3$ | R$^7$ | R$^6$ |
|---|---|---|---|---|---|
| 156 | —H | —CO$_2$H | —CH$_3$ | —C(CH$_3$)$_3$ | —(CH$_2$)$_5$CH$_3$ |
| 157 | —H | —CO$_2$H | —CH$_3$ | —C(CH$_3$)$_3$ | —(CH$_2$)$_9$CH$_3$ |
| 158 | —CH$_3$ | —CO$_2$H | —CH$_3$ | —C(CH$_3$)$_3$ | —(CH$_2$)$_5$CH$_3$ |
| 159 | —CH$_3$ | —CO$_2$H | —CH$_3$ | —C(CH$_3$)$_3$ | —(CH$_2$)$_7$CH$_3$ |
| 160 | —CH$_3$ | —CO$_2$H | —CH$_3$ | —C(CH$_3$)$_3$ | —(CH$_2$)$_9$CH$_3$ |

The $^1$H-NMR values of the compounds of the above Examples 156–160 are shown in the following.

Example 156: 0.79 (3H, br-t), 0.80–1.80 (8H, m), 1.34 (9H, s), 2.38 (3H, s), 2.94 (2H, t), 3.27 (2H, t), 3.54 (2H, t), 6.80 (2H, br), 7.67 (1H, s).

Example 157: 0.79 (3H, br-t), 0.80–1.80 (16H, m), 1.34 (9H, s), 2.38 (3H, s), 2.94 (2H, t), 3.27 (2H, t), 3.54 (2H, t), 6.80 (2H, br), 7.67 (1H, s).

Example 158: 0.79 (3H, br-t), 0.80–1.80 (8H, m), 1.33 (9H, s), 2.40 (3H, s), 2.45 (3H, s), 2.95 (2H, t), 3.26 (2H, t), 3.54 (2H, t), 6.80 (2H, br).

Example 159: 0.79 (3H, br-t), 0.80–1.80 (12H, m), 1.33 (9H, s), 2.40 (3H, s), 2.45 (3H, s), 2.95 (2H, t), 3.26 (2H, t), 3.54 (2H, t), 6.80 (2H, br).

Example 160: 0.79 (3H, br-t), 0.80–1.80 (16H, m), 1.33 (9H, s), 2.40 (3H, s), 2.45 (3H, s), 2.95 (2H, t), 3.26 (2H, t), 3.54 (2H, t), 6.80 (2H, br).

With the aim of demonstrating the superior properties of the compound of the present invention, ACAT inhibitory activity, serum total cholesterol reducing effect, in vitro plasma lipoperoxidation inhibitory activity, ex vivo plasma lipoperoxidation inhibitory activity, solubility in water at pH 6.8 and plasma concentration on oral administration were determined.

Experimental Example 1

ACAT Inhibitory Activity

A high cholesterol feed [a feed added with cholesterol (1%), Clea Japan, Inc.] was fed to male Japanese white rabbits weighing 2–2.5 kg at 100 g per day and the rabbits were bred for 4 weeks. The rabbits were killed by bleeding under anesthesia and small intestine was removed. The mucosal membrane of small intestine was peeled, collected and homogenated. The homogenate was centrifuged at 4° C. and 10,000 rpm for 15 min. The obtained supernatant was further centrifuged at 4° C. and 41,000 rpm for 30 minutes to give microsomal fractions. The microsomal suspension as an enzyme sample, dimethyl sulfoxide (DMSO, 5 μl) or a test compound dissolved in DMSO (test compound solution 5 μl), and reaction substrate [1-$^{14}$C]-oleoyl CoA were added to 0.15M phosphate buffer to the total amount of 500 μl. After incubation at 37° C. for 7 minutes, a chloroform-methanol mixture was added to stop the reaction. Water was added thereto and mixed, and chloroform layer was separated. The solvent was evaporated to dryness, and the residue was re-dissolved in n-hexane. The mixture was subjected to thin layer chromatography using a silica gel plate. The spots of cholesteryl oleate on the silica gel plate were scraped, and quantitatively assayed on a liquid scintillation counter. The ACAT inhibitory activity of the test compound was expressed as a proportion (%) of inhibition of cholesteryl oleate, namely, the proportion of inhibition of cholesteryl oleate production as compared to control, the results of which are shown in Table 14.

TABLE 14

| Test compound | ACAT inhibition (%) |
|---|---|
| Example 1 | 99.2 |
| Example 3 | 92.5 |
| Example 4 | 93.6 |
| Example 36 | 94.0 |
| Example 40 | 92.7 |
| Example 76 | 94.7 |
| Example 116 | 92.0 |
| Example 120 | 92.3 |
| Example 121 | 92.5 |
| Example 122 | 92.0 |
| Example 125 | 93.0 |
| YM-750 | 92.0 |

YM-750: 1-cycloheptyl-1-[(2-fluorenyl)methyl]-3-(2,4,6-trimethyl-phenyl)urea

Experimental Example 2

Serum Total Cholesterol Reducing Effect

Male Wister rats weighing 180–200 g were bred under free access to a high cholesterol feed [added with cholesterol (1%), cholic acid (0.5%) and coconut oil (10%), Clea Japan, Inc.] for 3 days, during which period a test compound (3 mg/kg and 10 mg/kg) suspended in 5% gum arabic solution was forcibly administered once a day orally for 3 days. Only 5% gum arabic solution was administered to control animals. After final administration, the test animals were fasted and blood was taken 5 hours later. The serum total cholesterol level was determined using a commercially available assay kit (cholesterol-CII-Test Wako, Wako Pure Chemical Industries, Ltd.). The activity of the test compound was expressed as a proportion (%) of reduction of serum total cholesterol level, namely, the proportion of reduction of serum total cholesterol as compared to control, the results of which are shown in Table 15.

TABLE 15

| Test compound | Reduction (%) of serum total cholesterol | |
|---|---|---|
| | 3 mg/kg/day | 10 mg/kg/day |
| Example 1 | 52.8 | 57.1 |
| Example 3 | 54.2 | 61.2 |
| Example 4 | 58.8 | 57.5 |
| Example 18 | 45.1 | 56.6 |
| Example 25 | 45.0 | 52.3 |
| Example 36 | 60.0 | 58.9 |
| Example 40 | 51.3 | 56.2 |
| Example 71 | 26.5 | 52.3 |
| Example 81 | 31.7 | 53.8 |
| Example 116 | 26.5 | 50.9 |
| Example 120 | 45.8 | 44.6 |
| Example 121 | 87.8 | 48.1 |
| Example 122 | 88.2 | 50.0 |
| Example 125 | 30.2 | 47.9 |
| Example 155 | 55.2 | 58.5 |
| Example 159 | 53.8 | 57.5 |
| YM-750 | 37.7 | 46.4 |

YM-750: 1-cycloheptyl-1-[(2-fluorenyl)methyl]-3-(2,4,6-trimethyl-phenyl)urea

Experimental Example 3

In vitro Plasma Lipoperoxidation Inhibitory Activity

Under ether anesthesia, blood was taken from male Wister rats weighing 160–190 g that had been fasted for 16 hours, and heparinized plasma was separated by conventional method. DMSO (10 μl) or a test compound (final concentration $10^{-5}$M) dissolved in DMSO (test compound solution 10 μl) was added to plasma (1.0 ml), and the mixture was incubated at 37° C. for 5 minutes. Distilled water (10 μl) or aqueous solution (10 μl) of copper sulfate (final concentration 1M) was added, followed by incubation at 37° C. for 4 minutes. After incubation, the concentration of lipid peroxide in the sample was determined using a commercially available assay kit (Lipoperoxide Test Wako, Wako Pure Chemical Industries, Ltd.). Specifically, lipid peroxide in the sample was allowed to develop color by thiobarbiturate method and assayed as malondialdehyde. The activity of the test compound was expressed as a proportion (%) of inhibition of malondialdehyde production, namely, the proportion of inhibition of malondialdehyde production as compaed to control, the results of which are shown in Table 16.

TABLE 16

| Test compound | Inhibition (%) of plasma lipoperoxidation |
|---|---|
| Example 1 | 51.7 |
| Example 3 | 49.2 |
| Example 4 | 51.2 |
| Example 11 | 44.5 |
| Example 18 | 44.0 |
| Example 25 | 63.5 |
| Example 36 | 41.5 |
| Example 71 | 48.1 |
| Example 76 | 51.7 |
| Example 81 | 47.1 |
| Example 116 | 45.5 |
| Example 121 | 41.6 |
| Example 125 | 48.0 |
| Example 155 | 47.7 |
| Example 159 | 48.3 |

Experimental Example 4

Ex vivo Plasma Lipoperoxidation Inhibitory Activity

A test compound suspended in 5% gum arabic solution was forcibly administered orally to male Wister rats weighing 160–190 g that had been fasted for 16 hr. Only 5% gum arabic solution was administered to control animals. At 1 hour after administration, blood was taken under ether anesthesia and heparinized plasma was separated by conventional method. The plasma (1.0 ml) was processed in the same manner as in Experimental Example 3 and the amount of produced malondialdehyde was determined. The activity of the test compound was expressed as a proportion (%) of inhibition of malondialdehyde production, namely, the proportion of inhibition of malondialdehyde production as compared to control, the results of which are shown in Table 17.

TABLE 17

| Dose | Inhibition (%) of plasma lipoperoxidation | | | |
|---|---|---|---|---|
| | Example 4 | Example 18 | Example 36 | Probucol |
| 10 mg/kg | 39.0 | 27.1 | 41.6 | — |
| 100 mg/kg | — | — | — | 15.4 |

Probucol: 4,4-isopropylidenedithiobis(2,6-di-t-butylphenol)

Experimental Example 5

Solubility

A pulverized test compound (10 mg) was added to buffer (1 ml, pH 6.8), and the mixture was shaken for 1 hr at 25° C. The mixture was passed through a membrane filter and the concentration of the test compound in the filtrate was determined by high performance liquid chrmatography, the results of which are shown in Table 18.

Table 18

| Test compound | Solubility (mg/ml) |
|---|---|
| Example 4 | 6.9 |
| Example 18 | 7.3 |
| Example 25 | 0.8 |
| Example 36 | 4.2 |
| Example 71 | 0.1 |
| YM-750 | <0.01 |

YM-750: 1-cycloheptyl-1-[(2-fluorenyl)methyl]-3-(2,4,6-trimethyl-phenyl)urea

Experimental Example 6

Oral Administration

A test compound (30 mg/kg) suspended in 5% gum arabic solution was forcibly administered orally to male Wister rats weighing 200–250 g that had been fasted for 16 hr. At 0.5, 1, 2, 4 and 6 hours after administration, blood was taken and heparinized plasma was separated by conventional method. The concentration of the test compound in the plasma was determined by high performance liquid chromatography, the results of which are shown in Table 19.

TABLE 19

| Test compound | Highest concentration in plasma (μg/ml) |
|---|---|
| Example 4 | 1.4 |
| Example 36 | 2.2 |

Experimental Example 7

Oral Administration

A test compound (30 mg/kg) suspended in 5% gum arabic solution was forcibly administered orally to male SD rats weighing 200–250 g that had been fasted for 16 hr. At 0.5, 1, 2, 4 and 6 hours after administration, blood was taken and heparinized plasma was separated by conventional method. The concentration of the test compound in the plasma was determined by high performance liquid chromatography, the results of which are shown in Table 20.

TABLE 20

| Test compound | Highest concentration in plasma ($\mu$g/ml) |
|---|---|
| Example 4 | 13.6 |
| Example 36 | 12.2 |

What is claimed is:

1. A heterocyclic compound of the formula (I)

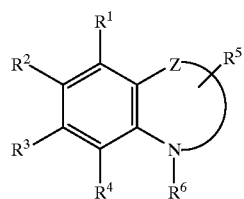

(I)

wherein
one of $R^1$, $R^2$ and $R^5$ is hydroxy, carboxy, alkoxycarbonyl, a group of the formula —$NR^9R^{10}$ wherein $R^9$ and $R^{10}$ are each independently hydrogen atom or lower alkyl, or alkyl or alkenyl substituted by hydroxy, carboxy, sulfonic acid group or phosphoric acid group, alkoxycarbonyl or a group of the formula —$NR^9R^{10}$ wherein $R^9$ and $R^{10}$ are each independently hydrogen atom or lower alkyl, and the other two are each independently hydrogen atom, lower alkyl or lower alkoxy;
either $R^3$ or $R^4$ is a group of the formula —$NHCOR^7$ wherein $R^7$ is alkyl, alkoxyalkyl, alkylthioalkyl, cycloalkyl, cycloalkylalkyl, aryl, arylalkyl or a group of the formula —$NHR^8$ wherein $R^8$ is alkyl, cycloalkyl, cycloalkylalkyl, aryl or arylalkyl, and the other is hydrogen atom, lower alkyl or lower alkoxy;
$R^6$ is alkyl, alkenyl, alkoxyalkyl, alkylthioalkyl, cycloalkyl, cycloalkylalkyl or arylalkyl; and
Z is

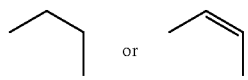

or a pharmaceutically acceptable salt thereof, provided that when one of $R^1$, $R^2$ and $R^5$ is carboxy or alkoxycarbonyl, Z should be a group of the formula

2. The heterocyclic compound of claim 1, wherein, in the formula (I), one of $R^1$, $R^2$ and $R^5$ is alkyl or alkenyl substituted by hydroxy, carboxy, sulfonic acid group or phosphoric acid group, alkoxycarbonyl or a group of the formula —$NR^9R^{10}$ wherein $R^9$ and $R^{10}$ are each independently hydrogen atom or lower alkyl, and the other two are each independently hydrogen atom, lower alkyl or lower alkoxy, or a pharmaceutically acceptable salt thereof.

3. The heterocyclic compound of claim 2, wherein, in the formula (I), Z is

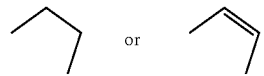

or a pharmaceutically acceptable salt thereof.

4. The heterocyclic compound of claim 3, wherein, in the formula (I), one of $R^1$, $R^2$ and $R^5$ is alkyl substituted by hydroxy, carboxy, alkoxycarbonyl or a group of the formula —$NR^9R^{10}$ wherein $R^9$ and $R^{10}$ are each independently lower alkyl, and the other two are each independently hydrogen atom, lower alkyl or lower alkoxy, and either $R^3$ or $R^4$ is a group of the formula —$NHCOR^7$ wherein $R^7$ is alkyl, alkoxyalkyl, alkylthioalkyl, cycloalkyl, cycloalkylalkyl, aryl, arylalkyl or a group of the formula —$NHR^8$ wherein $R^8$ is alkyl, and the other is hydrogen atom, lower alkyl or lower alkoxy, or a pharmaceutically acceptable salt thereof.

5. The heterocyclic compound of claim 4, wherein, in the formula (I), $R^1$ and $R^3$ are each independently hydrogen atom, lower alkyl or lower alkoxy, either $R^2$ or $R^5$ is alkyl substituted by hydroxy, carboxy, alkoxycarbonyl or a group of the formula —$NR^9R^{10}$ wherein $R^9$ and $R^{10}$ are each independently lower alkyl, and the other is hydrogen atom, lower alkyl or lower alkoxy, and $R^4$ is a group of the formula —$NHCOR^7$ wherein $R^7$ is alkyl, alkoxyalkyl, alkylthioalkyl, cycloalkyl, cycloalkylalkyl, aryl, arylalkyl or a group of the formula —$NHR^8$ wherein $R^8$ is alkyl, or a pharmaceutically acceptable salt thereof.

6. The heterocyclic compound of claim 5, wherein, in the formula (I), either $R^2$ or $R^5$ is alkyl substituted by hydroxy, carboxy, alkoxycarbonyl or a group of the formula —$NR^9R^{10}$ wherein $R^9$ and $R^{10}$ are each independently lower alkyl, and the other is hydrogen atom, or a pharmaceutically acceptable salt thereof.

7. The heterocyclic compound of claim 6, wherein, in the formula (I), $R^1$ and $R^3$ are each independently hydrogen atom or lower alkyl, either $R^2$ or $R^5$ is alkyl substituted by hydroxy, carboxy, alkoxycarbonyl or a group of the formula —$NR^9R^{10}$ wherein $R^9$ and $R^{10}$ are each independently lower alkyl, and the other is hydrogen atom, $R^4$ is a group of the formula —$NHCOR^7$ wherein $R^7$ is alkyl, cycloalkyl or cycloalkylalkyl, and $R^6$ is alkyl, cycloalkyl or cycloalkylalkyl, or a pharmaceutically acceptable salt thereof.

8. The heterocyclic compound of claim 7, wherein, in the formula (I), $R^2$ is alkyl substituted by hydroxy, carboxy, alkoxycarbonyl or a group of the formula —$NR^9R^{10}$ wherein $R^9$ and $R^{10}$ are each independently lower alkyl, and $R^5$ is hydrogen atom, or a pharmaceutically acceptable salt thereof.

9. The heterocyclic compound of claim 8, which is represented by the formula (IIa)

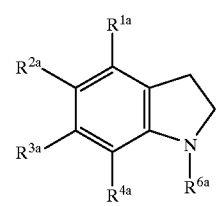

(IIa)

wherein $R^{1a}$ is hydrogen atom or lower alkyl, $R^{3a}$ is lower alkyl, $R^{2a}$ is alkyl substituted by hydroxy or carboxy, $R^{4a}$ is a group of the formula —NHCOR$^{7a}$ wherein R$^{7a}$ is alkyl, cycloalkyl or cycloalkylalkyl, and R$^{6a}$ is alkyl, cycloalkyl or cycloalkylalkyl, or a pharmaceutically acceptable salt thereof.

10. The heterocyclic compound of claim 9, wherein, in the formula (IIa), R$^{1a}$ is hydrogen atom or lower alkyl, R$^{3a}$ is lower alkyl, R$^{2a}$ is alkyl substituted by hydroxy or carboxy, R$^{4a}$ is a group of the formula —NHCOR$^{7a}$ wherein R$^{7a}$ is alkyl, and R$^{6a}$ is alkyl, or a pharmaceutically acceptable salt thereof.

11. The heterocyclic compound of claim 10, wherein the compound of the formula (IIa) is selected from the group consisting of:

(1) N-(1-hexyl-5-carboxythyl-4,6-dimethylindolin-7-yl)-2,2-dimethylpropanamide, (2) N-(1-heptyl-5-carboxymethyl-4,6-dimethylindolin-7-yl)-2,2-dimethylpropanamide, (3) N-(1-octyl-5-carboxymethyl-4,6-dimethylindolin-7-yl)-2,2-dimethylpropanamide, (4) N-(1-nonyl-5 carboxymethyl-4,6-dimethylindolin-7-yl)-2,2-dimethylpropanamide, (5) N-(1-decyl-5-carboxymethyl-4,6-dimethylindolin-7-yl)-2,2-dimethylpropanamide, (6) N-(1-undecyl-5-carboxymethyl-4,6-dimethylindolin-7-yl)-2,2-dimethylpropanamide, (7) N-(1-dodecyl-5-carboxymethyl-4,6-dimethylindolin-7-yl)-2,2-dimethylpropanamide, (8) N-(1-hexyl-5-hydroxymethyl-6-methylindolin-7-yl)-2,2-dimethylpropanamide, (9) N-(1-hexyl-5-hydroxymethyl-4,6-dimethylindolin-7-yl)-2,2-dimethylpropanamide,

(10) N-(1-heptyl-5-hydroxymethyl-6-mthylindolin-7-yl)-2,2-dimethylpropanamide,

(11) N-(1-heptyl-5-hydroxymethyl-4,6-dimethylindolin-7-yl)-2,2-dimethylpropanamide,

(12) N-(1-octyl-5-hydroxymethyl-6-methylindolin-7-yl)-2,2-dimethylpropanamide, and

(13) N-(1-octyl-5-hydroxymethyl-4,6-dimethylindolin-7-yl)-2,2-dimethylpropanamide, or a pharmaceutically acceptable salt thereof.

12. The heterocyclic compound of claim 1, wherein, in the formula (I), one of R$^1$, R$^2$ and R$^5$ is hydroxy, carboxy, alkoxycarbonyl or a group of the formula —NR$^9$R$^{10}$ wherein R$^9$ and R$^{10}$ are each independently hydrogen atom or lower alkyl, and the other two are each independently hydrogen atom, lower alkyl or lower alkoxy, or a pharmaceutically acceptable salt thereof.

13. The heterocyclic compound of claim 12, which is represented by the formula (IIc)

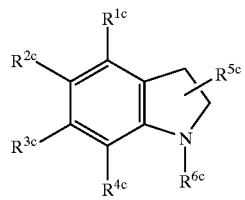

(IIc)

wherein one of R$^{1c}$, R$^{2c}$ and R$^{5c}$ is hydroxy, carboxy, alkoxycarbonyl or a group of the formula —NR$^{9c}$R$^{10c}$ wherein R$^{9c}$ and R$^{10c}$ are each independently hydrogen atom or lower alkyl and the other two are each independently hydrogen atom, lower alkyl or lower alkoxy, either R$^{3c}$ or R$^{4c}$ is a group of the formula —NHCOR$^{7c}$ wherein R$^{7c}$ is alkyl, alkoxyalkyl, alkylthioalkyl, cycloalkyl, cycloalkylalkyl, aryl, arylalkyl or a group of the formula —NHR$^{8c}$ wherein R$^{8c}$ is alkyl, cycloalkyl, cycloalkylalkyl, aryl or arylalkyl and the other is hydrogen atom, lower alkyl or lower alkoxy, and R$^{6c}$ is alkyl, alkenyl, alkoxyalkyl, alkylthioalkyl, cycloalkyl, cycloalkylalkyl or arylalkyl, or a pharmaceutically acceptable salt thereof.

14. The heterocyclic compound of claim 13, wherein, in the formula (IIc), R$^{1c}$ and R$^{3c}$ are each independently hydrogen atom, lower alkyl or lower alkoxy, R$^{2c}$ is carboxy, R$^{4c}$ is a group of the formula —NHCOR$^{7c}$ wherein R$^{7c}$ is alkyl, cycloalkyl or cycloalkylalkyl, R$^{5c}$ is hydrogen atom, and R$^{6c}$ is alkyl, cycloalkyl or cycloalkylalkyl, or a pharmaceutically acceptable salt thereof.

15. The heterocyclic compound of claim 14, wherein, in the formula (IIc), R$^{1c}$ is hydrogen atom or lower alkyl, R$^{3c}$ is lower alkyl, R$^{2c}$ is carboxyl, R$^{4c}$ is a group of the formula —NHCOR$^{7c}$ wherein R$^{7c}$ is alkyl, R$^{5c}$ is hydrogen atom, and R$^{6c}$ is alkyl, or a pharmaceutically acceptable salt thereof.

16. The heterocyclic compound of claim 15, wherein the compound of the formula (IIc) is selected from the group consisting of:

(1) N-(1-hexyl-5-carboxy-6-methylindolin-7-yl)-2,2-dimethylpropanamide, (2) N-(1-octyl-5-carboxy-6-methylindolin-7-yl)-2,2-dimethylpropanamide, (3) N-(1-decyl-5carboxy-6-methylindolin-7-yl)-2,2-dimethylpropanamide, (4) N-(1-hexyl-5-carboxy-4,6-dimethylindolin-7-yl)-2,2-dimethylpropanamide, (5) N-(1-octyl-5-carboxy-4,6-dimethylindolin-7-yl)-2,2-dimethylpropanamide, and (6) N-(1-decyl-5-carboxy-4,6-dimethylindolin-7-yl)-2,2-dimethylpropanamide, or a pharmaceutically acceptable salt thereof.

17. A pharmaceutical composition comprising an effective amount of a heterocyclic compound of claim 1 or a pharmaceutically acceptable salt thereof.

18. A method of inhibiting acyl-CoA:cholesterol acyltransferase in a patient in need of same which comprises administering to such patient the composition of claim 17.

19. A method of inhibiting lipoperoxidation in a patient in need of same which comprises administering to such patient the composition of claim 17.

* * * * *

UNITED STATES PATENT AND TRADEMARK OFFICE
CERTIFICATE OF CORRECTION

PATENT NO.   : 6,063,806
DATED        : May 16, 2000
INVENTOR(S)  : Shoji Kamiya et al.

It is certified that error appears in the above-identified patent and that said Letters Patent is hereby corrected as shown below:

Column 3,
Line 64, change "phosphonic" to -- phosphoric --.

Column 49,
Tables 11 and 12, line 1 thereof, rewrite the formula as:

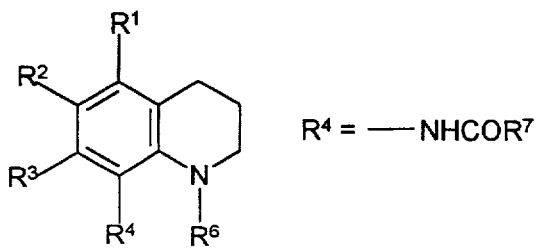

Column 51,
Table 12, line 1 thereof, rewrite the formula as:

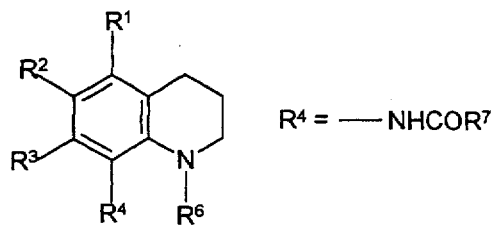

Signed and Sealed this

Eighth Day of January, 2002

*Attest:*

*Attesting Officer*

JAMES E. ROGAN
*Director of the United States Patent and Trademark Office*